(12) United States Patent
O'Keefe et al.

(10) Patent No.: US 7,053,202 B2
(45) Date of Patent: May 30, 2006

(54) IMMUNOGLOBULIN DNA CASSETTE MOLECULES, MONOBODY CONSTRUCTS, METHODS OF PRODUCTION, AND METHODS OF USE THEREFOR

(75) Inventors: Theresa L. O'Keefe, Waltham, MA (US); Paul D. Ponath, San Francisco, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 208 days.

(21) Appl. No.: 10/272,899

(22) Filed: Oct. 17, 2002

(65) Prior Publication Data

US 2004/0033561 A1 Feb. 19, 2004

Related U.S. Application Data

(60) Provisional application No. 60/392,364, filed on Jun. 26, 2002, provisional application No. 60/350,166, filed on Oct. 19, 2001.

(51) Int. Cl.
- *C07H 21/02* (2006.01)
- *C07H 21/04* (2006.01)
- *G03C 5/00* (2006.01)

(52) U.S. Cl. .............. 536/23.53; 430/320.1; 536/23.1

(58) Field of Classification Search ................ 514/44; 530/387.3; 536/23.53, 23.1; 435/320.1
See application file for complete search history.

(56) References Cited

U.S. PATENT DOCUMENTS

| | | | |
|---|---|---|---|
| 5,624,821 A | 4/1997 | Winter et al. | |
| 5,648,260 A | 7/1997 | Winter et al. | |
| 6,312,689 B1 | 11/2001 | LaRosa | |
| 6,352,832 B1 | 3/2002 | LaRosa et al. | |
| 6,395,497 B1 | 5/2002 | LaRosa | |
| 6,406,694 B1 | 6/2002 | LaRosa | |
| 6,406,865 B1 | 6/2002 | LaRosa | |
| 6,448,021 B1 | 9/2002 | LaRosa | |
| 6,451,522 B1 | 9/2002 | LaRosa | |
| 6,458,353 B1 | 10/2002 | LaRosa | |
| 6,491,915 B1 | 12/2002 | LaRosa | |
| 6,696,550 B1 | 2/2004 | LaRosa et al. | |
| 6,727,349 B1 | 4/2004 | LaRosa et al. | |
| 2002/0106369 A1* | 8/2002 | Horvath et al. ......... 424/131.1 |
| 2002/0147312 A1* | 10/2002 | O'Keefe et al. ......... 530/387.3 |
| 2004/0126851 A1 | 7/2004 | LaRosa et al. | |
| 2004/0132980 A1 | 7/2004 | LaRosa et al. | |
| 2004/0151721 A1 | 8/2004 | O'Keefe et al. | |
| 2004/0265303 A1 | 12/2004 | La Rosa et al. | |
| 2005/0048052 A1 | 3/2005 | LaRosa | |

FOREIGN PATENT DOCUMENTS

| | | |
|---|---|---|
| AU | 764825 | 2/2000 |
| CA | 2 336 250 | 2/2000 |
| CA | 2 399 080 | 8/2001 |
| GB | 2 209 757 | 5/1989 |
| WO | WO 88/07054 | 9/1888 |
| WO | WO 88/07089 | 9/1988 |
| WO | WO 89/07142 | 8/1989 |
| WO | WO 94/29351 | 12/1994 |
| WO | WO 00/05265 | 2/2000 |
| WO | WO 01/57226 | 8/2001 |

OTHER PUBLICATIONS

Lund et al. (1991) Journal of Immunology 147(8): 2657-2662.*

* cited by examiner

Primary Examiner—Gary Nickol
Assistant Examiner—Sean Aeder
(74) Attorney, Agent, or Firm—Fish and Richardson P.C.

(57) ABSTRACT

Featured are DNA molecules, expression vectors, and host cells useful for creation of immunoglobulins, as well as novel immunoglobulin molecules termed monobodies. Additionally provided are methods of production of immunoglobulins, including monobodies, as well as methods of using the disclosed immunoglobulin and monobody constructs, expression vectors and host cells containing DNA encoding molecules for production of immunoglobulin and monobody proteins.

37 Claims, 14 Drawing Sheets

Figure 1  Antibody Production and Conversion System

Figure 9  Antibody Production Levels in Small Culture

Figure 10  Proposed Monobody Structures

Figure 11  Proposed Monobody Interchain Connections

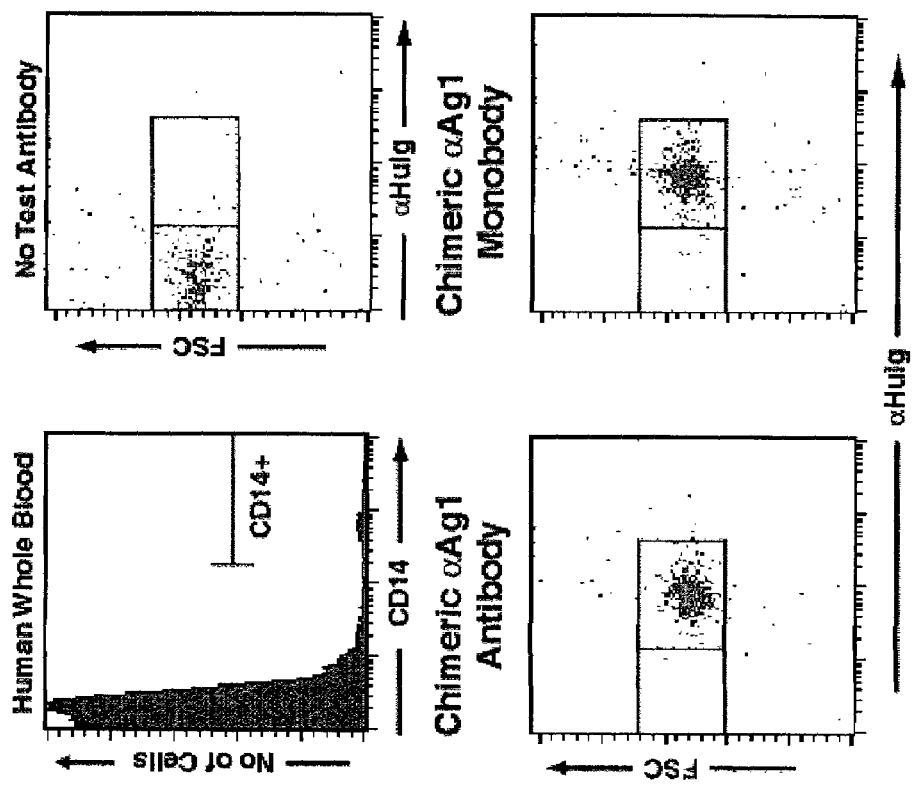
Figure 14  Binding of αAg1 Antibody and Monobody to Moncytes

IMMUNOGLOBULIN DNA CASSETTE MOLECULES, MONOBODY CONSTRUCTS, METHODS OF PRODUCTION, AND METHODS OF USE THEREFOR

CROSS-REFERENCE TO RELATED APPLICATIONS

This application claims the benefit of U.S. Provisional Application No. 60/350,166, filed Oct. 19, 2001, and U.S. Provisional Application No. 60/392,364, filed Jun. 26, 2002, the contents of which are incorporated herein by this reference.

FIELD OF THE INVENTION

The present invention relates to immunoglobulin DNA cassette molecules, including novel constructs termed monobody constructs, as well as methods for producing expression vectors and host cells containing DNA cassettes and capable of producing immunoglobulin and monobody molecules. More particularly, the invention relates to DNA cassette molecules useful for creating a variety of immunoglobulin therapeutic molecules, including novel monobodies, as well as methods for producing and using such molecules.

BACKGROUND OF THE INVENTION

Immunoglobulins (Igs), or antibodies, as the main effectors of humoral immunity and endogenous modulators of the immune response, have proven to be valuable molecules in clinical applications such as diagnostic, therapeutic and prophylactic purposes, as well as in research contexts. An immunoglobulin molecule is composed of four protein chains; two heavy and two light chains which must be produced, associate and correctly fold to be effectively exported from the cell. The heavy and light chains are held together covalently through disulfide bonds. The heavy chains are also covalently linked via disulfide bonds in a base portion often referred to as the constant region. This constant region is also responsible for a given immunoglobulin molecule being mutually recognizable with certain sequences found at the surface of particular cells or factors. There are five known major classes of constant regions (IgG, IgM, IgA, IgD and IgE) which determine the class, or effector function, of the immunoglobulin molecule.

The cDNA of the heavy chain is composed of a leader sequence (a signal sequence) (approximately 57 bp/19 aa) which is removed upon maturation of the protein, a variable region, VH (approximately 350 bp/115 aa), and the constant region, CH (approximately 990 bp/330 aa). The cDNA of the light chain is composed of a leader sequence (approximately 66 bp/22 aa) which is removed upon maturation of the protein; a variable region, Vκ or Vλ (approximately 350 bp/115 aa); and a constant region, Cκ or Cλ (approximately 321 bp/107 aa). The light chains covalently bind to the N-terminal Y branches of the two heavy chains. The variable regions of the heavy and light chains, approximately 110–125 amino acids in length, confer specificity of particular antigenic epitopes for a particular immunoglobulin molecule.

Although the antibody genes can be engineered to be expressed in bacteria and plants such as corn, effective expression of antibodies should be carried out using mammalian systems in order to obtain efficient mammalian post-translational modifications and folding processes required for effective assembly and secretion of functional antibody molecules. Presently used methods for production of antibodies include in vivo immunization followed by collection and processing in order to obtain purified antibody. However, such methods are limited in that they may require large amounts of antigen to produce response, and they are time-consuming processes. Furthermore, antigen may not generate effective response in the animal, and generation of therapeutically useful antibodies is questionable. Therefore the time and effort expended to produce antibodies using such present methods may not culminate in sufficient antibody production.

Additional methods for production of antibodies involve creation of expression systems for use in mammalian cells lines, such as CHO or murine myeloma cell lines. See, McCafferty, J., et al. Eds. *Antibody Engineering, A Practical Approach*. IRL Press, (1997). Present methods for development of antibody expression systems involve creation of a vector composed of a light chain flanked by its promoter and a poly-adenylation (polyA) region in a plasmid. Also, a heavy chain vector composed of a heavy chain construct flanked by a promoter and a polyA region is created. The promoter/insert/polyA region of the heavy chain may then alternatively be combined into the light chain vector in order to create a single vector containing both heavy and light chain molecules. In these methods, genomic DNA or mRNA of a heavy or light chain is cloned into an expression vector for use in mammalian cell lines or transgenic animals. Another method of construction includes vectors which are created wherein a framework of the immunoglobulin chain (e.g., heavy chain sequence) is inserted prior to addition of particular variable sequences as desired, such as has been disclosed and described in U.S. Pat. No. 5,780,225.

Currently utilized methods of production of immunoglobulin expression systems, however, require multiple cloning steps resulting in production of only a single desired molecule. If alterations in specificity (governed by the variable region) or effector function (governed by the constant region) of the antibody are desired, re-assembly of a new light and/or heavy chain vector, followed by re-assembly of a final combined vector is required.

It thus would be desirable to provide new immunoglobulin molecule constructs useful as effectors of humoral immunity and modulators of immune responses, as well as methods for effective production of such molecules. It would be particularly desirable to provide such constructs and methods that would facilitate production of antibodies having desired specificity in comparison to methods of the prior art. It also would be desirable to provide such constructs and methods that allow for facilitated production of immunoglobulins having desired effector functions as compared to those of the prior art. Such molecules and methods preferably would be simple in construction and require straightforward assembly steps in order to obtain the desired immunoglobulins, thereby resulting in rapid generation of desired antibody molecules with comparatively little effort. Furthermore, development of a system resulting in large scale production in comparison to present methods will be beneficial for development and production of protein therapeutics.

SUMMARY OF THE INVENTION

The present invention features antibody (immunoglobulin) DNA cassette constructs useful for rapid, simple generation of desired immunoglobulin molecules. Additionally provided are vectors and host cells comprising DNA cassette constructs of the invention, as well as methods of using the constructs, vectors, and host cells for production of immunoglobulins. Compositions and methods encompassed in the present invention taken together comprise an antibody production and conversion system.

In one embodiment of the invention a DNA cassette construct comprises an immunoglobulin DNA cassette wherein the immunoglobulin cassette is a light chain immunoglobulin cassette. In another embodiment of the invention, the immunoglobulin DNA cassette is a heavy chain immunoglobulin cassette. The immunoglobulin cassette preferably comprises an immunoglobulin leader sequence operably linked to a stable immunoglobulin domain region. In an additional aspect, a DNA cassette construct further comprises a transcriptional promoter region operably linked to the leader molecule.

In another embodiment, the DNA cassette construct further comprises a poly-adenylation region operably linked to the stable immunoglobulin domain of the construct.

Preferably, the operable linkage of the immunoglobulin cassette comprises a cloning sequence, such as for example, a multiple cloning site, wherein the sequence is available for addition of further immunoglobulin domains for production of a complete immunoglobulin molecule.

In a specific embodiment of the invention, the DNA cassette molecule comprises an immunoglobulin leader sequence operably linked to an immunolglobulin constant region, wherein the operable linkage between the leader sequence and constant region includes a cloning sequence wherein a desired immunoglobulin variable region may be inserted for production of a complete immunoglobulin chain. In one aspect of the invention, the immunoglobulin chain is a heavy chain immunoglobulin molecule.

In another aspect of the invention, the immunoglobulin chain is a light chain immunoglobulin molecule. In one aspect the light chain is a kappa (κ) chain immunoglobulin. In another aspect, the light chain is a lambda (λ) chain immunoglobulin. Preferred sequences of the immunoglobulin cassettes include sequences shown in SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, or a sequence at least 85%, 90%, 95%, 99% or higher identical thereto.

Further included in embodiments of the invention are expression vectors comprising immunoglobulin DNA cassette molecules. The expression vectors may comprise one or more immunoglobulin DNA cassette molecules. In one preferred aspect of the invention the expression vector comprises two immunoglobulin DNA cassette molecules, wherein one of the DNA cassette molecules is a heavy chain immunoglobulin cassette and the second is a light chain immunoglobulin cassette.

In another preferred aspect of the invention, an expression vector comprises a single immunoglobulin DNA cassette molecule. The expression vector may comprise a light chain immunoglobulin DNA cassette molecule or a heavy chain immunoglobulin DNA cassette molecule.

In additional aspects of the invention, preferred insert sequences for use in the DNA cassettes and vectors of the present invention are provided. The insert sequence may comprise any one of heavy or light chain variable domain immunoglobulin sequences, or heavy or light chain constant domain immunoglobulin sequences. Such preferred insert sequences can include nucleotide and/or protein sequences and can be selected from the group consisting of SEQ ID NO: 83, SEQ ID NO: 84, SEQ ID NO: 85, and SEQ ID NO: 86, SEQ ID NO: 87, and SEQ ID NO: 88.

Additionally provided are host cells and cell lines comprising immunoglobulin DNA cassette molecules and expression vectors of the invention, as well as methods of using such host cells for production of antibodies. In aspects of the invention, host cells can consist of a bacterial cell, a yeast cell or a mammalian cell or cell line. In a particularly preferred embodiment, host cells are mammalian cells such as a lymphocytic cell line, CHO, or COS cells.

In another embodiment of the invention, a DNA cassette construct comprises an immunoglobulin DNA cassette wherein the immunoglobulin cassette is a monobody cassette. The immunoglobulin monobody cassette preferably comprises an immunoglobulin leader sequence operably linked to a stable immunoglobulin hinge and constant domain regions. In an additional aspect, a DNA cassette construct further comprises a transcriptional promoter region operably linked to the leader molecule.

In one aspect of the invention, the immunoglobulin DNA monobody cassette is a heavy chain monobody cassette, wherein the monobody molecule comprises an immunoglobulin heavy chain comprising leader sequence operably linked to an immunoglobulin heavy chain constant region attached to a hinge region, then further attached to a heavy chain constant region, wherein the heavy chain constant region comprises a IgG3 hinge and IgG3 CH1 domains linked to IgG1 CH2 and CH3 regions. Preferred sequences of the immunoglobulin cassettes include sequences shown in SEQ ID NO:105, SEQ ID NO:106, or a sequence at least 85%, 90%, 95%, 99% or higher identical thereto.

In another aspect of the invention, the immunoglobulin DNA monobody cassette is a light chain monobody cassette, wherein the DNA cassette molecule comprises an immunoglobulin leader sequence operably linked to a stable monobody region, wherein the operable linkage between the leader sequence and the stable monobody region includes a cloning sequence wherein a desired immunoglobulin variable region may be inserted for production of a complete extended immunoglobulin light chain molecule. In one aspect of the invention, the stable monobody region is a monobody cassette comprising an extended light chain comprising a leader sequence operably linked to an immunoglobulin light chain constant region attached via a linker sequence to a hinge region, then attached to a heavy chain constant region. In a preferred aspect, the hinge is an IgG1 hinge. In another aspect, the heavy chain constant region comprises IgG1 CH2 and CH3 domains. In still another aspect, the hinge is an IgG3 hinge. Preferred sequences of the immunoglobulin cassettes include sequences shown in SEQ ID NO:107, SEQ ID NO:108, SEQ ID NO:109, SEQ ID NO:110, or a sequence at least 85%, 90%, 95%, 99% or higher identical thereto.

In yet another aspect, the invention includes vectors comprising a monobody cassette constructs. In one aspect, the invention comprises a vector comprising an extended light chain monobody cassette and a heavy chain monobody cassette. In a preferred embodiment, a monobody vector comprises, an extended light chain and a heavy chain monobody cassette, wherein the extended light chain cassette comprises a leader sequence operably linked to an immunoglobulin C kappa domain attached via a linker sequence to an IgG3 hinge and IgG1 CH2 and CH3 constant regions; and wherein the heavy chain cassette comprises a heavy chain leader sequence operably linked to a constant region, wherein the heavy chain constant region comprises a IgG3 hinge and IgG3 CHI domains linked to IgG1 CH2 and CH3 regions.

In another preferred embodiment, a monobody vector comprises, an extended light chain and a heavy chain monobody cassette, wherein the extended light chain cassette comprises a leader sequence operably linked to an immunoglobulin C kappa domain attached via a linker sequence to an IgG1 hinge and IgG1 CH2 and CH3 domains; and wherein the heavy chain cassette comprises a leader sequence operably linked to a complete intact heavy chain constant region.

Further, disclosed are methods of production of immunoglobulin DNA cassette molecules, as well as methods for production of antibodies (whether single antibodies or batteries of antibodies, as desired) utilizing the immunoglobulin DNA cassette molecules and expression vectors of the present invention. One preferred method includes production of a battery of antibodies having identical antigen specificity, with variable effector function. An additional preferred method includes production of a battery of antibodies having identical effector function, with variable antigen specificities.

Additionally disclosed are methods of production of immunoglobulin monobody molecules utilizing the monobody cassette molecules and expression vectors of the present invention.

Other aspects and embodiments of the invention are discussed infra.

BRIEF DESCRIPTION OF THE FIGURES

FIG. 14 depicts demonstrative results of monobody binding activity to monocytes expressing target antigen 1D9.

DETAILED DESCRIPTION OF THE INVENTION

Figure 1:
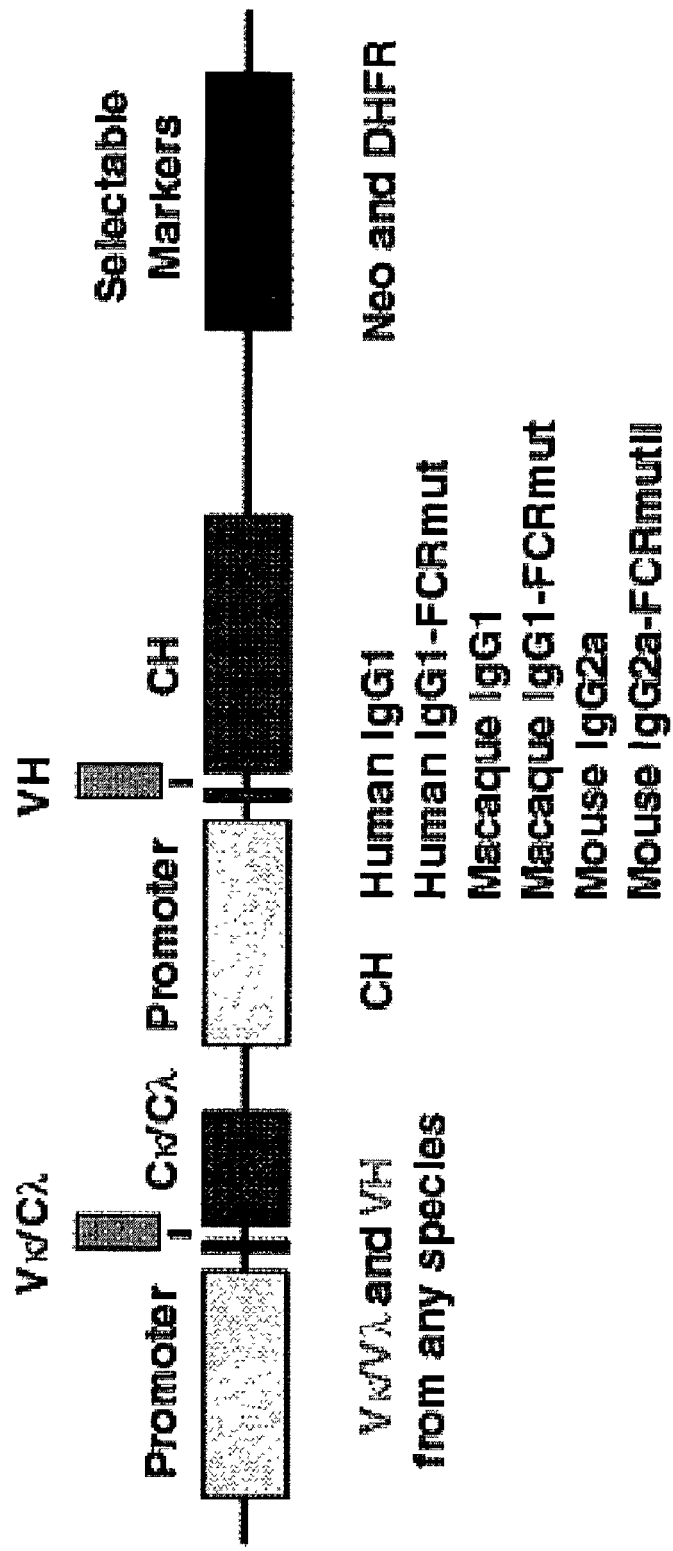
FIG. 1 depicts an antibody production and conversion system.

The present invention pertains to immunoglobulin DNA cassette molecules, including heavy chain immunoglobulin DNA cassettes and a light chain immunoglobulin DNA cassettes useful for facilitated generation of immunoglobulin proteins and antibody production. Additionally the invention pertains to DNA insert sequences for use in the DNA cassette system.

Accordingly, various aspects of the invention relate to immunoglobulin DNA cassette molecules, nucleic acids comprising the aforesaid immunoglobulin cassette molecules, as well as vectors and host cells containing the aforesaid nucleic acid sequences. Additional aspects of the invention relate to DNA insert sequences for use with the DNA cassette molecules. Methods of producing the aforesaid DNA cassette molecules, as well as methods of using the DNA cassette molecules of the invention are also encompassed by the invention. The nucleic acid molecules, vectors, cells and methods described herein comprise an antibody production and conversion system of the present invention, depicted in FIG. 1.

In order that the present invention may be more readily understood, certain terms are first defined. Additional definitions are set forth throughout the detailed description.

As used herein, the term "antibody" refers to a protein comprising at least one, and preferably two, heavy (H) chain variable regions (abbreviated herein as VH), and at least one and preferably two light (L) chain variable regions (abbreviated herein as VL). The antibody can further include heavy and light chain constant regions (abbreviated herein as CH and CL, respectively), to thereby form a heavy and light immunoglobulin chain, respectively. In one embodiment, the antibody is a tetramer of two heavy immunoglobulin chains and two light immunoglobulin chains.

As used herein, the term "immunoglobulin" refers to a protein consisting of one or more polypeptides substantially encoded by immunoglobulin genes.

As used herein, "isotype" refers to the antibody class (e.g., IgM or IgG1) that is encoded by heavy chain constant region genes.

The term "isolated nucleic acid", as used herein is intended to refer to a nucleic acid molecule in which the nucleotide sequences including DNA cassette molecules as described herein encoding an antibody or antibody portion are free of other nucleotide sequences encoding other antibodies or antibody portions, which other sequences may naturally flank the nucleic acid in human genomic DNA. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

As used herein, "DNA cassette" refers to nucleic acid sequences which have been constructed in such a way so as to facilitate addition of the cassette to additional vector sequences. Additionally, the DNA cassettes of the invention facilitate incorporation of additional sequences in operable linkage with the prepared DNA cassette sequences for preparation of desired immunoglobulin sequences, e.g., in one or two cloning steps.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated.

The term "recombinant host cell" (or simply "host cell"), as used herein, is intended to refer to a cell into which a recombinant expression vector has been introduced. It should be understood that such terms are intended to refer not only to a particular subject cell, but to the progeny of such a cell. Because certain modifications may occur in succeeding generations due to either mutation or environmental influences, such progeny may not, in fact, be identical to the parent cell, but are still included within the scope of the terms "recombinant host cell" or "host cell" as used herein.

As used herein, the term "substantially identical," or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

As used herein, the term "assembly characteristics" refers to one or more of the following properties: (1) dimer or tetramer formation; (2) percentage of properly folded antibody, e.g., formation of correct disulfide bonds; (3) binding affinity and/or specificity; (4) yield of functional antibody, as measured by, e.g., binding affinity; or (5) high levels of antibody production, e.g., at least from about 10 μg/ml, preferably, 100 μg/ml, more preferably 800 μg/ml, and yet more preferably 1.5 mg/ml or higher production levels.

As used herein, "specific binding" refers to the property of the antibody: (1) to bind to a predetermined antigen with an affinity of at least $1 \times 10^7$ $M^{-1}$, and (2) to preferentially bind to the predetermined antigen with an affinity that is at least two-fold greater than its affinity for binding to a non-specific antigen (e.g., BSA, casein) other than the predetermined antigen. The phrases "an antibody recognizing an antigen" and "an antibody specific for an antigen" are used interchangeably herein with the term "an antibody which binds specifically to an antigen".

The term "glycosylation pattern" is defined as the pattern of carbohydrate units that are covalently attached to a protein, more specifically to an immunoglobulin protein. In some embodiments, the glycosylation pattern of an antibody produced using the present methods can be characterized as being substantially similar to glycosylation patterns of naturally occurring antibodies. In other embodiments, the glycosylation pattern may be altered (e.g., reduced or increased) by recombinant or chemical methods. For example, residues which are part of the N-glycosylation motif, Asn-X-Ser, wherein X can be any amino acid residue except proline (e.g., asparagine residue at position 297 in the human IgG constant region) can be replaced, e.g., using mutagenesis techniques, with another amino acid that cannot be glycosylated, e.g., alanine. Such modified constant regions have a reduced number of glycosylation sites, and in some embodiments, can be aglycosylated.

The term "naturally-occurring" as used herein as applied to an object refers to the fact that an object can be found in nature. For example, a polypeptide (e.g., an antibody) or polynucleotide sequence that is present in an organism (including viruses) that can be isolated from a source in nature and which has not been intentionally modified by man in the laboratory is naturally-occurring.

The term "antigen-binding fragment" of an antibody (or simply "antibody portion," or "fragment"), as used herein, refers to one or more fragments of a full-length antibody that retain the ability to specifically bind to an antigen. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR).

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, a "chimeric immunoglobulin heavy chain" refers to those immunoglobulin heavy chains having a portion of the immunoglobulin heavy chain, e.g., the variable region, at least 85%, preferably, 90%, 95%, 99% or more identical to a corresponding amino acid sequence in an immunoglobulin heavy chain from a particular species, or belonging to a particular antibody class or type, while the remaining segment of the immunoglobulin heavy chain (e.g., the constant region) being substantially identical to the corresponding amino acid sequence in another immunoglobulin molecule. For example, the heavy chain variable region has a sequence substantially identical to the heavy chain variable region of an immunoglobulin from one species (e.g., a "donor" immunoglobulin, e.g., a rodent immunoglobulin), while the constant region is substantially identical to the constant region of another species immunoglobulin (e.g., an "acceptor" immunoglobulin, e.g., a human immunoglobulin).

As used herein, the term "humanized" or "CDR-grafted" light chain variable region refers to an immunoglobulin light chain comprising one or more CDR's, or having an amino acid sequence which differs by no more than 1 or 2 amino acid residues to a corresponding one or more CDR's from one species, or antibody class or type, e.g., a "donor" immunoglobulin (e.g., a non-human (usually a mouse or rat) immunoglobulin, or an in vitro generated immunoglobulin); and a framework region having an amino acid sequence about 85% or higher, preferably 90%, 95%, 99% or higher identical to a corresponding part of an acceptor immunoglobulin framework from a different species, or antibody class or type, e.g., a naturally-occurring immunoglobulin framework (e.g., a human framework) or a consensus framework.

Typically, the immunoglobulin providing the CDR's is called the "donor" and the immunoglobulin providing the framework, e.g., an immunoglobulin DNA cassette, is called the "acceptor." In one embodiment, the donor immunoglobulin is a non-human (e.g., rodent), or an in vitro generated immunoglobulin, e.g., an immunoglobulin generated by phage display. The acceptor framework is a naturally-occurring (e.g., a human) framework or a consensus sequence, or a sequence about 85% or higher, preferably 90%, 95%, 99% or higher identical thereto.

The light chain variable region may have replacements in only one or more of the CDR's, and thus will be referred to herein as a "CDR-grafted" light variable chain. In other embodiments, it may include framework substitutions, in addition to the CDR substitutions, which will be referred to herein as a "humanized" light chain variable region.

A "hybrid antibody molecule" refers to an antibody, or an antigen-binding fragment thereof (e.g., a Fab, F(ab')$_2$, Fv or a single chain Fv fragment), which includes a humanized, or CDR-grafted, light chain variable region, and a chimeric heavy chain variable region. Each heavy and light chain variable region of a hybrid antibody may, optionally, include a corresponding constant, which can be identical or similar (e.g., about 85% or higher, preferably 90%, 95%, 99% or higher) to the acceptor constant regions (e.g., human immunoglobulin, or a constant region from yet another species, or antibody class or type). The term "hybrid antibody" or "hybrid antibody molecule" does not encompass a typical chimeric antibody, e.g., an antibody whose light and heavy chains are obtained from immunoglobulin variable and constant region genes belonging to different species or class, or a typical humanized antibody, e.g., an antibody whose light and heavy chain CDR's belong to different species or class.

In addition to the above discussion and the various references to existing literature teachings, reference is made to standard textbooks of molecular biology that contain definitions and methods and means for carrying out basic techniques encompassed by the present invention. See, for example, Maniatis, et al, Molecular Cloning: A Laboratory Manual, Cold Spring Harbor Laboratory, New York, 1982 and the various references cited therein, and in particular, Colowick et al., Methods in Enzymology Vol 152, Academic Press, Inc. (1987), the contents of which are expressly incorporated herein by reference.

As described below, the process makes use of techniques which are known to those of skill in the art and can be applied as described herein to produce and identify immunoglobulin molecules of desired antigenic specificity or immunoglobulin molecules of desired effector function: the polymerase chain reaction (PCR), to amplify and clone either known molecules encoding a desired immunoglobulin molecule, or diverse cDNAs encoding antibody mRNAs found in antibody-producing tissue; mutagenesis protocols to further increase the diversity of these cDNAs; gene transfer protocols to introduce immunoglobulin genes into cultured (prokaryotic and eukaryotic) cells for the purpose of expressing them; as well as screening protocols to detect genes encoding antibodies of desired antigenic specificity.

Various aspects of the invention are described in further detail in the following subsections.

Production of Antibody Production and Conversion System

Immunoglobulin DNA cassette molecules and immunoglobulin insert molecules can be generated using art-recognized techniques for producing nucleic acid molecules comprising portions of immunoglobulin chains, as described in detail below. Immunoglobulins can be of the various isotypes, including: IgG (e.g., IgG1, IgG2, IgG3, IgG4), IgM, IgA1, IgA2, IgD, or IgE. Preferably, the antibody is an IgG isotype. The immunoglobulin molecules can be adapted to any include full-length (e.g., an IgG1 or IgG4 immunoglobulin) or alternatively can include only an antigen-binding fragment (e.g., a Fab, F(ab')$_2$, Fv or a single chain Fv fragment).

Nucleic Acids, Vectors and Host Cells

Figure 2:
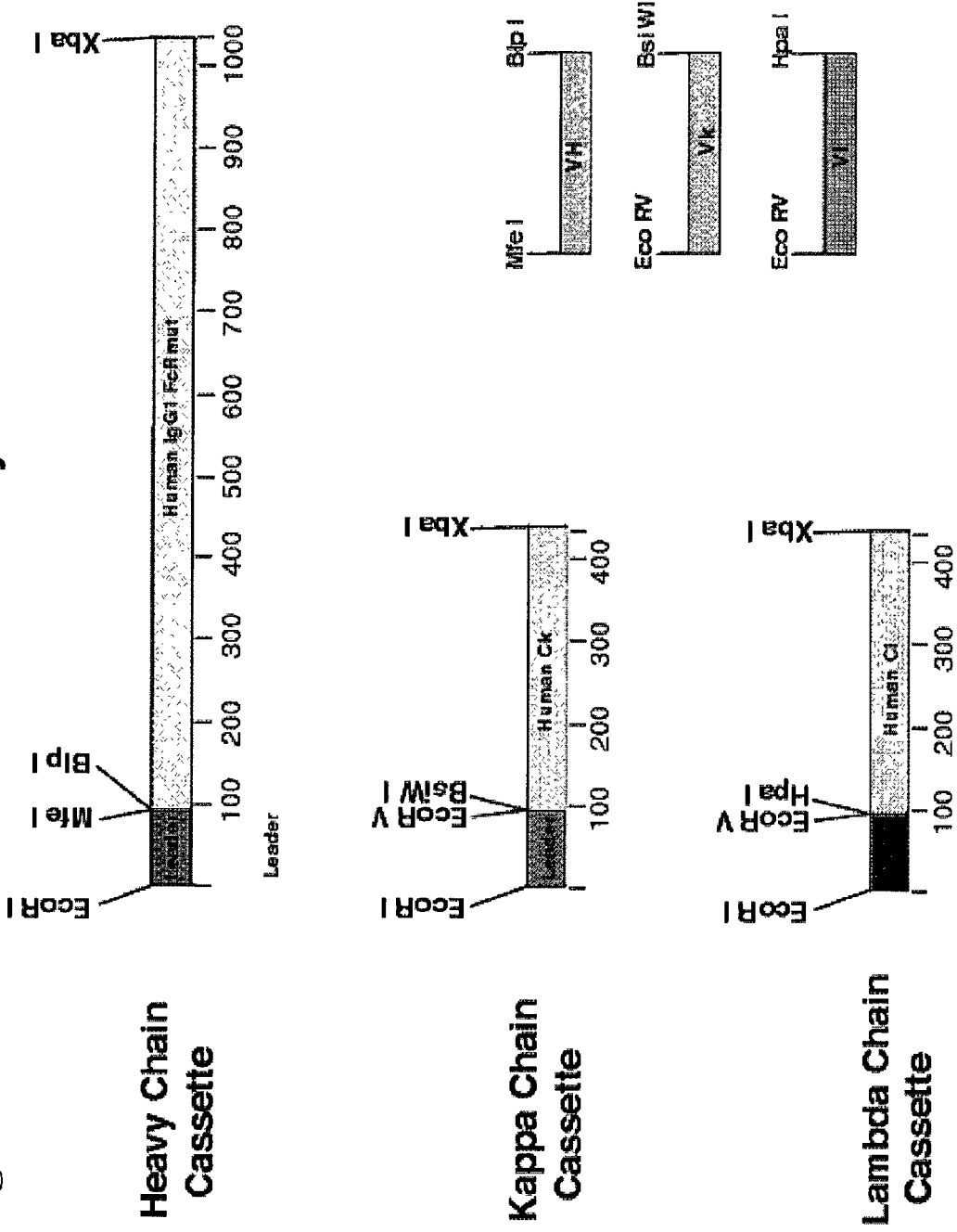
FIG. 2 depicts structure of antibody cassette molecules and insert molecules.

One aspect of the invention pertains to isolated immunoglobulin DNA cassette nucleic acids, vector and host cell compositions that can be used for recombinant expression of antibodies and antigen-binding fragments of the invention. In one embodiment, an isolated nucleic acid including an immunoglobulin DNA cassette comprising an immunoglobulin leader sequence operably linked to a stable immunoglobulin domain is provided. Preferably the leader sequence is an immunoglobulin heavy chain leader sequence linked to a constant region of a heavy chain immunoglobulin. An additional preferred embodiment includes an immunoglobulin DNA cassette wherein the leader sequence is an immunoglobulin light chain leader sequence operably linked to a light chain constant region. Preferred immunoglobulin DNA cassette molecules of the invention are depicted in FIG. 2. Preferred immunoglobulin DNA cassette nucleotide sequences can include sequences SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, and SEQ ID NO: 81, or a sequence at least 85%, 90%, 95%, 99% or higher identical thereto. Preferred immunoglobulin DNA cassette nucleotide sequences can include sequences SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, and SEQ ID NO: 82, or a sequence at least 85%, 90%, 95%, 99% or higher identical thereto.

Preferably, the operable linkage between the leader sequence and the stable immunoglobulin domain (e.g., constant region) comprises sequences amenable to digestion using restriction endonucleases. Preferred restriction endonuclease sites engineered into the operable linkage include EcoRV, PpuMI or MfeI and BlpI or BsiWI, however, additional or alternative sites may be engineered in order to accommodate the particularly desired additional sequences used in conjunction with the DNA cassette. Methods for engineering restriction sites (e.g., site directed mutagenesis) and determination of preferred sites through sequence analyses are well known in the art. Restriction sites engineered in the linkage allow for subsequent incorporation of additional immunoglobulin sequences (e.g., variable region) such that the additional sequences are incorporated in operable linkage with the leader and stable domain (e.g., constant region) to allow production of a nucleic acid encoding a complete operable immunoglobulin molecule (e.g., cloning of the additional variable sequence remains in frame with the leader and constant region to produce nucleic acid encoding an immunoglobulin protein including leader, variable, and constant domains).

In an additional embodiment of the present invention, immunoglobulin DNA insert sequences preferable for use in conjunction with the immunoglobulin DNA cassettes are provided. Preferably, an immunoglobulin variable domain DNA sequence is isolated, wherein the 5' and 3' ends of the insert sequences comprise DNA sequences available for restriction endonucleases complementary to sites available in the DNA cassette. In one embodiment, immunoglobulin variable sequences are isolated using PCR techniques known in the art, wherein primer sequences are engineered to incorporate DNA restriction endonuclease sequences in the proper placement to allow operable linkage upon incorporation into the immunoglobulin DNA cassette.

The present compositions and methods of the invention are meant to further include immunoglobulin DNA cassettes wherein an immunoglobulin leader sequence is operably linked to a stable immunoglobulin variable domain, wherein an operable linkage sequence is included at the 3' end of the variable domain to accommodate incorporation of additional sequences for use in the DNA cassette. In such preferred molecules, constant immunoglobulin insert sequences may be incorporated by methods similar to those methods of incorporation of additional sequences as described herein as well as using methods known in the art. Use of such additional DNA cassette molecules will similarly result in production of a desired nucleic acid molecule encoding an immunoglobulin molecule having the desired effector function (e.g., IgG1, IgG2, IgG3, IgG4), IgM, IgA1, IgA2, IgD, or IgE). Accordingly, one of skill in the art will comprehend the methods and compositions described herein in conjunction with methods known in the art in order to prepare and use such additional constructs in accordance with the disclosure of the present invention.

As described herein, the DNA cassette molecules as well as isolated immunoglobulin DNA insert sequences may be used for production of immunoglobulin molecules which include full-length (e.g., an IgG1 or IgG4) immunoglobulin. Alternatively the DNA cassette molecules and isolated immunoglobulin DNA insert sequences may be used to encode partial or altered immunoglobulin proteins such as an antigen-binding fragment (e.g., a Fab, F(ab')$_2$, Fv) or a single chain Fv fragment for example. In production of the desired molecules, the immunoglobulin DNA cassette may be altered to tailor to the requirement of the desired protein. For example, the stable immunoglobulin domain, e.g., constant region, may be truncated, mutated or constructed in such a way as to mostly eliminate the domain in order to allow for production of the desired immunoglobulin once additional insert immunoglobulin sequences are incorporated. For example, if a DNA cassette useful for preparation of Fv fragments is desired, a leader sequence may be operably linked to a stable domain comprising a minimal variable domain sequence to allow for incorporation of additional variable sequences for production of functional Fv fragments as desired.

It will be appreciated by the skilled artisan that nucleotide sequences encoding the immunoglobulin DNA cassette molecules (e.g., a leader sequence, a stable immunoglobulin domain, as well as insert sequences), can be derived from the nucleotide and amino acid sequences described in the present application or from additional sources of sequences of immunoglobulin genes known in the art using the genetic code and standard molecular biology techniques.

The nucleic acid compositions of the present invention, while often in a native sequence (except for modified restriction sites and the like), may be derived from either known isolated immunoglobulin DNA or cDNA, or mixtures may be mutated in accordance with standard techniques for production of gene sequences. For coding sequences, such mutations may affect amino acid sequence as desired. In particular, nucleotide sequences may be substantially identical to or derived from native V, D, J, or constant cDNA sequences (where "derived" indicates that a sequence is identical or modified from another sequence).

Sequences substantially identical, similar or homologous (e.g., at least about 85% sequence identity) to the sequences disclosed herein are also part of this application. In some embodiments, the sequence identity can be about 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, New York , 6.3.1–6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453 ) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http:/www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

It is understood that the immunoglobulin DNA cassette molecules and immunoglobulin DNA insert molecules of the present invention may include sequences which result in antibodies that have additional conservative or non-essential amino acid substitutions, which do not have a substantial effect on antigen binding or other immunoglobulin functions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of an antibody, without abolishing or more preferably, without substantially altering a biological activity (e.g., binding to a particular antigen), whereas an "essential" amino acid residue results in such a change.

The imunoglobulin DNA cassette molecules and/or immunoglobulin DNA insert molecules may encompass sequences wherein the amino acid sequences have an immunoglobulin sequence that differs by, e.g., at least one, two, three, four, five, ten or more amino acid residues from another sequence. As used herein, the term "differs" includes different amino acid sequences created by, e.g., deletions, insertions, or substitutions, of residues of the known amino acid sequence of a protein. "Looped" out sequences from deletions or insertions, or mismatches, are considered differences. For example, residues are counted as differences when the humanized immunoglobulin sequence results from a replacement of an amino acid residue in the acceptor immunoglobulin by another residue, e.g., a replacement of an amino acid in the acceptor for the corresponding donor residue or a more typical residue. No differences are counted when the acceptor and donor sequences have the same residue at the corresponding position.

The term "from" when used to refer to a region or sequence (e.g., a variable region or DNA cassette insert sequence) from a donor refers to synthetic, as well as recombinantly-produced sequences. The term "from" refers to biological origin or sequence relatedness.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

As used herein, a more "typical" amino acid residue in an immunoglobulin refers to a residue that occurs in more than about 50% of the sequences in a representative databank. An "unusual" or "rare" amino acid residue occurs less than about 20%, typically less than 10% of the sequences. When deciding whether an amino acid in an acceptor, e.g., a human acceptor, is "rare" or "typical" among acceptor, e.g., human sequences, it is preferable to consider only those sequences present in the same subgroup as the acceptor sequence (see Kabat et al. supra).

The sequences of heavy and light chain constant region genes are known in the art. Preferably, the constant region is human, but constant regions from other species, e.g., rodent (e.g., mouse or rat), primate (macaque), camel, rabbit can also be used. Constant regions from these species are known in the art (see e.g., Kabat, E. A., et al. (1991) *Sequences of Proteins of Immunological Interest, Fifth Edition,* U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 constant region. For an Fab fragment heavy chain gene, the VH-encoding DNA can be operatively linked to another DNA molecule encoding only the heavy chain CH1 constant region.

In one aspect, an isolated immunoglobulin DNA cassette nucleic acid comprises a heavy chain variable leader nucleotide sequence linked to a heavy chain constant region nucleotide sequence, as depicted in FIG. 2. A heavy chain variable leader sequence can be prepared from genomic sequences using the methods described herein (see, e.g., examples). In one embodiment, heavy chain leader sequences include sequences having nucleotide sequences shown in SEQ ID NO:1, or a sequence at least 85%, 90%, 95%, 99% or higher identical thereto. A heavy chain constant region can be prepared from genomic sequences using the methods described herein (see, e.g., Examples). Heavy chain constant region nucleotide sequences can include sequences having nucleotide sequences shown in SEQ ID NOS: 7, 15, 21, or a sequence at least 85%, 90%, 95%, 99% or higher identical thereto. In another embodiment, the isolated immunoglobulin DNA cassette nucleic acid encodes heavy chain leader amino acid sequence linked to a heavy chain constant region amino acid sequence(depicted in FIG. 2). Heavy chain leader amino acid sequences can include sequences having a amino acid sequence as shown in SEQ ID NO: 2, or a sequence at least 85%, 90%, 95%, 99% or higher identical thereto. A heavy chain constant region amino acid sequence can include sequences having an amino acid sequence as shown in SEQ ID NO: 8, 16, 22, or a sequence at least 85%, 90%, 95% or higher identical thereto.

In another embodiment, a heavy chain constant region can be prepared from sequences using the methods described herein (see, e.g., examples), wherein the constant region has an FcR mutation which modulates effector function. Heavy chain constant region nucleotide sequences can include sequences having nucleotide sequences shown in SEQ ID NOS: 9, 17, 23, or a sequence at least 85%, 90%, 95%, 99% or higher identical thereto. Another embodiment includes heavy chain constant regions wherein the sequence has an FcR mutation which modulates effector function. Heavy chain constant region amino acid sequence can include sequences having an FcR mutation wherein the constant regions comprises an amino acid sequence as shown in SEQ ID NO: 10, 18, 24, or a sequence at least 85%, 90%, 95%, 99% or higher identical thereto.

In an additional aspect, an isolated immunoglobulin DNA cassette nucleic acid comprises a kappa light chain variable leader sequence linked to a kappa light chain constant region sequence as depicted in FIG. 2. A kappa chain variable leader nucleotide equence can be prepared from genomic sequences using the methods described herein (see, e.g., examples). In one embodiment kappa chain leader nucleotide sequence can include a nucleotide sequence as shown in SEQ ID NO: 3 or a sequence at least 85%, 90%, 95%, 99% or higher identical thereto. A kappa chain constant region can be prepared from genomic sequences using the methods described herein (see, e.g., examples). In an additional embodiment, kappa chain constant region nucleotide sequences can include sequences having nucleotide sequences shown in SEQ ID NOS: 11, 19, 25, or a sequence at least 85%, 90%, 95%, 99% or higher identical thereto. In another additional embodiment, the isolated immunoglobulin DNA cassette nucleic acid encodes kappa light chain leader amino acid sequence linked to a kappa chain constant region amino acid sequence as depicted in FIG. 2. In preferred embodiments, kappa chain leader amino acid sequence can include amino acid sequences a shown in SEQ ID NO: 4, or a sequence at least 85%, 90%, 95%, 99% or higher identical thereto. Kappa chain constant region amino acid sequences can include sequences having nucleotide sequences shown in SEQ ID NOS: 12, 20, 26, or a sequence at least 85%, 90%, 95%, 99% or higher identical thereto.

In a further aspect, an isolated immunoglobulin DNA cassette nucleic acid comprises a lambda light chain variable leader nucleotide sequence linked to a lambda light chain constant region nucleotide sequence as depicted in FIG. 2. A lambda chain variable leader sequence can be prepared from genomic sequences using the methods described herein (see, e.g., examples). In one embodiment, lambda chain leader sequences include sequences having nucleotide sequences shown in SEQ ID NO:5, or a sequence at least 85%, 90%, 95%, 99% or higher identical thereto. A lambda chain constant region can be prepared from genomic sequences using the methods described herein (see, e.g., examples). Lambda chain constant region nucleotide sequences can include sequences having nucleotide sequences shown in SEQ ID NO: 13, or a sequence at least 85%, 90%, 95%, 99% or higher identical thereto. In another embodiment, the isolated immunoglobulin DNA cassette nucleic acid encodes lambda chain leader amino acid sequence linked to a lambda chain constant region amino acid sequence (depicted in FIG. 2). Lambda chain leader amino acid sequences can include sequences having a amino acid sequence as shown in SEQ ID NO: 6, or a sequence at least 85%, 90%, 95%, 99% or higher identical thereto. A lambda chain constant region amino acid sequence can include-sequences having an amino acid sequence as shown in SEQ ID NO: 14, or a sequence at least 85%, 90%, 95%, 99% or higher identical thereto.

The nucleic acid can encode an antibody light or heavy chain constant region, operatively linked to the corresponding leader sequence. The light chain constant region may be a kappa or lambda chain constant region. Preferably, the light chain constant region is from a lambda type (e.g., a human type lambda). In another embodiment, the heavy chain constant region of an antibody isotype selected from the group consisting of IgG (e.g., IgG1, IgG2, IgG3, IgG4), IgM, IgA1, IgA2, IgD, and IgE. Preferably, the heavy chain constant region is from an IgG (e.g., an IgG1) isotype.

Additional aspects of the invention include assembled immunoglobulin DNA cassette sequences. Assembled immunoglobulin cassette sequences include nucleotide sequences as well as amino acid sequences encoded by an immunoglobulin DNA cassette nucleotide sequence (depicted in FIG. 2). Preferred sequences of the immunoglobulin cassettes include sequences shown in SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, or a sequence at least 85%, 90%, 95%, 99% or higher identical thereto.

Additional embodiments of the invention provide isolated immunoglobulin DNA cassette insert nucleic acid sequences. The insert sequences include nucleic acid sequences comprising a heavy chain variable nucleotide sequence, a lambda light chain variable nucleotide sequence and/or a kappa chain variable nucleotide sequence. Insert sequences can be prepared using the methods of the present invention (see examples). Exemplary insert sequences include those having a nucleotide sequence selected from any one of the sequences as shown in SEQ ID NO:83, 85, 87, or a sequence at least 85%, 90%, 95%, 99% or higher identical thereto. In still another embodiment, the isolated immunoglobulin DNA cassette insert nucleic acid encodes a variable domain selected from a heavy chain variable domain, a lambda light chain, and/or a kappa chain variable amino acid sequence. Exemplary insert amino acid sequences include those having an amino acid sequence selected from any one of the sequences as shown in SEQ ID NO: 84, 86, 88, or a sequence at least 85%, 90%, 95%, 99% or higher identical thereto.

Nucleic acids of the invention can be chosen for having codons, which are preferred, or non preferred, for a particular expression system. E.g., the nucleic acid can be one in which at least one codon, at preferably at least 10%, or 20% of the codons has been altered such that the sequence is optimized for expression in E. coli, yeast, insect, or mammalian cells.

In a preferred embodiment, the nucleic acid differs (e.g., differs by substitution, insertion, or deletion) from that of the sequences provided, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences. The differences are, preferably, differences or changes at nucleotides encoding a non-essential residue(s) or a conservative substitution(s).

In one embodiment, a first and second immunoglobulin DNA cassette nucleic acids are linked, e.g., contained in the same vector. In other embodiments, a first and a second immunoglobulin DNA cassette nucleic acids are unlinked, e.g., contained in a different vector.

In another aspect, the invention features host cells and vectors (e.g., recombinant expression vectors) containing the immunoglobulin DNA cassette nucleic acids of the invention. An additionally provided aspect includes vectors containing the immunoglobulin DNA cassette nucleic acids and containing the DNA cassette insert nucleic acids.

Preferred vectors of the invention include plasmid vectors. An additional preferred vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. It will be appreciated by those skilled in the art that the design of the expression vector, including the selection of regulatory sequences may depend on such factors as the choice of the host cell to be transformed, the level of expression of protein desired, etc.

A host cell can be any cell useful with the constructs of the present invention and include, but are not limited to prokaryotic cells, e.g., bacterial cells such as $E.\ coli$, or eukaryotic cells, e.g., insect cells, yeast, or preferably mammalian cells (e.g., cultured cell or a cellline such as CHO or COS cells for example). A cell line which is transformed to produce the antibody of altered effector function can be an immortalized mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof. Other suitable host cells are known to those skilled in the art.

The recombinant expression vectors of the invention can be designed for expression of the antibodies, or antigen-binding fragments thereof, in prokaryotic or eukaryotic cells. For example, polypeptides of the invention can be expressed in $E.\ coli$, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Preferred mammalian host cells for expressing the antibodies of the invention include Chinese Hamster Ovary (CHO cells) (including dhfr-CHO cells, described in Urlaub and Chasin, (1980) *Proc. Natl. Acad. Sci. USA* 77:4216–4220, used with a DHFR selectable marker, e.g., as described in R. J. Kaufman and P. A. Sharp (1982) *Mol. Biol.* 159:601–621), lymphocytic cell lines, e.g., NSO myeloma cells and SP2 cells, COS cells, and a cell from a transgenic animal, e.g., e.g., mammary epithelial cell.

Expression of proteins in prokaryotes is most often carried out in $E.\ coli$ with vectors containing constitutive or inducible promoters directing the expression of either fusion or non-fusion proteins. Fusion vectors add a number of amino acids to an antibody encoded therein, often to the constant region of the recombinant antibody, without affecting specificity or antigen recognition of the antibody. Addition of the amino acids of the fusion peptide can add additional function to the antibody, for example as a marker (e.g., epitope tag such as myc- or flag).

In addition to the immunoglobulin DNA cassette nucleic acid sequences and the immunoglobulin DNA cassette insert nucleic acids, the recombinant expression vectors of the invention carry regulatory sequences that are operatively linked and control the expression of the antibody chain genes in a host cell.

Preferred regulatory sequences for mammalian host cell expression include viral elements that direct high levels of protein expression in mammalian cells, such as promoters and/or enhancers derived from FF-1a promoter and BGH poly A, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Patent No. 4,968,615 by Schaffner et al.

In addition to the immunoglobulin DNA cassette sequences, insert sequences, and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634, 665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

In an exemplary system for recombinant expression of antibodies, a recombinant expression vector encoding both the desired antibody heavy chain and the desired antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques well known in the are and described herein are used to prepare the recombinant expression vector, transfect the host cells, select for transformants, culture the host cells and recover the antibody from the culture medium.

Preparation of Immunoglobulin DNA Insert Sequences

The $V_H$ or $V_L$ gene sequences can be cloned for preparation of immunoglobulin DNA cassette insert sequences based on published nucleotide sequences known in the art. Alternatively, as described in more detail below, antibodies (preferably, monoclonal antibodies from differing organisms, e.g., rodent, sheep, human) against a predetermined antigen can be produced using art-recognized methods. Once the antibodies are obtained, the variable regions can be sequenced. The light and heavy chain variable regions can, optionally, be ligated to corresponding constant regions.

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al., 1991, *Biotechniques* 11:152–156). A similar strategy can also been used to amplify human heavy and light chain variable regions from human antibodies (Larrick et al., 1991, *Methods: Companion to Methods in Enzymology* 2:106–110).

In an illustrative embodiment, RNA is isolated from B lymphocytes, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and either of the κ and λ light chains, as well as primers for the signal sequence. Using variable region PCR primers, the variable regions of both heavy and light chains are amplified, each alone or in combination, and ligated into appropriate vectors for further manipulation.

Preferably, isolated nucleic acids of light and heavy chain variable regions are useful as insert sequences for use with immunoglobulin DNA cassette vectors. In a preferred embodiment, amplified variable regions comprising various antigen specificity are useful for insertion in a desired immunoglobulin DNA cassette vector for preparation of a battery of antibodies having desired effector function.

Oligonucleotide primers useful in amplification protocols may be unique or degenerate or incorporate inosine at degenerate positions. Restriction endonuclease recognition sequences may be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. In addition to commercially available kits for generating phage display libraries (e.g., the Pharmacia *Recombinant Phage Antibody System,* catalog no. 27-9400-01; and the Stratagene Sur-fZAP™ phage display kit, catalog no. 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

Once displayed on the surface of a display package (e.g., filamentous phage), the antibody library is screened with the antigen, or peptide fragment thereof, to identify and isolate packages that express an antibody having specificity for the antigen. Nucleic acid encoding the selected antibody can be recovered from the display package (e.g., from the phage genome) and subcloned into other expression vectors by standard recombinant DNA techniques.

The Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence information, by a modeling procedure using previously determined three-dimensional structures from other antibodies obtained from NMR studies or crytallographic data. See for example Bajorath, J. and S. Sheriff, 1996, *Proteins: Struct., Funct., and Genet.* 24 (2), 152–157; Webster, D. M. and A. R. Rees, 1995, "Molecular modeling of antibody-combining sites," in S. Paul, Ed., *Methods in Molecular Biol.* 51, Antibody Engineering Protocols, Humana Press, Totowa, N.J., pp 17–49; and Johnson, G., Wu, T. T. and E. A. Kabat, 1995, "Seqhunt: A program to screen aligned nucleotide and amino acid sequences," in *Methods in Molecular Biol.* 51, op. cit., pp 1–15.

An antigen binding region can also be obtained by screening various types of combinatorial libraries with a desired binding activity, and to identify the active species, by methods that have been described.

An antigen binding region can also be obtained through use of a known nucleic acid sequence encoding an immunoglobulin molecule or fragment thereof, having a desired antigen specificity.

Additionally, a series of mutations in known variable region sequences can be made rapidly using mutation methods known to those of skill in the art. Resultant sequences may then be assembled in conjunction with the immunoglobulin DNA cassettes and methods described herein to create a panel of antibodies with different antigen specificities. Determination of the clones harboring the variable region having the desired specific binding characteristic can be rapidly generated.

Once a nucleic acid encoding the preferred antigen specificity is identified, variable domain insert sequences may be isolated for use in the immunoglobulin DNA cassettes of the present invention in order for preparation of antibodies having particular antigen specificity, while specifying effector function through use of the desired immunoglobulin DNA cassette.

An additionally preferred use of the isolated nucleic acid encoding a preferred antigen specificity is in preparation of a battery of antibodies having a singly preferred antigen specificity, with variable effector functions. In preparation of a battery of antibodies, for example, various DNA expression vectors comprising heavy and light chain immunoglobulin DNA cassettes having various effector functions are provided, wherein the effector functions desired for the battery of antibodies are sufficiently represented among the immunoglobulin DNA cassettes (e.g., IgG, IgM, IgA, IgD and IgE). In preparation of the battery of antibodies, isolated variable region heavy and light chain DNA insert sequences are incorporated into DNA expression vectors comprising the variable effector functions. Resultant expression vectors encoding immunoglobulins can then be transfected into host cells for expression of antibodies. Resulting expression will yield a battery of antibodies with variable effector function, while maintaining the desired antigen specificity.

Methods of Producing Antibody Molecules

In another aspect, the invention features a method of providing an antibody preparation having improved assembly characteristics over compositions presently used in the art, the method comprising: providing a first nucleic acid, e.g., an immunoglobulin DNA cassette nucleic acid encoding immunoglobulin heavy chain (or a fragment thereof, e.g., the heavy chain variable region) as described herein; providing a second immunoglobulin DNA cassette nucleic acid encoding immunoglobulin light chain (or a fragment thereof, e.g., the light chain variable region); and introducing said first and second nucleic acids into a host cell, e.g., a host cell as described herein, under conditions that allow expression and assembly of said light and heavy chain immunoglobulins, resulting in antibody production.

An antibody molecule of the invention can be prepared by recombinant expression of immunoglobulin light and heavy chain genes in a host cell. To express an antibody recombinantly, a host cell is transfected with one or more recombinant expression vectors carrying nucleic acid fragments encoding the immunoglobulin light and heavy chains of the antibody such that the light and heavy chains are expressed in the host cell and, preferably, secreted into the medium in which the host cells are cultured, from which medium the antibodies can be recovered. Methodologies as described herein are used produce antibody heavy and light chain genes, incorporate these genes operatively linked to leader sequences into recombinant expression vectors and introduce the vectors into host cells, such as those described in Sambrook, Fritsch and Maniatis (eds), *Molecular Cloning; A Laboratory Manual, Second Edition,* Cold Spring Harbor, N.Y., (1989), Ausubel, F. M. et al. (eds.) *Current Protocols in Molecular Biology,* Greene Publishing Associates, (1989) and in U.S. Pat. No. 4,816,397 by Boss et al.

Subconfluent monolayers of dhfr-Chinese Hamster Ovary cells can be co-transfected with the vector containing the heavy chain gene and a second vector containing the humanized light chain. Alternatively, the heavy and light chain genes can be cloned into a single vector. Prior to transfection, the plasmid DNA(s) can be linearized using the appropriate restriction endonuclease.

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble, and secrete a properly folded and immunologically active antibody. Prokaryotic expression of antibody genes has been reported to be ineffective for production of high yields of active antibody (Boss, M. A. and Wood, C. R. (1985) *Immunology Today* 6:12–13).

Heavy and light chain transfectants can be selected for in xanthine/hypoxanthine free IMDM containing 5%(v/v)dialyzed fetal calf serum.

When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Use of the methods described herein for preparation and production of antibodies has been shown to result in production to levels of about ten times greater than presently preferred methods of antibody production. Without being limited by mechanism, it is possible that the use of cDNA (versus genomic DNA) assists in the rapid production of mature RNA. Additionally, incorporation of leader sequences may facilitate expression and/or production of antibody. Finally, incorporation of both heavy and light chain immunoglobulin gene sequences in a single expression vector may facilitate coordinated expression levels and production of proteins for facilitated assembly characteristics.

Host cells can also be used to produce portions of intact antibodies, such as Fab fragments. It will be understood that variations on the above procedure are within the scope of the present invention. For example, it may be desirable to transfect a host cell with DNA encoding either the light chain or the heavy chain (but not both) of an antibody of this invention. Methods described herein may also be used to remove some or all of the DNA encoding either or both of the light and heavy chains that is not necessary for binding to a predetermined antigen, e.g., CD3. The molecules expressed from such truncated DNA molecules are also encompassed by the antibodies of the invention. In addition, bifunctional antibodies may be produced in which one heavy and one light chain are an antibody of the invention having a predetermined antigen specificity and the other heavy and light chain are specific for an antigen other than the predetermined antigen, e.g., by crosslinking an antibody of the invention having a predetermined specificity to a second antibody by standard chemical crosslinking methods.

Uses of the Antibody Production and Conversion System

Production of chimeric antibodies, including chimeric immunoglobulin chains, can be facilitated by use of techniques known in the art used in conjunction with the compositions and methods described herein. Constant regions from different species may be used. An expression vector can be generated in which a chimeric VH gene may be expressed in conjunction with different immunoglobulin heavy chain constant region genes (Gunning s al. (1987) P. N. A. S. USA 85: 7719–7723). For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Patent No. 4,816,567; Cabilly et al., European Patent Application 125, 023; Better et al. (1988 *Science* 240:1041–1043); Liu et al. (1987) *PNAS* 84:3439–3443; Liu et al., 1987, *J. Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J. Natl Cancer Inst.* 80:1553–1559).

An antibody or an immunoglobulin chain can be humanized by methods known in the art. These processes will also be facilitated through use of the compositions and methods comprising the antibody production and conversion system of the present invention. Humanized antibodies, including humanized immunoglobulin chains, can be generated by replacing sequences of the Fv variable region which are not directly involved in antigen binding with equivalent sequences from human Fv variable regions. General methods for generating humanized antibodies are provided by Morrison, S. L., 1985, *Science* 229:1202–1207, by Oi et al., 1986, *BioTechniques* 4:214, and by Queen et al. U.S. Pat. Nos. 5,585,089, 5,693,761 and 5,693,762, the contents of all of which are incorporated herein by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target. The recombinant DNA encoding the humanized antibody, or fragment thereof, can then be cloned into an appropriate expression vector.

Humanized or CDR-grafted antibody molecules or immunoglobulins can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552–525; Verhoeyan et al. 1988 *Science* 239:1534; Beidler et al. 1988 *J. Immunol.* 141:4053–4060; Winter U.S. Pat. No. 5,225,539, the contents of all of which are expressly incorporated herein by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated herein by reference. All of the CDR's of a particular human antibody may be replaced with at least a portion of a non-human CDR or only some of the CDR's may be replaced with non-human CDR's. It is only necessary to replace the number of CDR's required for binding of the humanized antibody to a predetermined antigen.

Also within the scope of the invention are humanized antibodies produced by the methods described herein, including immunoglobulins, in which specific amino acids have been substituted, deleted or added. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the contents of which are hereby incorporated herein by reference. Other techniques for humanizing immunoglobulin chains, including antibodies, are described in Padlan et al. EP 519596 A1, published on Dec. 23, 1992.

Monoclonal, chimeric, hybrid and humanized antibodies, which have been modified by, e.g., deleting, adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation. One skilled in the art will appreciate this is but a representative list of potential modifications.

In one embodiment, the constant region of the antibody can be replaced by another constant region from, e.g., a different species. This replacement can be carried out using molecular biology techniques, and the compositions and methods described herein. For example, the nucleic acid encoding the VL or VH region of an antibody can be converted to a full-length light or heavy chain gene, respectively, by operatively linking the VH or VL-encoding nucleic acid to another nucleic acid encoding the light or heavy chain constant regions using the immunoglobulin DNA cassette vectors described. Preferably, the constant region is human, but constant regions from other species, e.g., rodent (e.g., mouse or rat), primate, camel, rabbit can also be used. Constant regions from these species are known in the art (see e.g., Kabat, E. A., et al. (1991) *Sequences of Proteins of Immunological Interest, Fifth Edition*, U.S. Department of Health and Human Services, NIH Publication No. 91–3242).

Modified antibody molecules may have enhanced therapeutic applications compared to their unmodified counterparts. For example, aglycosylated antibodies which have a modified Fc region, have been shown to be substantially non-mitogenic to T cells, while retaining immunosuppressive properties.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated herein by reference). Similar types of alterations could be described which if applied to the murine, or other species immunoglobulin would reduce or eliminate these functions.

For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821).

In other embodiments, replacing residue 297 (asparagine) with alanine in the IgG constant region significantly inhibits recruitment of effector cells, while only slightly reducing (about three fold weaker) affinity for C1q (see e.g., U.S. Pat. No. 5,624,821). The numbering of the residues in the immunoglobulin chain is that of the EU index (see Kabat et al., 1991). This alteration destroys the glycosylation site and it is believed that the presence of carbohydrate is required for Fc receptor binding. The modification at residue 297 (asparagine to alanine) has been shown to produce aglycosylated anti-CD3 antibodies of the IgG subclass having significantly reduced binding of the antibody Fc region to the Fc receptor. Aglycosylated CD3 antibodies have been shown to be substantially non-mitogenic for human T cells, while being retaining immunosuppressive properties (Bolt, S. et al. (1993) *Eur. J. Immunol.* 23(2):403–11; Routledge, E. G. et al. (1995) *Transplantation* 60(8):847–53; U.S. Pat. Nos. 5,585,097; 5,968,509, the contents of all of which are hereby incorporated herein by reference). When used as human therapeutics, such aglycosylated antibodies show reduced "first dose effect," which is a syndrome experienced by patients following the initial administration of the CD3 antibody. This phenomenon requires the cross-linking of the CD3 antigen on the surface of T-cells to accessory cells through Fc receptors. Aglycosylated anti-CD3 antibodies (and in particular, humanized anti-CD3 antibodies) have been shown to elicit a reduced first dose effect, and thus have been shown to be useful therapeutic agents to treat a variety of immune conditions.

Any other substitutions at this site that destroys the glycosylation site are believed cause a similar decrease in lytic activity. Other amino acids substitutions, e.g., changing any one of residues 318 (Glu), 320 (Lys) and 322 (Lys), to Ala, are also known to abolish C1q binding to the Fc region of IgG antibodies (see e.g., U.S. Pat. No. 5,624,821).

Modified antibodies can be produced which have a reduced interaction with an Fc receptor. For example, it has been shown that in human IgG3, which binds to the human Fc gamma R1 receptor, changing Leu 235 to Glu destroys the interaction, of the mutant for the receptor. Mutations on adjacent or close sites in the hinge link region of an antibody (e.g., replacing residues 234, 236 or 237 by Ala) can also be used to affect the affinity for the Fc gamma RI receptor. Mutations L235A and G237A inhibit the binding of the constant region to human Fc receptors and inhibit the initiation of ADCC reactions, and have been described previously in U.S. Pat. No.: 5,985,279 and International Publication No.: WO98/06248, which are incorporated herein by reference. The numbering of the residues in the immunoglobulin chain is that of the EU index. See Kabat et al., (1991) *J Immunol.* 147:1709–19.

In a preferred embodiment, an immunoglobulin DNA cassette comprises nucleic acid sequences encoding an immunoglobulin resulting in production of an antibody having reduced or no ability to bind an Fc receptor. For example, it is an isotype or subtype, fragment or other mutant, which does not support binding to an Fc receptor, e.g., it has a mutagenized or deleted Fc receptor binding region.

Additional methods for altering the lytic activity of an antibody, for example, by altering one or more amino acids in the N-terminal region of the CH2 domain are described in WO 94/29351 by Morgan et al. and U.S. Pat. No. 5,624,821, the contents of all of which are hereby expressly incorporated herein by reference.

Antibody fragments comprising only a portion of the primary antibody structure can also be produced using the immunoglobulin DNA cassettes and methods of the present invention, which fragments possess one or more immunoglobulin activities (e.g., antigen binding, complement fixation activity). Such polypeptide fragments may be produced by proteolytic cleavage of intact antibodies by methods known in the art, or by inserting stop codons at the desired locations in the vectors using site-directed mutagenesis, such as after CH1 to produce Fab fragments or after the hinge region to produce (Fab')2 fragments. Single chain antibodies may be produced by joining VL and VH with a DNA linker (see, Huston et al. (2001) *Hum Antibodies.* 10:127–42. op. cit.).

Alternatively, the DNA immunoglobulin cassettes may be altered for rapid production of a single chain antibody. Engineering of single-chain antibody (scFV) have been described in, for example, Colcher, D. et al. (1999) *Ann. N Y Acad. Sci.* 880:263–80; and Reiter, Y. (1996) *Clin. Cancer Res.* 2:245–52. A single chain antibody can be dimerized or multimerized to generate multivalent antibodies having specificities for different epitopes of the same target protein.

Accordingly, the immunoglobulin DNA cassette vectors of the present invention are engineered to include a leader sequence operably linked to a minimal variable domain sequence, minimal constant region or modified constant region to allow for incorporation of variable domains of heavy and/or light chains as desired. Furthermore, the heavy and light chain DNA cassettes are operatively linked via a DNA linker, as desired in order to engineer the desired modified antibody construct.

Monobodies, Novel Immunoglobulin Molecules

An antibody has a long sera half-life (up to weeks), however, the large size of antibodies, and the fact that antibodies have two antigen binding sites and can cross-link receptors or cells and activate the cells has spurred the development of smaller molecules, which may be more useful for the development of biotherapeutic agents. As discussed above, single chain antibodies (scFV) or Fab fragments have been developed which cannot cross-link receptors or cells, and thus would not lead to the undesired effects of crosslinking. Additionally, a single antigen-binding region attached to a partial Fc region can be created by mutating the hinge (to prevent the disulfide bonding of two heavy chains). However, without the intact Fc region, these smaller molecules are subject to attack by proteases and have a short sera half-life (hours).

We have developed a monovalent antibody composed of a single antibody heavy chain associated with a single extended antibody light chain, termed herein a "monobody." The extended light chain is composed of a kappa constant region attached to the hinge and CH2-CH3 region of a heavy constant region. A heavy chain monobody protein and an extended light chain monobody protein form a single antigen-binding site with a single Fc region. Attaching the heavy chain Hinge-CH2-CH3 to the kappa constant region should create an "intact" Fc that is protected from digestion and creates a single antigen-binding site.

It was not known if attaching an IgG1 Hinge-CH2-CH3 to the end of a kappa light chain would create too much steric interference to prevent the association of the heavy and light chains or reduce its stability. Thus, two versions of a monobody have thus been proposed and are described herein (see Examples). One embodiment is based on the IgGI antibody which is more rigid but a known therapeutic utility. A second embodiment is based on IgG3 which has greater flexibility due to the position of the disulfide bonding and length of hinge sequences. However, it is intended that the basic structure of the monobody construct is understood in the principles described herein, and the specifics of the Ig type of hinge and/or constant sequences utilized may be tailored to suit the particular situation.

Thus, provided are methods and compositions for construction of nucleic acids comprising immunoglobulin monobody DNA cassettes, as well as vectors comprising monobody cassettes, methods for construction of monobodies having desired affinity for specific antigen. Still further, the monobody DNA cassettes and vectors may be used for production of monobody proteins, similarly to the methods described for antibodies and immunoglobulin molecules utilizing the immunoglobulin DNA cassette sequences and vectors supra.

Figure 11:
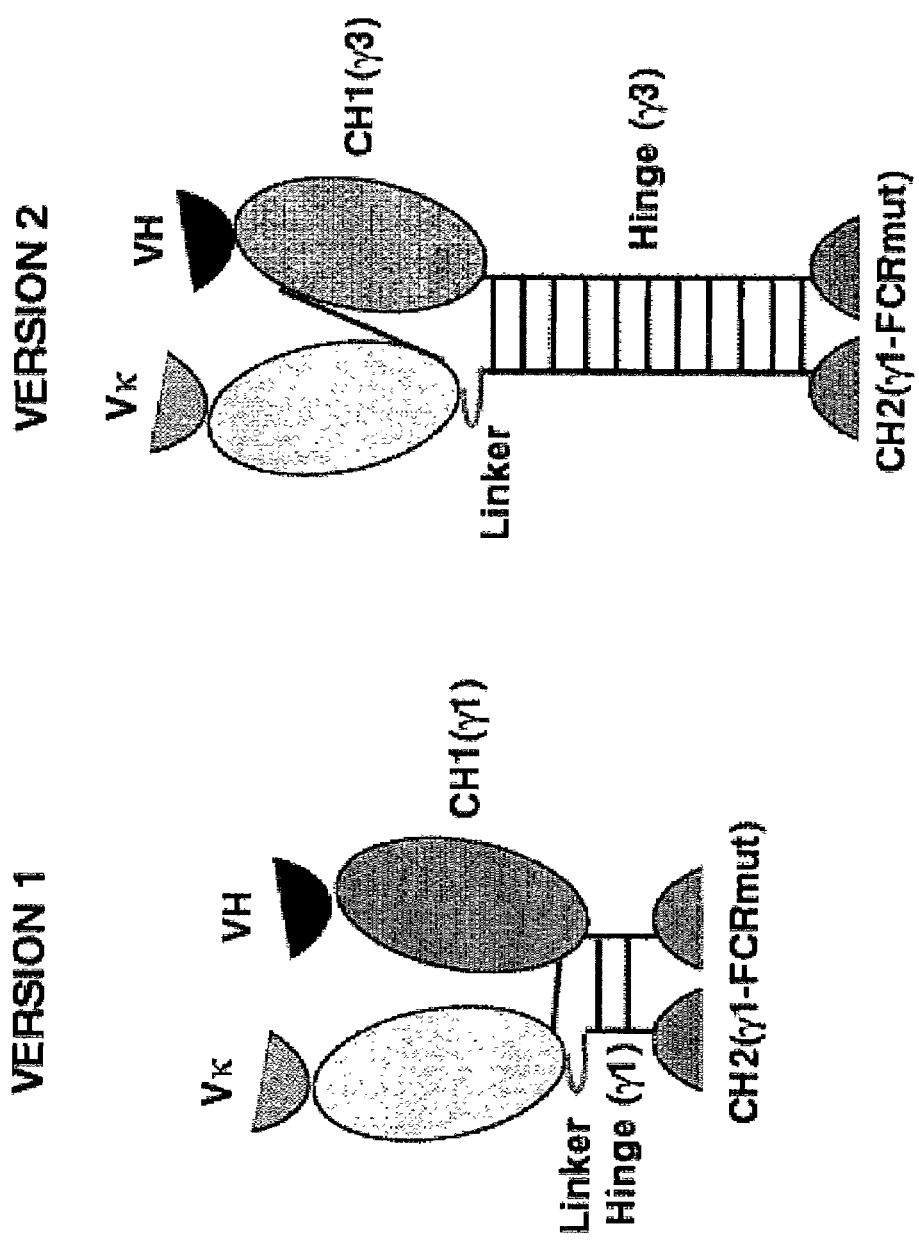
FIG. 11 depicts structural constructs and comparison of hinge regions of proposed monobody constructs.
Figure 12:
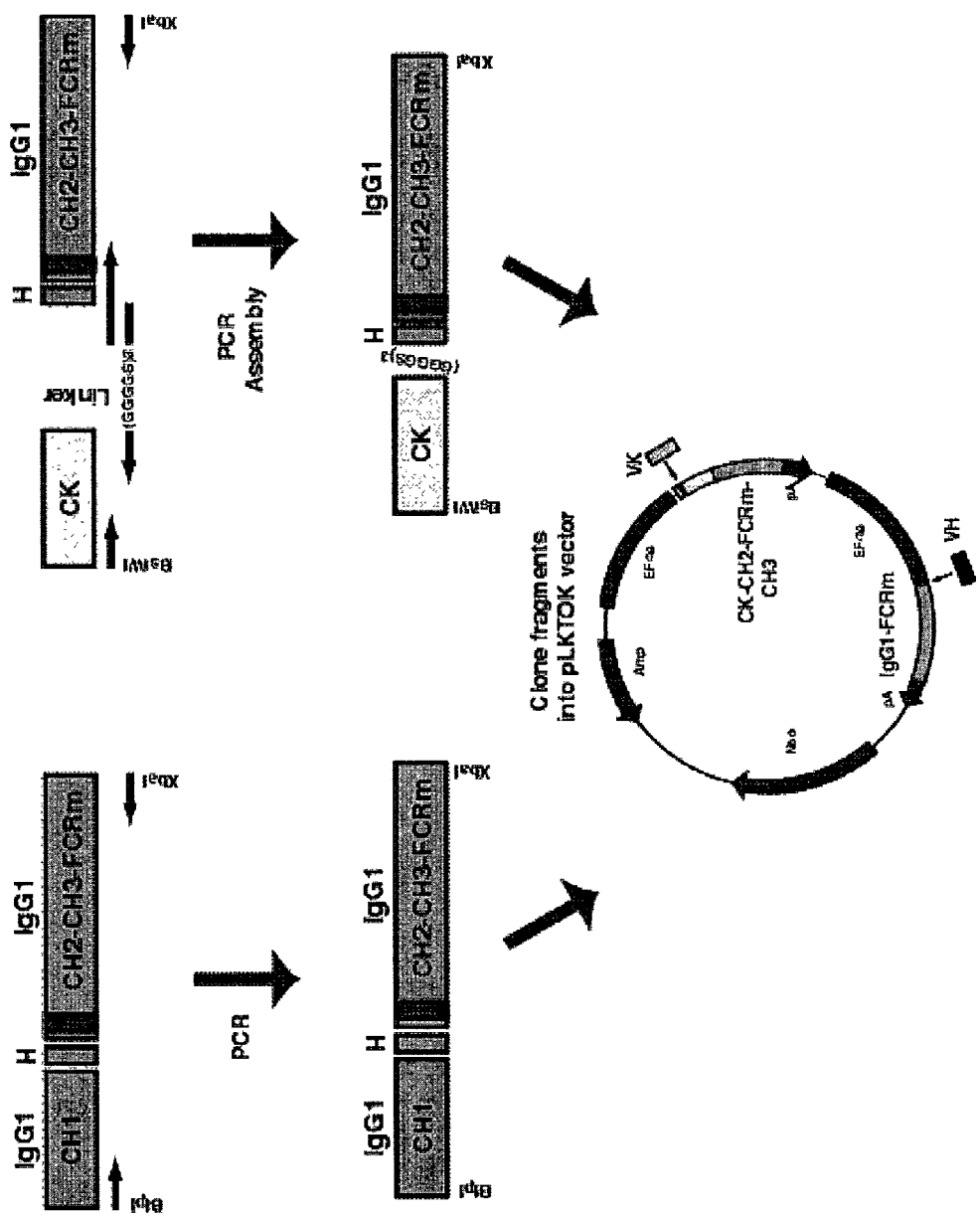
FIG. 12 depicts construction of an antibody heavy chain cassette vector and the cloning process used to combine the nVHL sequence with a heavy chain constant region in a single chain expression vector.

In one aspect, an isolated immunoglobulin monobody DNA cassette nucleic acid comprises a heavy chain variable leader nucleotide sequence linked to a heavy chain constant region nucleotide sequence, wherein the constant region has an FcR mutation which modulates effector function, as depicted in FIG. 11 or 12. A heavy chain variable leader and/or constant region sequences can be prepared from genomic sequences using the methods described herein (see, e.g., Examples.) In another embodiment, the isolated monobody immunoglobulin DNA cassette nucleic acid encodes heavy chain leader amino acid sequence linked to an IgG3 CH1 and hinge regions and an IgG1 heavy chain CH2 and CH3 constant region amino acid sequence (depicted in FIG. 11 and FIG. 13). Monobody heavy chain cassette nucleotide sequences can include sequences having nucleotide sequences shown in SEQ ID NOS: 69, 105, or a sequence at least 85%, 90%, 95%, 99% or higher identical thereto. Heavy chain monobody amino acid sequences can include sequences having a amino acid sequence as shown in SEQ ID NO: 70, 106, or a sequence at least 85%, 90%, 95%, 99% or higher identical thereto.

In an additional aspect, an isolated immunoglobulin DNA cassette nucleic acid comprises an extended monobody light chain comprising a light chain variable leader sequence linked to a light chain constant region sequence further linked to an IgG1 hinge and an IgG1 CH2 and CH3 constant region as depicted in FIG. 11 and FIG. 12. A light chain variable leader and/or constant region nucleotide sequence can be prepared from genomic sequences using the methods described herein (see, e.g., Examples). In a preferred embodiment, an extended monobody light chain cassette nucleotide sequences can include sequences having nucleotide sequences shown in SEQ ID NO: 107 or a sequence at least 85%, 90%, 95%, 99% or higher identical thereto.

Figure 13:
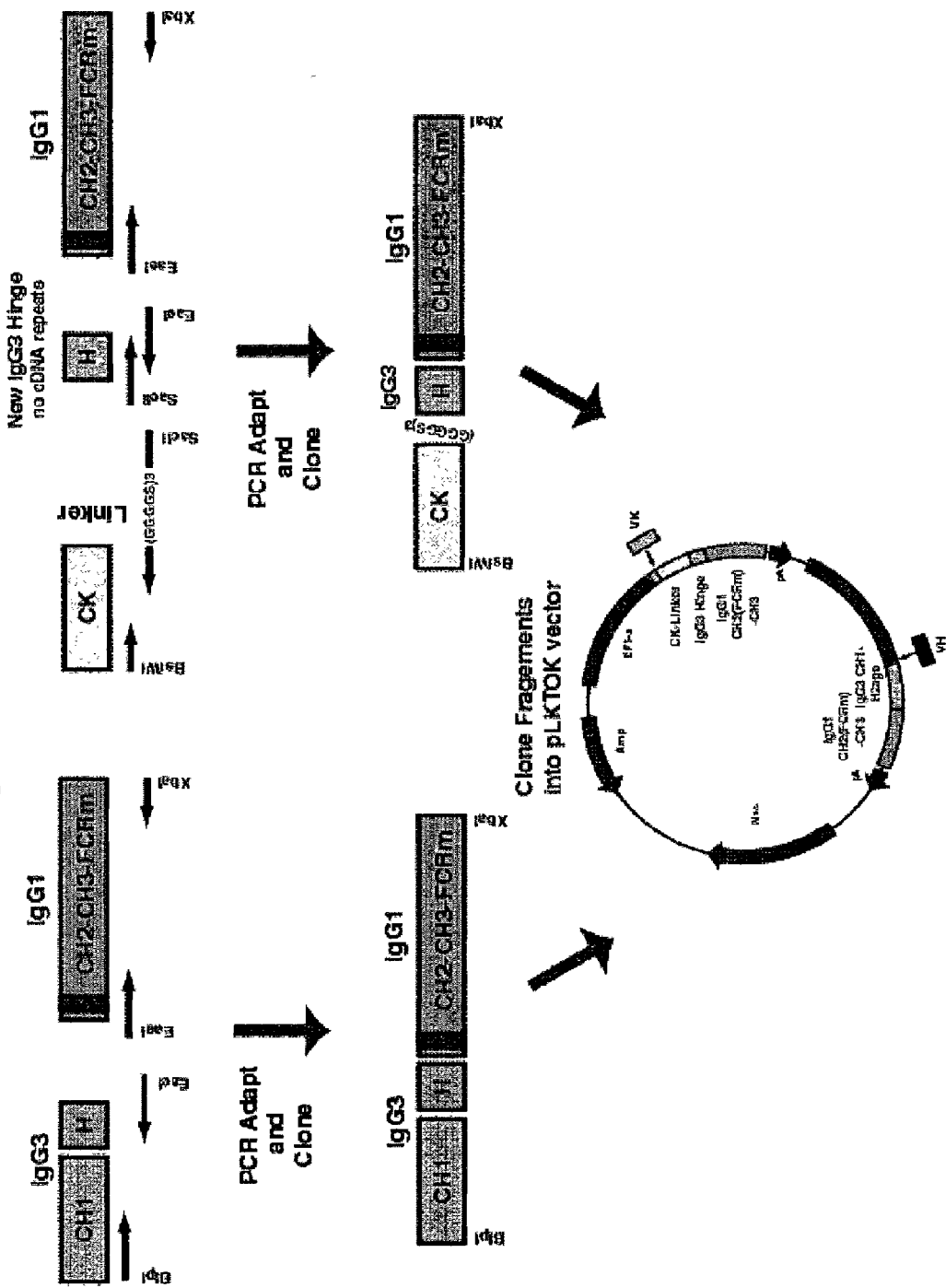
FIG. 13 depicts construction of an antibody heavy chain cassette vector and the cloning process used to combine the nVHL sequence with a heavy chain constant region in a single chain expression vector.

In another embodiment, the isolated immunoglobulin monobody DNA cassette nucleic acid encodes a monobody light chain leader amino acid sequence linked to a light chain constant region further linked to an IgG3 hinge and an IgGICH2 and CH3 region as depicted in FIG. 11 and FIG. 13. A light chain variable leader and/or constant region nucleotide sequence can be prepared from genomic sequences using methods described herein (see Examples). In one embodiment, an extended monobody light chain cassette nucleotide sequence can include sequences having sequences shown in SEQ ID NO: 109, or a sequence at least 85%, 90%, 95%, 99% or higher identical thereto. Monobody amino acid sequence include constructs as depicted in FIG. 11 and FIG. 13. Monobody extended light chain amino acid cassette sequences can include sequences having nucleotide sequences shown in SEQ ID NOS: 108, 110, or a sequence at least 85%, 90%, 95%, 99% or higher identical thereto.

The nucleic acid can encode a monobody light or heavy chain constant region, operatively linked to the corresponding leader sequence. The light chain constant region may be a kappa or lambda chain constant region. Preferably, the light chain constant region is from a kappa type (e.g., a human type kappa). In another embodiment, the heavy chain constant region of an antibody isotype selected from the group consisting of IgG (e.g., IgG1, IgG2, IgG3, IgG4), IgM, IgA1, IgA2, IgD, and IgE. Preferably, the heavy chain constant region is from an IgG (e.g., an IgG1 or IgG3) isotype.

Additional aspects of the invention include assembled immunoglobulin monobody DNA cassette vector sequences. Assembled immunoglobulin cassette vector sequences include nucleotide sequences as well as amino acid sequences encoded by an immunoglobulin DNA cassette nucleotide sequence (depicted in FIGS. 12 and 13). Preferred sequences of the immunoglobulin monobody cassettes include sequences shown in SEQ ID NO: 69, SEQ ID NO: 70, SEQ ID NO: 105, SEQ ID NO: 106, SEQ ID NO: 107, SEQ ID NO: 108, SEQ ID NO: 109, SEQ ID NO: 110, or a sequence at least 85%, 90%, 95%, 99% or higher identical thereto. Preferably, monobody vectors comprise one heavy chain monobody cassette and one extended light chain monobody cassette.

Expression of monobodies can be attained according to the methods described above for immunoglobulin DNA cassettes. Because the cassettes can be prepared with desired cloning sequences for insertion of variable domain sequences, insertion of variable domains, followed by transfection of cells and production of proteins can be carried out in the manner described herein, or other suitable methods known in the art. For specific examples of preparation and production of monobodies, see Examples section below.

An immunoglobulin molecule (e.g., antibody or monobody) can be derivatized or linked to another functional molecule (e.g., another peptide or protein). Accordingly, the antibodies and antibody portions or otherwise modified forms of the antibodies of the invention described herein, may be further derivatized for use in research, diagnostic and/or therapeutic contexts. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Exemplary fluorescent detectable agents include fluorescein, fluorescein isothiocyanate, rhodamine, 5-dimethylamine-l-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prostetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, though the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, γ-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The present invention is further illustrated by the following experimental procedures and examples, which are provided to aid the understanding of the invention, and should not be construed as a limitation thereof.

EXPERIMENTAL

Generation of Immunoglobulin DNA Cassette Constructs

Cassettes were constructed to contain immunoglobulin leaders (signal sequences) and constant regions separated by cloning sites and linkers. The organization of the cloning sites allows the addition of any variable regions to create intact cDNA. Each complete vector also contains both the heavy and the light chains each driven by its own promoter with its own polyadenylation region.

EXAMPLE 1

Creation of Leader Sequences

The VH heavy chain leader (nVHL) was created by reverse translation of human and mouse VH signal sequence available in the public database to determine those with the potential to have useful restriction enzyme cloning sites added within the signal sequence. The sequence chosen for the VH leader comes from the mouse gene U60820 which has been described previously (See Mus musculus anti-digoxin immunoglobulin heavy chain variable region precursor mRNA, partial cds. Genbank Submission (13 Jun. 1996) Mironova, R. S., et al.; Gene activity regulation, Inst. Molecular Biology, Bulgarian Academy of Sciences, Acad G.Bonchev bl 21, Sofia 1113, Bulgaria.)

U60820 (SEQ ID NO: 101): MAVLGLLFCLVTLP-NCVLS

DNA sequences were designed that would encode both the original protein sequence and the desired unique restriction cloning site, MfeI, flanked by an EcoRI restriction enzyme site and a Kozak sequence on the 5' end. At its 3' end a stuffer sequence was followed by the sequence for the 5' end of the human IgG1 region containing a BlpI restriction enzyme site, to generate the following amino acid sequence (stuffer sequences shown in lower case):

nVHL (SEQ ID NO 2): MAVLGLLFCLVTLPNCVLSr-lvtvssas.

DNA (SEQ ID NO: 1) was then created by combining the following two primers, primer V/BLa and primer VHLb (Table 1), and amplifying with Taq polymerase in a reaction 94° C. for 2 minutes followed by of 20 cycles of 94° C. for 2 minutes and 72° C. for 2.5 minutes with 30 second ramping and finishing with 72° C. for 10 minutes. The two primers contain 24 overlapping bases of complementary sequence. The resulting PCR product was TA cloned and individual clones sequenced to select for the clone with the desired sequence. This complete fragment encodes the protein shown in SEQ ID NO: 2.

The VK leader (nVKL) was constructed by reverse translating human and mouse kappa chain signal sequences to determine those with the potential to have useful restriction enzyme cloning sites added. The sequence utilized, the VK leader of human VK1-L5, has been previously described (see Pech M, et al. Organization and evolution of a gene cluster for human immunoglobulin variable regions of the kappa type. 1984. J Mol Biol 176(2):189–204.)

VK1-L5 (SEQ ID NO: 102): MDMRVPAQLLGLLLL-WEPGSRS

The DNA sequence was designed that would encode both the original protein sequence and the desired unique restriction cloning site, PpuMI, flanked by an NotI restriction enzyme site and a Kozak sequence on the 5' end. At its 3' end it had a stuffer sequence followed by the sequence for the 5' end of the human C Kappa region containing the BsiWI restriction enzyme site, to generate the following amino acid sequence (stuffer sequences shown in lower case):

nVKL (SEQ ID NO: 4): MDMRVPAQLLGLLLLWFPG-SRSswrskrtv.

All leader sequences contained restriction enzyme sites within their own coding sequences. Other leaders were used during the development of the vectors that were not as useful because they contained the restriction enzyme sites within the VH and VK genes (thus contained the first few bases of the VH and VK genes). In these, DNA that included the restriction enzyme sites EcoRI, ClaI and XhoI along with a Kozak sequence were incorporated at the 5' end of the leader sequences. Although such constructs can be used for some variable regions, they are not necessarily suitable for all.

second expression vector that contains a light chain cassette to create the complete expression vector to which any variable regions can be added.

The human heavy chain constant region human IgG1-FCRmut, was constructed by PCR assembly to add the mutations L235A and G237A to human IgG1 (primers shown in Table 2).

PCR assembly is a series of three PCR reaction with the end result being rapid site-directed mutagenisis (a simplified method of procedure is described in Bendig, M. M. and Jones, S. T., Rodent to human antibodies by CDR grafting (pgs 161–164) in Antibody Engineering. Eds J. McCafferty, H. R. Hoogenboom and D. J. Chiswell; IRL Press, Oxford, U.K. 1996, which is incorporated herein by reference). The first reaction was a standard 30 cycle PCR to produce two fragments with the primers pCHhum1 to pCHhum3 (section 1) and pCHhum4 to pCHhum2 (section 2). The two fragments were gel purified and combined in equal molar ratios for assembly through 8 cycles of 94° C. for 1.5 min and 72° C. for 2.5 min with a 30 second ramping time between each. The material from this reaction was used as a template to amplify the combined cDNA using the primers pCHhum1 and pCHhum2. The primers pCHhum3 and pCHhum4 contain 24 overlapping bases of complementary sequence and the DNA sequences for the mutated protein. As before

TABLE 1 uz,6/38 Primers used to create VH and VK leader sequences.

| PRIMER | SEQUENCE | |
|---|---|---|
| pVHLa | 5'CCGAATTCCTCACCATGGCTGTCTTGGGGCTGCTCTTCTGCCTGGTG ACTTTACCCAATTG 3' | SEQ ID NO: 27 |
| pVHLb | 5'TGGAGGCTGAGCTGACTGTGACTAGTCTGGACAGGACACAATTGGG TAAAGTCACCAGGCAG 3' | SEQ ID NO: 28 |
| pVKLa | 5'ATATGCGGCCGCCTCACCATGGACATGAGGGTGCCCGCGCAGCTCC TGGGGCTGCTGCTGCTCTGGTTCC 3' | SEQ ID NO: 29 |
| pVKLb | 5'GCCACCGTACGCTTTGATCTCCAGCTGGAACGGGACCCTGGGAACC AGAGCAGCAGCAGCCCCAG 3' | SEQ ID NO: 30 |
| pVLLa5 | 5'ATATGCGGCCGCCTCACCATG 3' | SEQ ID NO: 31 |
| pVLLa3 | 5'ACCTAGGACGGTTAACTTTGATCTCCAGCTGGAAC 3' | SEQ ID NO: 32 |

EXAMPLE 2

Creation of Human Cassettes

The human heavy chain constant region, human IgG1-WT, was constructed by a standard PCR reaction of human splenic cDNA (Invitrogen) with the primers pCHhum1 and pCHhum2 (Table 2). The primer pCHhum1 contains the cloning site BlpI within its 5' sequence and the primer pCHhum2 contains a stop codon followed by the cloning site XbaI. Utilization of these primers resulted in generation of the human constant region sequences shown in SEQ ID NO:7 & 8.

Figure 3:
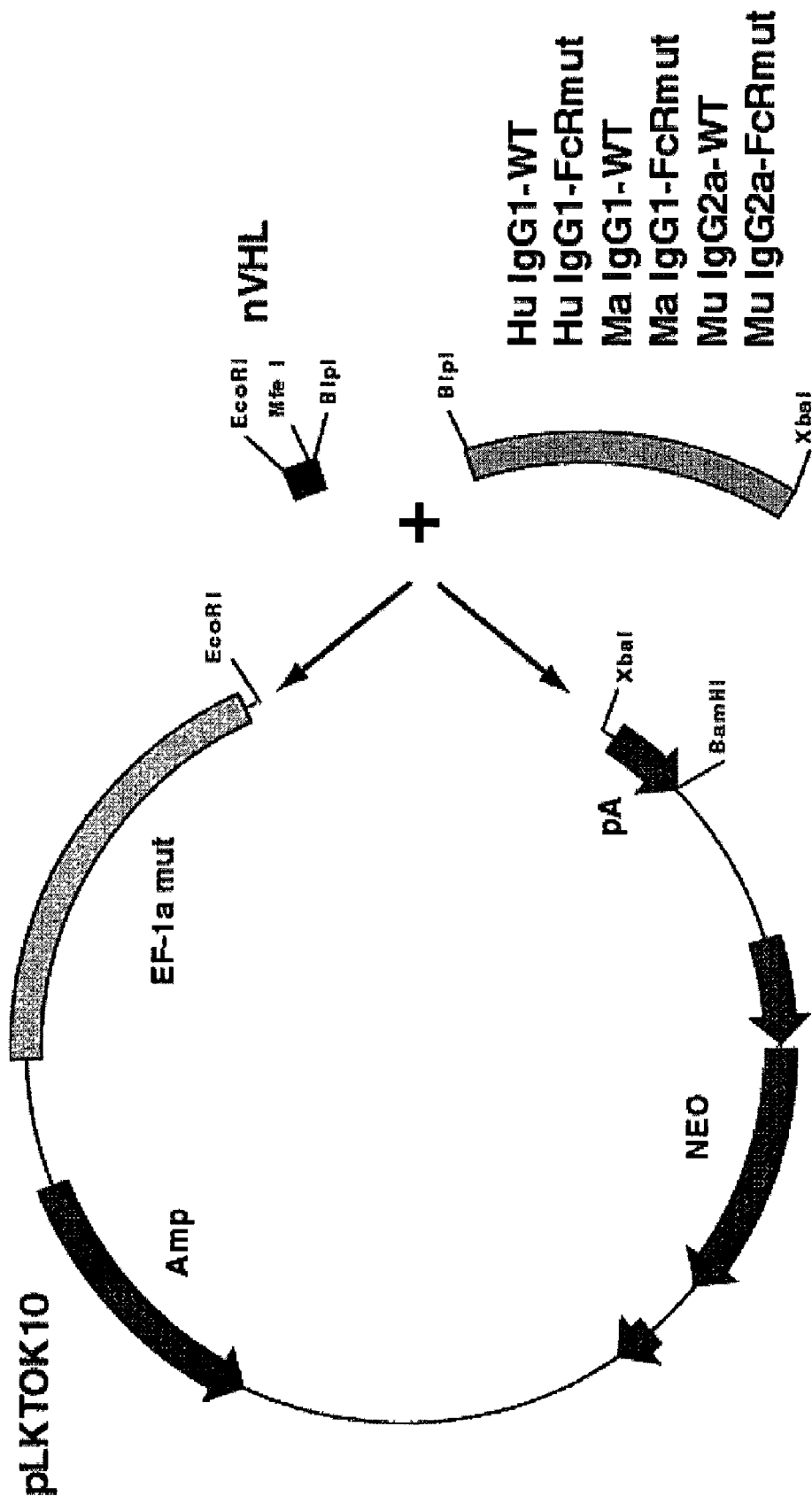
FIG. 3 depicts construction of an antibody heavy chain cassette vector and the cloning process used to combine the nVHL sequence with a heavy chain constant region in a single chain expression vector.

The human IgG1-WT cassette, named pLKTOK55, was then created by cloning the nVHL fragment together with the IgG1 fragment into the expression vector pLKTOK10 which contains an EF-1a promoter and a BGH polyadenylation region flanking the cloning site (FIG. 3). This method was used to create all the described heavy chain cassettes.

The entire region of promoter through polyadenylation region is flanked with BglII and BamHI restriction enzyme sites. This allows the entire cassette to be transferred to a pCHhum1 contains BlpI and pCHhum2 contains XbaI. The amplified fragment was TA cloned and sequenced to select for the desired clone. The resulting DNA and encoded amino acid sequences are shown in SEQ ID NOs: 9 & 10.

Cloning the nVHL fragment together with the IgG1 fragment into the expression vector pLKTOK10 then created the human IgG1-FcRmut cassette named pLKTOK56 (FIG. 3).

The human kappa constant region was created by standard PCR amplification of human cDNA with the primers pCK1 and pCK2 (Table 2). The 5' primer pCK1 contains the sequence for the BsiWI cloning site and the 3' primer pCK2 contains the XbaI cloning site flanking the stop codon.

This was followed by silent mutation of the sequence encoding the BlpI restriction enzyme at position 180 by site directed mutagenesis using the primer pCK4 and the Transformer Site-Directed Mutagenesis Kit produced by CloneTech (Palo Alto, Calif.). This BlpI site would interfere with the cloning of the VH gene into the heavy chain cassette. Resulting sequences are depicted in SEQ ID NOS: 11 and 12.

Figure 4:
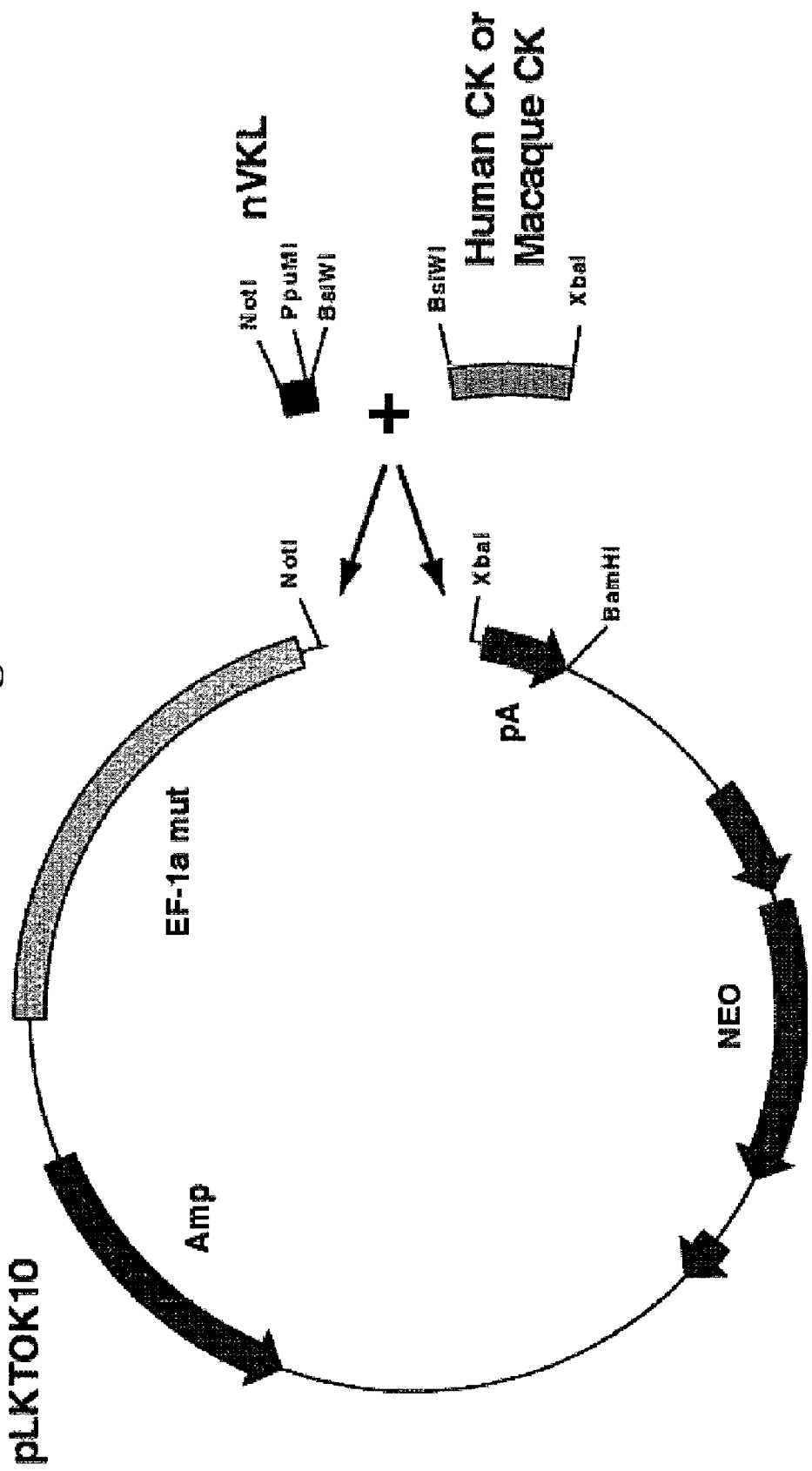
FIG. 4 depicts construction of an antibody kappa chain cassette vector and the cloning process used to combine the nVKL sequence with a CKappa light chain constant regions in a single chain expression vector.

Cloning the nVKL fragment together with the CKappa fragment into the expression vector pLKTOK10 then created the human C Kappa cassette, named pLKTOK57 (FIG. 4). This method was used to create all the described human and macaque kappa light chain cassettes.

The human lambda cassette was based on CL-2 that is the most commonly found CL in the sera of humans. It was cloned by standard PCR amplification of human splenic cDNA with the primers pCL1 and pCL2 (Table 2). The 5' primer pCL1 contains the sequence for the HpaI cloning site and the 3' primer pCL2 contains the XbaI cloning site flanking the stop codon. Resulting sequences are shown in SEQ ID NOS: 13 and 14.

Figure 5:
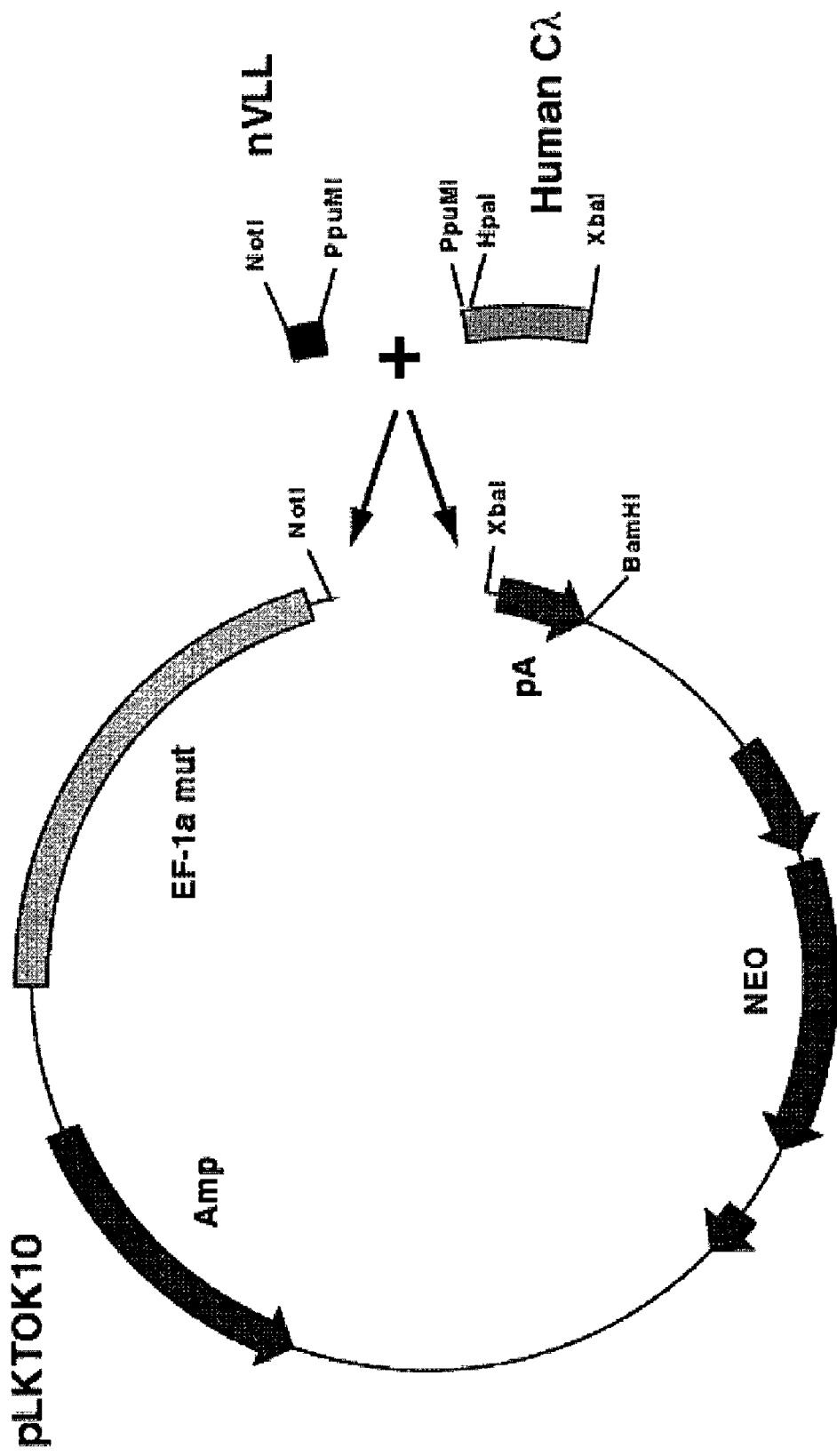
FIG. 5 depicts construction of an antibody lambda chain cassette vector and the cloning process used to combine the nVLL sequence with a CLambda light chain constant region in a single chain expression vector.

Cloning the nVLL fragment together with the CLambda fragment into the expression vector pLKTOK10 then created the human C Lambda cassette, named pLKTOK72 (FIG. 5).

TABLE 2

Primers used to create constant regions.

| PRIMER | DESCRIPTION | SEQUENCE | |
|---|---|---|---|
| pCHhum1 | 5' human IgG1 | 5'AGTCAGCTCAGCCTCCACCAAGGGCCCATC 3' | SEQ ID NO: 33 |
| pCHhum2 | 3' human IgG1 | 5'TGCTCTAGATTATTTACCCGGAGACAGGGAGA GGCTC 3' | SEQ ID NO: 34 |
| pCHhum3 | 1st mutation of FcR region | 5'GGAAGACTGACGGTGCCCCCGCGAGTTCAGG TGCTGGGCA 3' | SEQ ID NO: 35 |
| pCHhum4 | 2nd mutation of FcR region | 5'CCTGAACTCGCGGGGGCACCGTCAGTCTTCCT CTTCC 3' | SEQ ID NO: 36 |
| pIgGrh1 | 5' macaque IgG1 | 5'ACTAGTCACAGTCAGCTCAGCCTCCACCAAGG GCCCATCGGTCTTCCCCCTG 3' | SEQ ID NO: 37 |
| pIgGrh4 | 3' macaque IgG1 | 5'GCTCTAGATTATTTACCCGGAGACAGGGAGA GGC 3' | SEQ ID NO: 38 |
| pIgGcy2 | 1st mutation of FcR region | 5'CTGACGGTGCCCCCGCGAGTTCAGGTGCTGGG CACGGTGGGCACGTG 3' | SEQ ID NO: 39 |
| pIgGcy3 | 2nd mutation of FcR region | 5'CCGTGCCCAGCACCTGAACTCGCGGGGGCAC CGTCAGTCTTCCTCTTC 3' | SEQ ID NO: 40 |
| pCHmur1 | 5' mouse IgG2a | 5'AGTCAGCTCAGCCAAAACAACAGCCCCATCG GTCTATC 3' | SEQ ID NO: 41 |
| pCHmur4 | 3' mouse IgG2a | 5'TGCTCTAGATTATTTACCCAGAGACCGGGAGA TGGTC 3' | SEQ ID NO: 42 |
| pCHmur2 | 1st silent removal of BamHI site | 5'GGTGTGCACACCACTGGACAGGGAGCCAGAG TTCCAGGTC 3' | SEQ ID NO: 43 |
| pCHmur3 | 2nd silent removal of BamHI site | 5'CTCTGGCTCCCTGTCCAGTGGTGTGCACACCT TCCCAGCTCTCCTG 3' | SEQ ID NO: 44 |
| pCHmur5 | 1st mutation first FcR region | 5'TGAAGACGGATGGTGCACCTGCGAGGTCTGG AGCTGCGCA 3' | SEQ ID NO: 45 |
| pCHmur6 | 2nd mutation first FcR region | 5'GACCTCGCAGGTGCACCATCCGTCTTCATCTT CCCTCCA 3' | SEQ ID NO: 46 |
| pCHmur7 | 1st mutation second FcR region | 5'CCTTGCATTTGAATGCCTTGCCACTCATCCAG TCCTGGTGCTG 3' | SEQ ID NO: 47 |
| pCHmur8 | 2nd mutation second FcR region | 5'GTGGCAAGGCATTCAAATGCAAGGTCAACAA CAG 3' | SEQ ID NO: 48 |
| pCK1 | 5' human C Kappa | 5'TCAAAGCGTACGGTGGCTGCACCATCTGTC 3' | SEQ ID NO: 49 |
| pCK2 | 3' human C Kappa | 5'GCTGCTCTAGACTAACACTCTCCCCTGTTGAA 3' | SEQ ID NO: 50 |
| pCK4 | silent removal of Blp1 site | 5'GCACCCTGACCCTGAGCAAAG 3' | SEQ ID NO: 51 |
| pCL1 | 5' human C Lambda | 5'ATAAGAATGCGGCCGCAAGTTAACCGTCCTA GGTCAGCCCAAGGCTG 3' | SEQ ID NO: 52 |
| pCL2 | 3' human C Lambda | 5'GCTCTAGACTATGAACATTCTGTAGGGGC 3' | SEQ ID NO: 53 |
| pIgKcy1 | 5' macaque C Kappa | 5'GCGGCCGCCGTACGGTGGCTGCACCATCTGTC 3' | SEQ ID NO: 54 |

TABLE 2-continued

Primers used to create constant regions.

| PRIMER | DESCRIPTION | SEQUENCE | |
|---|---|---|---|
| pIgKcy4 | 3'macaque C Kappa | 5'TGCTCTAGACTAACACTCTCCCCTGTTGAAGC TC 3' | SEQ ID NO: 55 |
| pIgKcy2 | 1st silent removal of BlpI site | 5'GTCTGTGCTGCTCAACGTCAGGGTGCTGCTCA GGCTG 3' | SEQ ID NO: 56 |
| pIgKcy3 | 2nd silent removal of BlpI site | 5'GCACCCTGACGTTGAGCAGCACAGACTACCA GAG 3' | SEQ ID NO: 57 |
| pCKmur1 | 5'mouse C Kappa | 5'TCCCAGGGTCCCGTTCCGCTGATGCTGCACCA ACTGTATCGATATTCCCACCATCCAGTGAGCAG 3' | SEQ ID NO: 58 |
| pCKmur2 | 3'mouse C Kappa | 5'TGCTCTAGATTAACACTCATTCCTGTTGAAGC TCTTG 3' | SEQ ID NO: 59 |

EXAMPLE 3

Creation of Macaque Cassettes

Published sequences for the cynomologous and rhesus macaques IgG1 cDNA's were different at 3 amino acids so cDNA for IgG1 isolated from PBLs from both monkey species (See, e.g., Calvas P, et al. Characterization of the three immunoglobulin G subclasses of macaques. 1999 Scand J Immunol 49(6):595–610; and Lewis AP, et al. Cloning and sequence analysis of kappa and gamma cynomolgus monkey immunoglobulin cDNAs. 1993. Dev Comp Immunol 17(6):549–60). Sequencing analysis determined that the reported differences did not truly exist so a single macaque IgG1 cassette could be created for use in both monkey species.

The macaque heavy chain constant region, macaque IgG1-WT, was constructed by a standard PCR reaction of rhesus PBL cDNA with the primers pIgGrh1 and pIgGrh4 (Table 2). The primer pIgGrh1 contains the cloning site BlpI within its 5' equence and the primer pIgGrh4 contains a stop codon followed by the cloning site XbaI. Resultant sequences are depicted in SEQ ID NOS: 15 and 16.

Cloning the nVHL fragment together with the macaque IgG1-WT fragment into the expression vector pLKTOK10 then created the macaque IgG1-WT cassette, named pLK-TOK65 (FIG. 3).

The FcR mutated version of the macaque IgG1 was created by a protocol similar to that described for the human IgG1-FcRmut (pLKTOK56). In addition to the primers pIgGrh1 and pIgGrh4, the mutations L235A and G237A were added by PCR assembly using the primers pIgGcy2 and pIgGcy3 (Table 2). Resultant sequences are depicted in SEQ ID NOS: 17 & 18.

Cloning the nVHL fragment together with the macaque IgG1-FcRmut fragment into the expression vector pLK-TOK10 (FIG. 3), then created the macaque IgG1-FcRmut cassette named pLKTOK66.

Although different C Kappa genes were published for the rhesus and cynomologous macaques, both cDNAs were isolated from PBL cDNA of both monkeys, suggesting that either C Kappa would be non-immunogenic in both monkeys. For that reason, a single macaque C Kappa cassette was created.

The macaque C Kappa region, macaque CK, was constructed by a standard PCR reaction of cynomologous PBL cDNA with the primers pIgKcy1 and pIgKcy4 (Table 2). The primer pIgGrh1 contains the cloning site BlpI within its 5' sequence and the primer pIgGrh4 contains a stop codon followed by the cloning site XbaI. A BlpI restriction enzyme site at position 180 was silently mutated by a protocol similar to that described for the human IgG1-FcRmut (pLK-TOK56). In addition to the primers pIgKcy1 and pIgKcy4, a silent mutation was added by PCR assembly using the primers pIgKcy2 and pIgKcy3 (Table 2). Resultant sequences are shown in SEQ ID NOS: 19 and 20.

Cloning the nVKL fragment together with the macaque CKappa fragment into the expression vector pLKTOK10 (FIG. 4), then created the macaque CKappa cassette named pLKTOK67.

EXAMPLE 4

Creation of Mouse Cassettes

The murine heavy chain constant region, mouse IgG2a-WT, was constructed from the C57BL/6 splenic cDNA. Mouse IgG2a was selected because it is similar in sequence structure and function to human IgG1. As C57BL/6 IgG2a cDNA contains a BamHI restriction site at position 156, the construct with the silent mutation was created by PCR assembly as described for human IgG1-FcRmut. The primer pCHmur1 contains the cloning site BlpI within its 5' sequence and the primer pCHmur4 contains a stop codon followed by the cloning site XbaI. The silent mutation was encoded in the primers pCHmur2 and pCHmur3 (Table 2) (SEQ ID NO: 21 & 22).

Cloning the nVHL fragment together with the murine IgG2a fragment into the expression vector pLKTOK10 (FIG. 3) then created the murine IgG2a-WT cassette, named pLKTOK60.

The mouse IgG2a is believed to have two regions that can interact with Fc receptors (Issac) and both were removed by PCR assembly. The primers pCHmur5 and pCHmur6 created the mutations L235A and G237A. The primers pCHmur7 and pCHmur8 created the mutation E318A. These primers, along with the primers pCHmur1 and pCHmur4, allowed the creation of murine IgG2a-FcRmut (Table 2) (SEQ ID NO: 23 & 24).

Cloning the nVHL fragment together with the murine IgG2a-FcRmut fragment into the expression vector pLK-TOK10 (FIG. 3) then created the murine IgG2a-FcRmut cassette, named pLKTOK61.

The murine kappa constant region was created by standard PCR amplification of murine C57BL/6 splenic cDNA with the primers pCKmur1 and pCKmur2 (Table 2) (SEQ ID NO: 25 & 26). Instead of the cloning site BsiWI, the 5' primer pCKmur1 contains the sequence for the ClaI cloning site and the 3' primer pCKmur2 contains the XbaI cloning site flanking the stop codon.

Cloning the nVKL fragment together with the murine CKappa fragment into the expression vector pLKTOK10 (FIG. 4), then created the murine C Kappa cassette, named pLKTOK62.

EXAMPLE 5

Creation of Combined Immunoglobulin DNA Cassette Vectors

A pcDNA3 was used as a backbone vector which contains the gene for resistance to G418 (NEO) to allow for easy selection in research conditions. The SpeI restriction site was eliminated from pcDNA3 by site directed mutagenesis. The EF-1a promoter from the plasmid pcDEF3 (originally pBOS) was inserted into pcDNA3, thus eliminating the CMV promoter.

A BamHI site in the pcDNA3 cloning linker and an Mfe I cloning site within the EF-1a promoter were removed using site directed mutagenesis, and a BamHI site was added 3' in the polyA region. This allowed the combination of the heavy and light chain active regions in a single vector and would allow for the addition of any other selectable marker including the gene cassette DHFR that confers resistance to methyltrexate.

Figure 6:
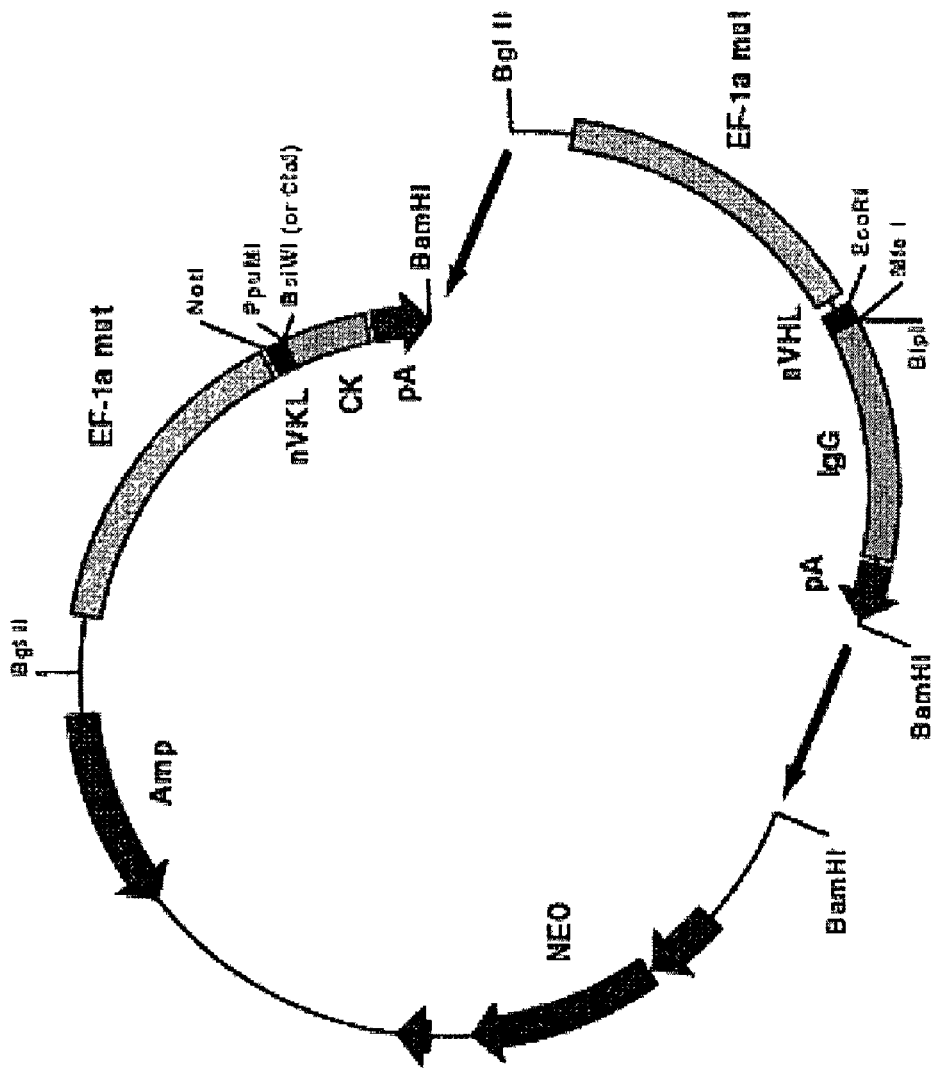
FIG. 6 depicts construction process for transfer of heavy chain cassettes and light chain cassettes into a single combination immunoglobulin DNA cassette vector. For creation of combined vectors, the heavy chain cassette, including promoter, nVHL, IgG constant region and polyadenylation region, can be cloned as a Bgl II/Bam HI fragment into the Bam HI site of the vector with the light chain cassette. Bgl II and Bam HI have cohesive ends and both sites are lost upon ligation.
Figure 7:
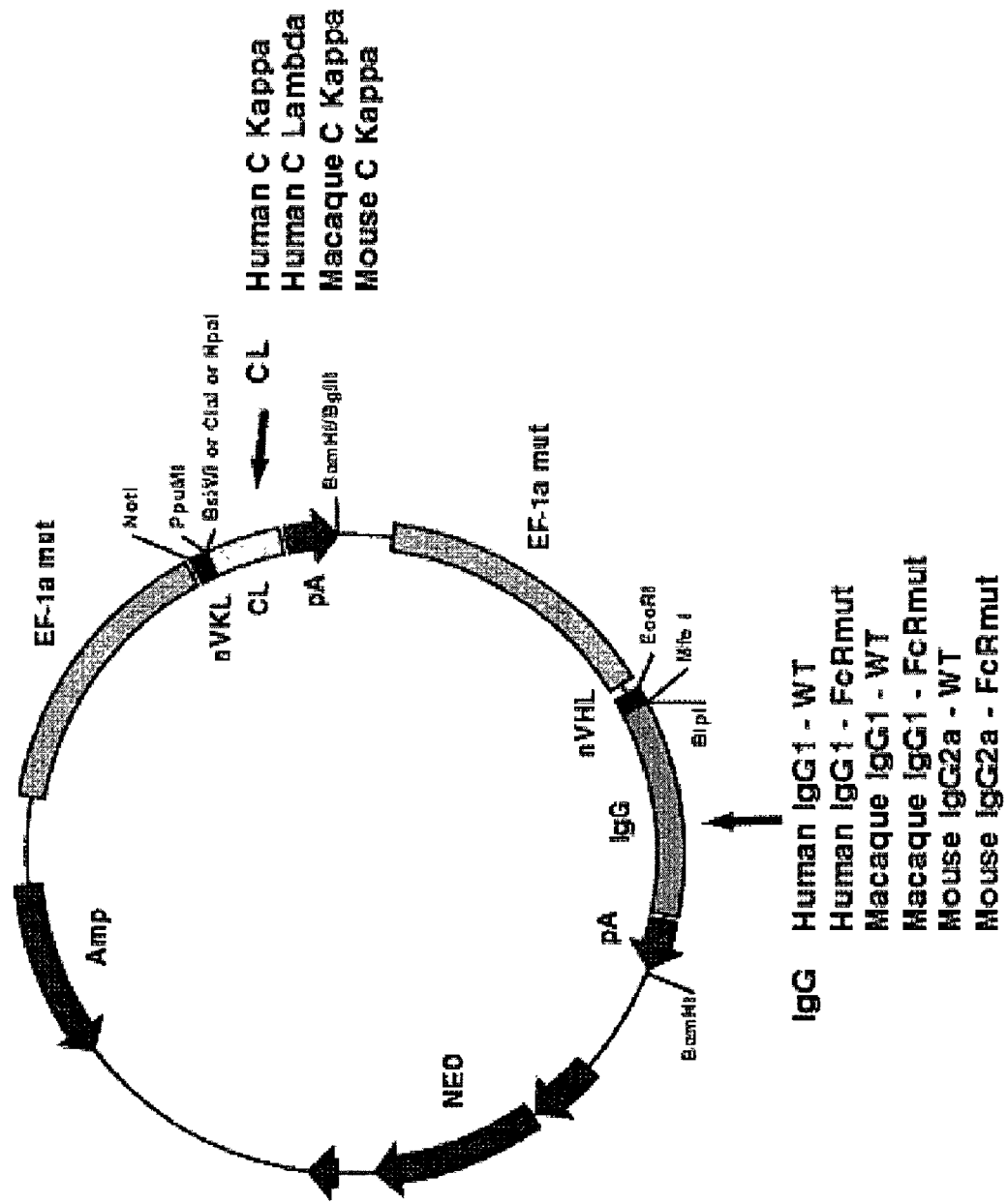
FIG. 7 depicts the structure of the complete combination heavy and light chain immunoglobulin DNA cassette antibody expression vector.

The heavy chain cassettes (including its promoter and polyadenylation region) were subcloned from the various single cassette vectors into their corresponding light chain cassette vectors to create the combined two cassette vectors (FIG. 6). The combinations are summarized in Table 3. All the combination vectors had a similar overall structure that is shown in FIG. 7.

The pLKTOK58 vector, created by combining pLKTOK55 and pLKTOK57, can be used to produce an antibody that contains a human kappa constant region and human IgG1 constant region in its native form. The pLKTOK59 vector, created by combining pLKTOK56 and pLKTOK57, can be used to produce an antibody that contains a human kappa constant region and a human IgG1-FcRmut constant region contains the mutations at positions L235A and G237A. These mutations inhibit the binding of the constant region to human Fc receptors and inhibit the initiation of ADCC reactions. Such mutation have been described previously in U.S. Pat. No.: 5,985,279 and International Publication No.: WO98/06248, which are incorporated herein by reference. The pLKTOK92 and pLKTOK73 vectors, created by combining pLKTOK55 or pLKTOK56 and pLKTOK72, can be used to produce antibodies that contain human lambda constant regions and either human IgG1-WT (pLKTOK92) or human IgG1-FcRmut (pLKTOK73).

The vectors pLKTOK68 and pLKTOK69, created by combining pLKTOK65 or pLKTOK66 and pLKTOK67, can be used to produce antibodies that contain a macaque kappa constant region and macaque IgG1 constant region. The constant region of pLKTOK68 is IgG1-WT for both cynomologous and rhesus macaques. The constant region of pLKTOK69 is IgG1-FcRmut that contains the L235A and G237A mutations and theoretically should inhibit the binding of the constant region to macaque FC receptors. The kappa constant region is one of the two kappa constant regions expressed by both the cynomologous and rhesus macaques thus should be recognized as native by both monkey species.

The vectors pLKTOK63 and pLKTOK64, created by combining pLKTOK60 or pLKTOK61 and pLKTOK62, can be used to produce antibodies that contain a mouse kappa constant region and mouse C57BL/6 IgG2a constant region. The constant region of pLKTOK63 is the native conformation of IgG2a in mouse and is the allotype most closely matched in structure and function to human IgG1. The constant region of pLKTOK64 contains the murine IgG1 with the mutations at positions L235A and G237A (for Fc region I) and E318A (for Fc region II) to inhibit the binding of the constant region to mouse FC receptors and inhibit the initiation of ADCC reactions (See, Isaacs J D, et al. Therapy with monoclonal antibodies. II. The contribution of Fc gamma receptor binding and the influence of C(H)1 and C(H)3 domains on in vivo effector function. 1998. J Immunol. 161(8):3862–9.)

TABLE 3

Composition of combined expression vectors.

| COMBINED VECTOR | HEAVY CHAIN VECTOR | HEAVY CHAIN COMPOSITION | LIGHT CHAIN VECTOR | LIGHT CHAIN COMPOSITION |
| --- | --- | --- | --- | --- |
| pLKTOK58 | pLKTOK55 | nVHL-Human IgG1-WT | pLKTOK57 | nVKL-Human C Kappa |
| pLKTOK59 | pLKTOK56 | nVHL-Human IgG1-FcRmut | pLKTOK57 | nVKL-Human C Kappa |
| pLKTOK92 | pLKTOK55 | nVHL-Human IgG1-WT | pLKTOK72 | nVLL-Human C Lambda |
| pLKTOK73 | pLKTOK56 | nVHL-Human IgG1-FcRmut | pLKTOK72 | nVLL-Human C Lambda |
| pLKTOK68 | pLKTOK65 | nVHL-Macaque IgG1-WT | pLKTOK67 | nVKL-Macaque C Kappa |
| pLKTOK69 | pLKTOK66 | nVHL-Macaque IgG1-FcRmut | pLKTOK67 | nVKL-Macaque C Kappa |
| pLKTOK63 | pLKTOK60 | nVHL-Mouse IgG2a-WT | pLKTOK62 | nVKL-Mouse C Kappa |
| pLKTOK64 | pLKTOK61 | nVHL-Mouse IgG2a-FcRmut | pLKTOK62 | nVKL-Mouse C Kappa |

EXAMPLE 6

Creation of DNA Cassette Insert Sequences: Adapting Antibody Variable Regions To test these vectors by creating intact antibodies, the variable regions from the 10 monoclonal antibody 1D9 were PCR adapted to add the desired restriction enzyme sites (MfeI and BlpI for the VH, PpuMI and BsiWI for the human and macaque VK and PpuMI and ClaI for the mouse VK. The 1D9 antibodies have been described previously in International Publication Nos: WO 00/05265 and WO 01/57226, which are incorporated herein by reference. Once adapted, these and any other set of variable regions could be cloned into the various expression vectors.

The primers for the VH region are designed such that the 5' primer includes the 7 codons at the end of the VH leader (including the Mfe I restriction enzyme) and the first 7–9 codons of the hybridoma VH. The 3' primer included 7–9 codons of the hybridoma VH followed by 3 codons of the IgG1 constant region (including the BlpI restriction enzyme). 20 Primers used for adapting variable regions are demonstrated in Table 4, (upper case letters depict identical sequences for all antibodies encoded in vectors; lower case letters are determined by the sequence of the individual antibody).

Figure 8:
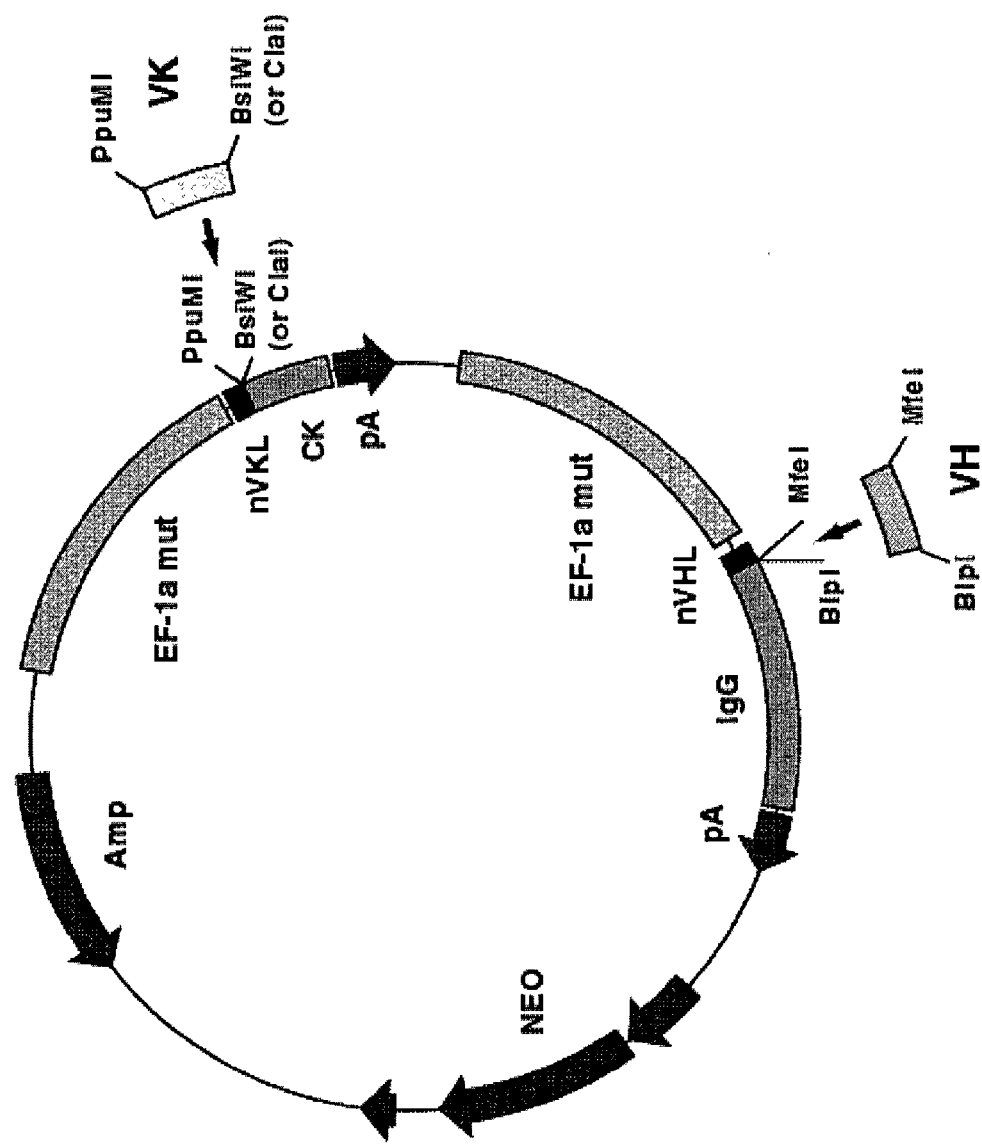
FIG. 8 depicts the cloning process for incorporation of desired variable sequences (VH and VK) into the combination heavy and light chain immunoglobulin DNA cassette antibody expression vector.
Figure 9:
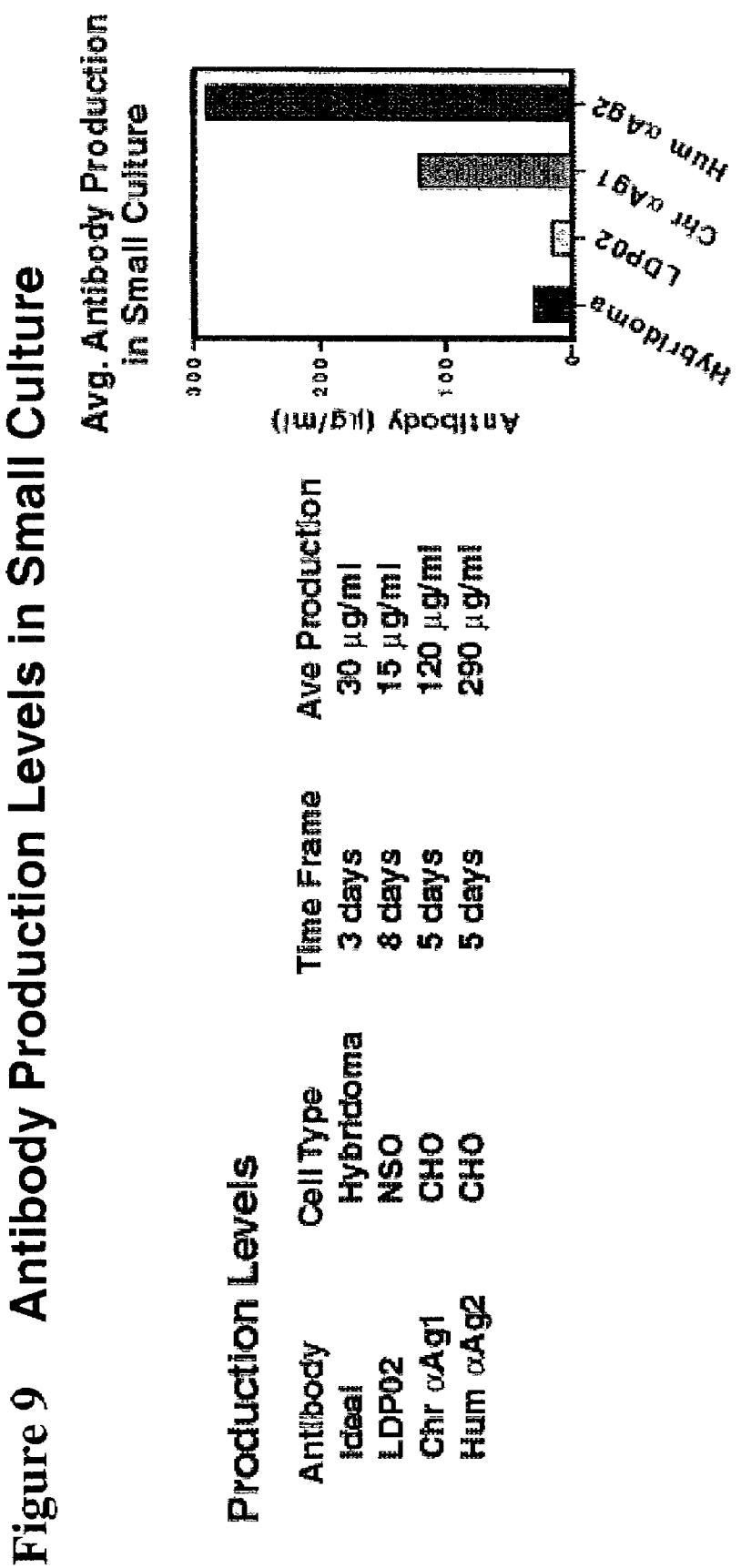
FIG. 9 depicts demonstrative results of antibody production levels of recombinant cells generated using the antibody production and conversion system of the present invention.
Figure 10:
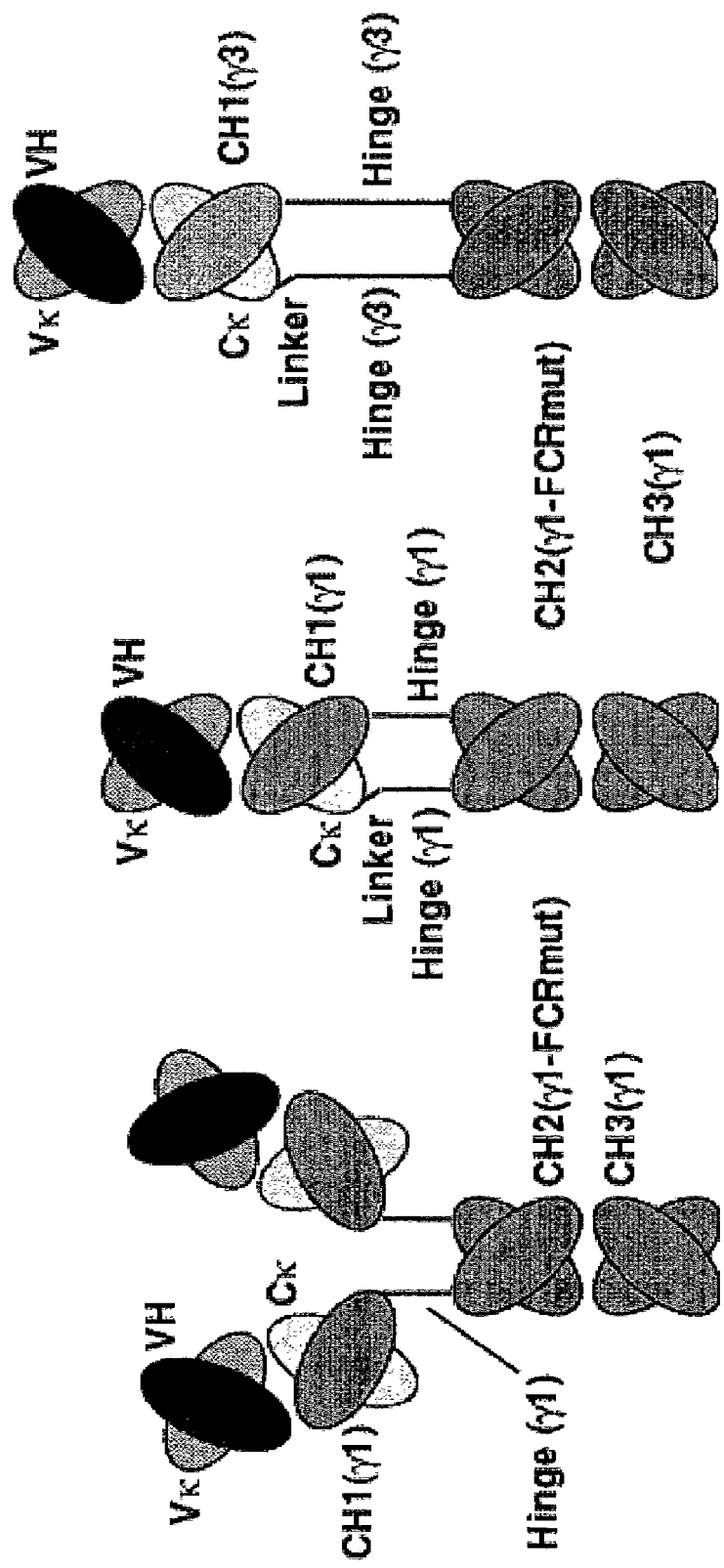
FIG. 10 depicts proposed structure of monobody constructs in comparison with traditional antibody structure.

The primers for the VK region are designed such that the 5' primer includes the 6 codons at the end of the VK leader (including the PpuM I restriction enzyme) and the first 7–9 codons of the hybridoma VK (Table 4). The human 3' primer included 7–9 codons of the hybridoma VH followed by 4 codons of the human kappa constant region (including the BsiWI restriction enzyme). The mouse 3' primer included 7–9 codons of the hybridoma VH followed by 12 codons of the mouse kappa constant region (including the ClaI restriction enzyme) (Table 4). The primers used to adapt the hybridoma 1D9 VH gene were n1D9VH5 and n1D9VH3. The primers used to adapt the hybridoma 1D9 VK gene were n1D9VK5 and n1D9VK3. The adapted 1D9 VH and VK genes were cloned into the vectors in standard two step cloning to create the complete plasmids (FIG. 8).

production of secreted proteins. A major component of protein production is the function of its promoter.

For the successful folding and transport of antibodies out of cell, two proteins must be produced and properly associate. It is believed that having similar concentrations of the heavy and light chains may assist in the association, folding and transportation of the antibodies. An excess of one antibody chain within a cell can lead to cell death. We believed that creating cassettes in which each antibody chain had its own promoter through polyadenylation site would increase the likely-hood of equivalent protein production of the two chains. This system also uses cDNA inserts that eliminate the need for post-translational modification. The decreased variability may reduce the levels of other RNA species and increase the levels of the desired RNA species.

To test this system and determine optimal promoter combinations, vectors were created with either the CMV or the EF-1a promoters. (See U.S. Pat. Nos.: 5,225,348 and 5,266,491; Mizushima S, Nagata S. pEF-BOS, a powerful mammalian expression vector. 1990 Nucleic Acids Res 18(17):5322.) In both cases, restriction sites that would interfere with cloning within these cassettes were removed by site directed mutagenesis. The SpeI cloning site was removed from CMV and the MfeI cloning site was removed from EF-1a. Testing with an EGFP cassette demonstrated these changes did not make any noticeable changes in the general function of the promoters. A vector was also created with a combination of the mutated CMV promoter with the beta-kinesin IRES to see if that increased antibody production.

The vector pcDNA3 was used as a backbone vector because it contains the gene for resistance to G418 (NEO) to allow for easy selection in research conditions. Into this vector was cloned the mutated CMV promoter, the mutated CMV promoter with the beta-kinesin IRES or the mutated EF-1a promoter.

Changes to aid in cloning were made to the vector backbone including the removal of a MfeI cloning site 5' of the promoter. A BamHI site in the pcDNA3 cloning linker was removed and a BamHI site was added 3' of the polyadenylation region. This flanking BamHI site allows the

TABLE 4

Primers to adapt 1D9 VH and VK for cloning into all expression vectors.
(Upper case letters are identical for all antibodies. Lower case letters are determined by the sequence of the individual antibody.)

| PRIMER | SEQUENCE | | |
|---|---|---|---|
| n1D9VH5 | 5' TTACCCAATTGTGTCCTGTCCgaggtgcagcttgttgagtctg 3' | SEQ ID NO: | 60 |
| n1D9VH3 | 5' GTTTTAGGCTGAGCTgacggtgaccgtggtccctgtg 3' | SEQ ID NO: | 61 |
| n1D9VK5 | 5' TTCCCAGGGTCCCGTTCCgatgttgtgatgacccagact 3' | SEQ ID NO: | 62 |
| n1D9VKhum3 | 5' AGCCACCGTACGCtttatttccagcttggtcc 3' | SEQ ID NO: | 63 |
| n1D9VKmur3 | 5' TGGGAATATCGATACAGTTGGTGCAGCATCAGCACGCtttatttccagcttg gtcc 3' | SEQ ID NO: | 64 |

EXAMPLE 7

Testing the System: Determining Relative Rates of Antibody Production

The protein production level, the rate of correct folding and the rate of transportation out of cells determine high transfer of the heavy chain cassettes (as a BglII/BamHI fragment) including their promoters and polyadenylation regions into vectors containing the light chain cassettes. As a single BamHI site remains after the cloning, it allows for the later addition of any other selectable marker including the gene cassette for DHFR, which confers resistance to methotrexate.

Three matched vectors were constructed to test the system. Each was a single vector with a light chain cassette (with its promoter and polyadenylation region) followed by a heavy chain cassette (with its promoter and polyadenylation region). All three vectors contain the 1D9 VK functionally attached to the human C Kappa gene and the 1D9 VH functionally attached to the human IgG1-FcRmut gene by the method described in the construction of the inserts. The vectors differed only in their promoter combination. The vector pLKTOK34 had both the light and heavy chain cassettes driven by the mutated CMV promoter. The vector pLKTOK36 had both the light and heavy chain cassettes driven by the mutated CMV promoter combined with the beta-kinesin IRES. The vector pLKTOK38 had both the light and heavy chain cassettes driven by the mutated EF-1a promoter.

Completed vectors were transfected into CHO cells and selected in G418 media. This media results in the death of all cells that do not contain the gene for Neomycin resistance. After 5 days of selection in G418, cells were trypsinized to make a single cell suspension and plated in 96 well plates at the rate of 1, 5 or 10 cells/well. At 5 days of selection, most of the G418 non-resistant cells will be programmed to die. These clones were expanded and tested repeatedly to determine their ability to retain high production levels.

After 10 days in the 96 well plates, the plates are scored visually to select the wells that contain a single CHO clone. At two weeks, these are tested for their ability to produce and secrete intact antibody as measured by an ELISA that coats the wells with a Fab' against human heavy and light and develops with Protein A attached to the enzyme HRP.

In various transfections, 50–70% of the tested single clone wells were producing antibody in significant amounts and usually 70% + would retain production after transfer.

The best clones were tested on their ability to produce antibody over a 5-day period both with and without butyric acid (necessary to amplify CMV production). It was determined that the CMVmut cells produced an average of 0.5 ug/ml without butyric acid treatment and 1.8 ug/ml with butyric acid treatment. The CMVmut/IRES cells produced an average of 0.7 ug/ml without butyric acid treatment and 0.2 ug/ml with butyric acid treatment. The EF-1a cells produced an average of 122.6 ug/ml without butyric acid treatment and 50.2 ug/ml with butyric acid treatment. The results demonstrated that the EF-1a promoter produced 100× the amount of antibody.

It is quite possible that the two chains of the antibody driven by their own promoters and having their own polyadenylation regions allows for the two proteins to be produced at similar rates. Having similar amounts of the two chains probably assists in the correct and rapid association, folding and transportation out of the CHO cells. Functional testing of the antibodies generated demonstrated that the antibodies produced using the present system function in similar fashion to those produced by the original 1D9 hybridoma.

Development of Monobody Constructs.

Two versions of a monobody construct have been developed, using either an IgG1 hinge or IgG3 hinge region. The first, exemplified herein as part of the pLKTOK77 vector is a monobody comprising an intact heavy chain IgG1 and an extended light chain C kappa attached to an IgG1 hinge as well as IgG1 CH2 and CH3 constant regions (FIGS. 11 & 12). The second, exemplified herein as part of the pLKTOK78 vector is a monobody A combining a heavy chain comprising a combination IgG3 hinge and CH1 as well as an IgG1 CH2 and CH3 regions and a light chain C kappa attached to an IgG3 hinge and IgG1 CH2 and CH3 constant regions (FIGS. 11 & 13).

EXAMPLE 8

Construction of pLKTOK77

Monobody DNA cassette constructs were generated, and a heavy chain and extended light chain cassette incorporated into a single vector which is capable of accepting variable sequences of interest to generate a monobody capable of detecting the desired antigen. For creation of the first construct comprising an extended light chain with an IgG1 hinge and constant region, first a heavy chain cassette was created by combining a VH leader or signal sequence with a human IgG1 sequence. Heavy chain sequences were prepared as described for DNA cassettes Examples 1 and 2 supra, to create IgG1FcRmut cassette pLKTOK56. The entire region of promoter through polyadenylation region is flanked with Bgl II and BamHI restriction enzyme sites so the entire cassette can be transferred to a second expression vector that contains the extended light chain cassette to create the complete monobody expression vector to which variable regions can be added.

The extended light chain of pLKTOK77 was created by attaching a light chain leader sequence to a human kappa constant region, and further attaching the light chain constant region to a hinge and the CH2 and CH3 regions of the human IgG1 constant region. The light chain signal sequence was created as in the description of creation of light chain leaders in immunoglobulin DNA cassettes, and modified for incorporation into cassettes (as described in Example 1 & 2). Between light chain constant region and the IgG constant region, a DNA sequence encoding the linker SGGGGSGGGGSGGGGS (SEQ ID NO:111) was included to allow flexibility between the protein domains and increase the likelihood of stable association and folding (FIG. 1).

TABLE 5

Primers used to create monobody constant regions.

| PRIMER | DESCRIPTION | SEQUENCE | |
|---|---|---|---|
| pCHhum1 | 5' human IgG1 | 5'AGTCAGCTCAGCCTCCACCAAGGGCCCATC 3' | SEQ ID NO: 33 |
| pCHhum2 | 3' human IgG1 | 5'TGCTCTAGATTATTTACCCGGAGACAGGGA GAGGCTC 3' | SEQ ID NO: 34 |

TABLE 5-continued

Primers used to create monobody constant regions.

| PRIMER | DESCRIPTION | SEQUENCE | |
|---|---|---|---|
| pCHhum3 | 1st mutation of FcR region | 5'GGAAGACTGACGGTGCCCCCGCGAGTTCA GGTGCTGGGCA 3' | SEQ ID NO: 35 |
| pCHhum4 | 2nd mutation of FcR region | 5'CCTGAACTCGCGGGGGCACCGTCAGTCTTC CTCTTCC 3' | SEQ ID NO: 36 |
| pCK1 | 5' human C Kappa | 5'TCAAAGCGTACGGTGGCTGCACCATCTGTC 3' | SEQ ID NO: 49 |
| pCK2 | 3' human C Kappa | 5'GCTGCTCTAGACTAACACTCTCCCCTGTTG AA 3' | SEQ ID NO: 50 |
| pCK4 | silent removal of BlpI site | 5'GCACCCTGACCCTGAGCAAAG 3' | SEQ ID NO: 51 |
| pMVa | 5' human IgG3-CH1 | 5'GTCAGCTCAGCTTCCACCAAGGGCCCATCG GTCTTCCCCCTGGCGCCCTG 3' | SEQ ID NO: 89 |
| pMVe | 3' linker to human C Kappa | 5'CGATCCACCGCCCCCGCTGCCACCTCCCCC TGAACCCCGCCTCCACTACACTCTCCCCTGT TGAAGCT 3' | SEQ ID NO: 90 |
| pMVf | 5' linker to human IgG1 Hinge-CH2-CH3 | 5'GGTGGCAGCGGGGGCGGTGGATCGTGCCC ACCGTGCCCAGCACC 3' | SEQ ID NO: 91 |
| pMVh | 3' adapt human C kappa. | 5'TTTGGGCTCCGGACACCGCGGGCACGATCC ACCG 3' | SEQ ID NO: 92 |
| pMVm | 3' adapt human IgG3 hinge | 5'CGGTGCCCCGGCCAGTTCAGGAGCGGGGC ACCTTG 3' | SEQ ID NO: 93 |
| pMVp | 5' adapt human IgG1 CH2-CH3 (FcRmut) | 5'GGTGCCCCGCTCCTGAACTGGCCGGGGCAC CGTCAGTCT 3' | SEQ ID NO: 94 |

The 5' half of the DNA was constructed by PCR to create the human kappa constant 5 region with an added serine followed by a standard 15 mer (GGGGS) 3 linker and the first 20–30 bases of the human IgG1 hinge. The PCR template was the human kappa constant region in which the sequence encoding the BlpI restriction enzyme at position 180 was removed by site directed mutagenesis using the primer pCK4 and the Transformer Site-Directed Mutagenesis Kit produced by CloneTech (Palo Alto, Calif.). This BlpI site would 10 interfere with the cloning of the VH gene into the heavy chain cassette (see Examples above). The 5' primer (pCK1) used to amplify the kappa constant contains the DNA sequence for the BsiWI restriction enzyme and the 3' primer (pMVe) contains the sequence for an added serine followed by a sequence for (GGGGS) 3 and the first 20–30 bases of the human IgG1 hinge. The second half of the DNA was amplified using the template of human IgG1-FCRmut and the primers pMVf and pCHhum2. The primers anneal to the human IgG1 hinge and start with 20–30 bases that complement the linker. The 3' primer contains the XbaI cloning site flanking the stop codon. The PCR assembly used to create the extended light chain was similar to that described in the construction of the heavy chain. The first two fragments were created by a standard PCR reaction and gel purified. They were then combined in equal molar quantities and assembled and material from this reaction was used as a template to amplify the combined protein using the primers pCK1 and pCHhum2. The resulting produce (1056 bp) was TA cloned and sequenced to determine the correct sequence was produced.

The extended light chain constant region was subcloned with the VKL gene into the pLKTOK10 vector (see above) and the resulting vector called pLKTOK75. The heavy chain cassette with its promoter through poly-adeneylation region was isolated from pLKTOK56 and cloning it into the BamHI region of pLKTOK75 to create pLKTOK77, the final vector (FIG. 12). This created a single plasmid which has both the heavy chain and extended light chain monobody cassettes.

EXAMPLE 9

Construction of pLKTOK78

Another version of a monobody construct, pLKTOK78, has a similar structure to the first version (pLKTOK77) but has additional flexibility in it folding and stability due to the fact that it contains the CH1 and hinge of human IgG3 (versus human IgG1) in it heavy chain protein and the hinge of the human IgG3 between the kappa constant with the linker and the CH2-CH3 domains of IgG1 (FIGS. 11 & 13). The first section of the heavy chain was created by PCR adaptation of the human IgG3 CH1 and hinge from human splenic cDNA (Invitrogen) to include restriction cloning sites. The 5' primer (pMVa) contains the BlpI restriction site for cloning of the VH genes and the 3' primer (pMVm) contains the start of the IgG1 CH2 with the sequence for the restriction enzyme EaeI. The second section of the heavy chain was created by PCR adaptation of the IgG1 CH2-CH3-FCRmut to include restriction cloning sites. Its 5' primer (pMVp) contains the sequence for the restriction enzyme EaeI within the start of the IgG1 CH2 and its 3' primer was pCHhum2 that contains the XbaI cloning site. The two resulting PCR products were TA cloned and individual clones sequenced to select for the clones with the desired sequences. These fragments were subcloned with the VHL gene into the expression vector pLKTOK10 to create pLKTOK74.

The extended light chain of pLKTOK78 was created by PCR adaptation of three fragments with added restriction enzyme sites that allowed the three fragments to be cloned together. The kappa constant region with the attached serine and 15-mer linker were amplified with the primers pCK1 (contains restriction enzyme BsiWI) and pMVh (contains the restriction enzyme SacII) using as template the CK without the BlpI restriction site.

The entire extended light chain was created by cloning the three fragments—kappa constant/linker (BsiWi/SacII), IgG3 hinge (SacII/EaeI) and the IgG1 CH2-CH3-FCRm (EaeI/XbaI) along with the VKL (EcoRI/BsiWI) into the pLKTOK10 expression vector to create the vector named pLKTOK76 (FIG. 13; SEQ ID NO: 109). The heavy chain cassette with its promoter through poly-adeneylation region was isolated from pLKTOK74 and cloned into the BamHI site of pLKTOK76 to create pLKTOK78, the final vector (FIG. 13). This created a single plasmid that has both the heavy chain and extended light chain monobody cassettes.

TABLE 6

Primers to create new IgG3 Hinge for pLTOK76

| PRIMER | SEQUENCE | |
|---|---|---|
| pPr9a | 5'TCGTGCCCGCGGTGTCCGGAGCCCAAATCTTGTGACACACCTCCC CCGTGCCCTAGATGTCCAGAGCCGAAATCG 3' | SEQ ID NO: 95 |
| pPr9b | 5'CAGGGCGGTGGAGTGTCACACGATTTCGGCTCTGGACATCTA 3' | SEQ ID NO: 96 |
| pPr9c | 5'CACTCCACCGCCCTGTCCACGCTGCCCTGAACCAAAGAGCT 3' | SEQ ID NO: 97 |
| pPr9d | 5'CGGTGCCCCGGCCAGTTCAGGAGCGGGGCACCTTGGACATGGAG GCGGCGTATCGCAGCTCTTTGGTTCAGGGCAGCGT 3' | SEQ ID NO: 98 |
| pPr9e | 5'TCGTGCCCGCGGTGTCCGGAGCCCAAATCT 3' | SEQ ID NO: 99 |
| pPr9f | 5'CGGTGCCCCGGCCAGTTCAGGAGC 3' | SEQ ID NO: 100 |

To remove the three DNA repeats within the human IgG3 hinge that frequently self-splice during PCR, a new DNA sequence to encode the human IgG3 hinge was created which removes these DNA repeats. This DNA was created with 4 overlapping primers, Pr9a, Pr9b, Pr9c and Pr9d. Pr9a has 22 bases of complimentary DNA with Pr9b, which has 13 bases of complimentary DNA with Pr9C, which has 23 bases of complimentary DNA with Pr9d. These 4 primers were combined in equal molar ratios to anneal and amplifying with Taq polymerase in a reaction 94° C. for 2 minutes followed by of 20 cycles of 94° C. for 2 minutes and 72° C. for 2.5 minutes with 30 second ramping and finishing with 72° C. for 10 minutes. The result of this reaction was amplified with the primers Pr9e and Pr9f that produced a fragment that was TA cloned and sequenced. The primers Pr9e and Pr9f contains the cloning sites SacII and EaeI respectively to allow the new hinge to be cloned between the CK and the IgG1 CH2-CH3.

New_Pr9
SEQ ID NO: 103
TCGTGCCCGCGGTGTCCGGAGCCCAAATCTTGTGACACACCTCCCCCGTG

CCCTAGATGTCCAGAGCCGAAATCGTGTGACACTCCACCGCCCTGTCCAC

GCTGCCCTGAACCAAAGAGCTGCGATACGCCGCCTCCATGTCCAAGGTGC

CCCGCTCCTGAACTGGCCGGGGCACCG

New Pr9 protein sequence
SEQ ID NO: 104
SCPRCPEPKSCDTPPPCPRCPEPKSCDTPPPCPRCPEPKSCDTPPPCPRC

PAPELAGAP

The IgG1 CH2-CH3-FCRmut fragment was PCR adapted with the primers pMVp (contains an EaeI restriction site) and pCHhum2 (contains a XbaI restriction site) (FIG. 13). The resulting PCR fragment was TA cloned and sequenced.

EXAMPLE 10

Monobody Construction and Preparation

To create a monobody, variable regions from the antibody 1D9 were PCR adapted to add the desired restriction enzyme sites (MfeI and BlpI for VH and PpuMI and BsiWI for VK), as described in Example 6, supra. Prepared fragments cloned into the Monobody 10 DNA cassette plasmid pLKTOK77. The adapted 1D9 VH and VK genes were cloned into the vector pLKTOK77 in a standard two step cloning to create the pLKTOK77-1D9 plasmid. To create the second monobody, the adapted variable regions from the antibody 1D9 were cloned into the pLKTOK78 plasmid in the same manner as described for pLKTOK77 in a standard two step cloning to create the pLKTOK78-1D9 plasmid.

The pLKTOK77-1D9 or pLKTOK78-1D9 was transfected into CHO cells by standard Calcium phosphate precipitation, selected with G418 and single monobody producing clones isolated. The presence of intact monobody was determined by the presence of protein in the supernatant that was captured on an ELISA plate by anti-human Fc and visualized with enzyme linked protein A. Because of the nature of the protein, the monobody could be produced and purified by the standard methods of production and purification of intact antibodies.

EXAMPLE 11

Determination of Monobody Structure and Function

The structure and function of the monobodies were determined by standard techniques including non-reduced and reduced gradient acrylamide gels that were then Western probed for the presence of human IgG1 and human kappa constant region. Gels were run in non-reducing conditions on a 4–20% gradient Tris-Glycine gel with the heavy chain detected with anti-human IgG, and the light chain detected with anti-human CK. Four individual monobody preps were compared with a chimeric 1D9 antibody. The estimated Molecular Weight (MW) for an intact antibody is 150 KDa with the heavy chain 49 KDa and the light chain 25 KDa. Both the heavy chain and the extended light chain of the monobody would be about 49 KDa with a combined weight of about 100 KDa, as estimated molecular weights. Both the heavy and the extended light chains migrate at approximately 50 KDa and the monobody has a MW approximately ⅔ the weight of an antibody, as predicted.

Purified monobodies were run on isoelectric focusing gels to determine their pI. The estimated pI for the extended light chain is 7.42 and 8.8 for the heavy chain. The estimated combined pI for the monobody is 8.0. The IEF gel shows a pI of about 7.6–7.8 which suggests a product containing a single extended light chain with a single heavy chain. The difference (as compared to the estimate of 8.0) may be due to the gylcosylation of both the heavy and extended light chains of the monobody constructs.

The ability of monobody to bind the target protein of 1D9(CCR2) was determined by their ability to bind human monocytes (gated with anti-CD14-FITC) (FIG. 14). Their presence could be determined with anti-human IgG-PE. FIG. 14 demonstrates the results of FACS analysis of monobody constructs in comparison with standard 1D9 antibody. The similar binding profiles suggest that the variable regions of the monobody are able to fold correctly and bind to CCR2 as effectively as intact antibody.

All documents cited throughout this application including references, pending patent applications and published patents, are hereby expressly incorporated herein by reference in their entirety.

Although preferred embodiments of the invention have been described using specific terms, such description are for illustrative purposes only, and it is to be understood that changes and variations may be made without departing from the spirit or scope of the invention. Those skilled in the art will recognize, or be able to ascertain using no more than routine experimentation, many equivalents of the specific embodiments of the invention described herein. Such equivalents are intended to be encompassed by the following claims.

What is claimed is:

1. A DNA expression vector comprising a nucleic acid sequence encoding a human IgG1 heavy chain constant region sequence of SEQ ID NO: 10, and a nucleic acid sequence encoding a humanized 1D9 heavy chain variable region.

2. The expression vector of claim 1, further comprising a nucleic acid sequence encoding a human light chain constant region.

3. The expression vector of claim 2, wherein the human light chain constant region is a kappa light chain constant region.

4. The expression vector of claim 1, further comprising a nucleic acid sequence encoding a humanized 1D9 light chain variable region.

5. The expression vector of claim 4, further comprising a nucleic acid sequence encoding a human light chain constant region.

6. The expression vector of claim 5, wherein the human light chain constant region is a kappa light chain constant region.

7. The expression vector of claim 1, wherein the nucleic acid sequence comprises the heavy chain constant region encoding nucleotide sequence of SEQ ID NO: 9.

8. The expression vector of claim 3 or claim 6, wherein the nucleic acid sequence encodes the light chain constant region sequence of SEQ ID NO: 12.

9. The expression vector of claim 8, wherein the nucleic acid sequence comprises the light chain constant region encoding nucleotide sequence of SEQ ID NO: 11.

10. The expression vector of claim 1, wherein the nucleic acid sequence encoding the heavy chain constant region and the nucleic acid encoding the humanized heavy chain variable region are operably linked to a promoter selected from the group consisting of a EF-1a promoter, a CMV promoter, an SV40 promoter, and an adenovirus major late promoter.

11. The expression vector of claim 10, wherein the promoter is a EF-1a promoter.

12. The expression vector of claim 11, wherein the nucleic acid sequence encoding the heavy chain constant region and the nucleic acid sequence encoding the humanized heavy chain variable region are under control of the same promoter.

13. The expression vector of claim 11 or claim 12, wherein the vector further comprises a BGH poly A sequence.

14. The expression vector of claim 13, wherein the BGH polyA sequence is downstream from the sequence encoding the heavy chain constant region.

15. The expression vector of claim 1, further comprising a selectable marker gene.

16. The expression vector of claim 15, wherein the selectable marker gene is selected from the group consisting of a dihydrofolate reductase (DHFR) gene and a neo gene.

17. The expression vector of claim 1, wherein the expression vector comprises at least two marker genes and the marker genes are a DHFR gene and a neo gene.

18. The expression vector of claim 1, wherein the nucleic acid sequence encoding the heavy chain constant region further comprises an immunoglobulin leader sequence.

19. The expression vector of claim 3 or claim 6, wherein the nucleic acid sequence encoding the light chain constant region further comprises an immunoglobulin leader sequence.

20. The expression vector of claim 1, wherein the nucleic acid sequence encoding the humanized heavy chain variable region further comprises an immunoglobulin leader sequence.

21. The expression vector of claim 4 or claim 6, wherein the nucleic acid sequence encoding the humanized light chain variable region further comprises an immunoglobulin leader sequence.

22. A DNA expression vector comprising a nucleic acid sequence encoding the heavy chain constant region sequence of SEQ ID NO: 10, a nucleic acid sequence encoding a humanized 1D9 heavy chain variable region, a nucleic acid encoding the light chain constant region sequence of SEQ ID NO: 12, and a nucleic acid sequence encoding a humanized 1D9 light chain variable region.

23. The expression vector of claim 22, wherein the nucleic acid sequence encoding the heavy chain constant region and the nucleic acid sequence encoding the humanized heavy chain variable region are operably linked to an EF-1a promoter.

24. The expression vector of claim 22, wherein the nucleic acid sequence encoding the light chain constant region and the nucleic acid sequence encoding the humanized light chain variable region are operably linked to an EF-1a promoter.

25. The expression vector of claim 23, wherein the nucleic acid sequence encoding the light chain constant region and the nucleic acid sequence encoding the humanized light chain variable region are operably linked to an EF-1a promoter.

26. The expression vector of claim 22, claim 23, claim 24 or claim 25, wherein the vector further comprises a BGH poly A sequence.

27. The expression vector of claim 26, wherein the BGH polyA sequence is downstream from the sequence encoding the heavy chain constant region.

28. The expression vector of claim 22, further comprising a selectable marker gene.

29. The expression vector of claim 28, wherein the selectable marker is selected from the group consisting of a DHFR gene and a neo gene.

30. The expression vector of claim 22, wherein the nucleic acid encoding the humanized heavy chain variable region further comprises an immunoglobulin leader sequence.

31. The expression vector of claim 22, wherein the nucleic acid sequence encoding the humanized light chain variable region further comprises an immunoglobulin leader sequence.

32. A host cell comprising the expression vector of claim 1 or claim 22.

33. The cell of claim 32, wherein the cell is selected from the group consisting of a bacterial, a yeast and a mammalian cell.

34. The cell of claim 33, wherein the cell is a mammalian cell.

35. The cell of claim 34, wherein the mammalian cell is selected from the group consisting of a lymphocytic cell line, CHO, and COS cells.

36. The cell of claim 34, wherein the mammalian cell is a CHO cell.

37. The cell of claim 36, wherein the CHO cell is a DHFR deficient CHO cell.

* * * * *

UNITED STATES PATENT AND TRADEMARK OFFICE
CERTIFICATE OF CORRECTION

| | | |
|---|---|---|
| PATENT NO. | : 7,053,202 B2 | Page 1 of 1 |
| APPLICATION NO. | : 10/272899 | |
| DATED | : May 30, 2006 | |
| INVENTOR(S) | : Theresa O'Keefe et al. | |

It is certified that error appears in the above-identified patent and that said Letters Patent is hereby corrected as shown below:

Title Page item 56
Please add under References Cited – U.S. Patent Documents -- 2003/0165494 9/4/2003 LaRosa et al. --

Please add under References Cited – Foreign Patent Documents
-- AU 2003213475 8/14/2003
AU 2001233277 8/14/2001
AU 2004208716 9/23/2004
AU 600575 10/10/1988
JP 2003-521927 7/22/2003
JP 2002-521021 7/16/2002 --

In the claims section, Column 129, claim 16, line 16, replace "neo" with -- *neo* --

In the claims section, Column 130, claim 29, line 22, replace "neo" with -- *neo* --

Signed and Sealed this

Twenty-second Day of July, 2008

JON W. DUDAS
*Director of the United States Patent and Trademark Office*

```
                           SEQUENCE LISTING

<160> NUMBER OF SEQ ID NOS: 110

<210> SEQ ID NO 1
<211> LENGTH: 99
<212> TYPE: DNA
<213> ORGANISM: Artificial Sequence
<220> FEATURE:
<223> OTHER INFORMATION: immunoglobulin variable heavy leader sequence

<400> SEQUENCE: 1
ccgaattcct caccatggct gtcttggggc tgctcttctg cctggtgact ttacccaatt      60
gtgtcctgtc cagactagtc acagtcagct cagcctcca                            99

<210> SEQ ID NO 2
<211> LENGTH: 19
<212> TYPE: PRT
<213> ORGANISM: Artificial Sequence
<220> FEATURE:
<223> OTHER INFORMATION: immunoglobulin variable heavy leader sequence

<400> SEQUENCE: 2

Met Ala Val Leu Gly Leu Leu Phe Cys Leu Val Thr Leu Pro Asn Cys
 1               5                  10                  15

Val Leu Ser

<210> SEQ ID NO 3
<211> LENGTH: 110
<212> TYPE: DNA
<213> ORGANISM: Artificial Sequence
<220> FEATURE:
<223> OTHER INFORMATION: immunoglobulin variable kappa leader sequence

<400> SEQUENCE: 3
atatgcggcc gcctcaccat ggacatgagg gtgcccgcgc agctcctggg gctgctgctg      60
ctctggttcc cagggtcccg ttccagctgg agatcaaagc gtacggtggc                110

<210> SEQ ID NO 4
```

```
<211> LENGTH: 22
<212> TYPE: PRT
<213> ORGANISM: Artificial Sequence
<220> FEATURE:
<223> OTHER INFORMATION: immunoglobulin variable kappa leader sequence

<400> SEQUENCE: 4

Met Asp Met Arg Val Pro Ala Gln Leu Leu Gly Leu Leu Leu Leu Trp
 1               5                  10                  15

Phe Pro Gly Ser Arg Ser
            20

<210> SEQ ID NO 5
<211> LENGTH: 114
<212> TYPE: DNA
<213> ORGANISM: Artificial Sequence
<220> FEATURE:
<223> OTHER INFORMATION: immunoglobulin variable lambda leader sequence

<400> SEQUENCE: 5
atatgcggcc gcctcaccat ggacatgagg gtgcccgcgc agctcctggg gctgctgctg      60
ctctggttcc cagggtcccg ttccagctgg agatcaaagt taaccgtcct aggt           114

<210> SEQ ID NO 6
<211> LENGTH: 22
<212> TYPE: PRT
<213> ORGANISM: Artificial Sequence
<220> FEATURE:
<223> OTHER INFORMATION: immunoglobulin variable lambda leader sequence

<400> SEQUENCE: 6

Met Asp Met Arg Val Pro Ala Gln Leu Leu Gly Leu Leu Leu Leu Trp
 1               5                  10                  15

Phe Pro Gly Ser Arg Ser
            20

<210> SEQ ID NO 7
<211> LENGTH: 1012
<212> TYPE: DNA
<213> ORGANISM: Artificial Sequence
<220> FEATURE:
<223> OTHER INFORMATION: human IgG1-WT DNA

<400> SEQUENCE: 7
agtcagctca gcctccacca agggcccatc ggtcttcccc ctggcaccct cctccaagag      60
cacctctggg ggcacagcgg ccctgggctg cctggtcaag gactacttcc ccgaaccggt     120
gacggtgtcg tggaactcag gcgccctgac cagcggcgtg cacaccttcc cggctgtcct     180
acagtcctca ggactctact ccctcagcag cgtggtgacc gtgccctcca gcagcttggg     240
cacccagacc tacatctgca acgtgaatca caagcccagc aacaccaagg tggacaagaa     300
agttgagccc aaatcttgtg acaaaactca cacatgccca ccgtgcccag cacctgaact     360 cctggggggga ccgtcagtct tcctcttccc cccaaaaccc aaggacaccc tcatgatctc     420
ccggacccct gaggtcacat gcgtggtggt ggacgtgagc cacgaagacc ctgaggtcaa     480
gttcaactgg tacgtggacg gcgtggaggt gcataatgcc aagacaaagc cgcgggagga     540
gcagtacaac agcacgtacc gtgtggtcag cgtcctcacc gtcctgcacc aggactggct     600
gaatggcaag gagtacaagt gcaaggtctc caacaaagcc ctcccagccc ccatcgagaa     660
aaccatctcc aaagccaaag ggcagccccg agaaccacag gtgtacaccc tgcccccatc     720
ccgggatgag ctgaccaaga accaggtcag cctgacctgc ctggtcaaag gcttctatcc     780
```

```
cagcgacatc gccgtggagt gggagagcaa tgggcagccg agaacaact acaagaccac    840 gcctcccgtg ctggactccg acggctcctt cttcctctac agcaagctca ccgtggacaa    900
gagcaggtgg cagcagggga acgtcttctc atgctccgtg atgcatgagg ctctgcacaa    960
ccactacacg cagaagagcc tctccctgtc tccgggtaaa taatctagag ca            1012
```

<210> SEQ ID NO 8
<211> LENGTH: 333
<212> TYPE: PRT
<213> ORGANISM: Artificial Sequence
<220> FEATURE:
<223> OTHER INFORMATION: human IgG1-WT protein

<400> SEQUENCE: 8

```
Val Ser Ser Ala Ser Thr Lys Gly Pro Ser Val Phe Pro Leu Ala Pro
1               5                   10                  15

Ser Ser Lys Ser Thr Ser Gly Gly Thr Ala Ala Leu Gly Cys Leu Val
            20                  25                  30

Lys Asp Tyr Phe Pro Glu Pro Val Thr Val Ser Trp Asn Ser Gly Ala
        35                  40                  45

Leu Thr Ser Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Gln Thr Tyr Ile Cys Asn Val Asn His Lys Pro Ser Asn Thr Lys
                85                  90                  95

Val Asp Lys Lys Val Glu Pro Lys Ser Cys Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320
```

-continued

His Tyr Thr Gln Lys Ser Leu Ser Leu Ser Pro Gly Lys
                325                 330

<210> SEQ ID NO 9
<211> LENGTH: 1012
<212> TYPE: DNA
<213> ORGANISM: Artificial Sequence
<220> FEATURE:
<223> OTHER INFORMATION: human IgG1-FcRmut DNA

<400> SEQUENCE: 9

```
agtcagctca gcctccacca agggcccatc ggtcttcccc ctggcaccct cctccaagag      60
cacctctggg ggcacagcgg ccctgggctg cctggtcaag gactacttcc ccgaaccggt     120
gacggtgtcg tggaactcag gcgccctgac cagcggcgtg cacaccttcc cggctgtcct     180
acagtcctca ggactctact ccctcagcag cgtggtgacc gtgccctcca gcagcttggg     240
cacccagacc tacatctgca acgtgaatca caagcccagc aacaccaagg tggacaagaa     300
agttgagccc aaatcttgtg acaaaactca cacatgccca ccgtgcccag cacctgaact     360
cgcggggca  ccgtcagtct tcctcttccc cccaaaaccc aaggacaccc tcatgatctc     420
ccggacccct gaggtcacat gcgtggtggt ggacgtgagc cacgaagacc ctgaggtcaa     480
gttcaactgg tacgtggacg gcgtggaggt gcataatgcc aagacaaagc cgcgggagga     540
gcagtacaac agcacgtacc gtgtggtcag cgtcctcacc gtcctgcacc aggactggct     600
gaatggcaag gagtacaagt gcaaggtctc caacaaagcc ctcccagccc ccatcgagaa     660
aaccatctcc aaagccaaag ggcagccccg agaaccacag gtgtacaccc tgcccccatc     720
ccgggatgag ctgaccaaga accaggtcag cctgacctgc ctggtcaaag gcttctatcc     780
cagcgacatc gccgtggagt gggagagcaa tgggcagccg gagaacaact acaagaccac     840
gcctcccgtg ctggactccg acggctcctt cttcctctac agcaagctca ccgtggacaa     900
gagcaggtgg cagcagggga acgtcttctc atgctccgtg atgcatgagg ctctgcacaa     960
ccactacacg cagaagagcc tctccctgtc tccgggtaaa taatctagag ca            1012
```

<210> SEQ ID NO 10
<211> LENGTH: 333
<212> TYPE: PRT
<213> ORGANISM: Artificial Sequence
<220> FEATURE:
<223> OTHER INFORMATION: human IgG1-FcRmut protein

<400> SEQUENCE: 10

Val Ser Ser Ala Ser Thr Lys Gly Pro Ser Val Phe Pro Leu Ala Pro
1               5                   10                  15

Ser Ser Lys Ser Thr Ser Gly Gly Thr Ala Ala Leu Gly Cys Leu Val
            20                  25                  30

Lys Asp Tyr Phe Pro Glu Pro Val Thr Val Ser Trp Asn Ser Gly Ala
        35                  40                  45

Leu Thr Ser Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Gln Thr Tyr Ile Cys Asn Val Asn His Lys Pro Ser Asn Thr Lys
                85                  90                  95

Val Asp Lys Lys Val Glu Pro Lys Ser Cys Asp Lys Thr His Thr Cys
            100                 105                 110

Pro Pro Cys Pro Ala Pro Glu Leu Ala Gly Ala Pro Ser Val Phe Leu

```
                115             120                 125
Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
210                 215                 220

Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330

<210> SEQ ID NO 11
<211> LENGTH: 341
<212> TYPE: DNA
<213> ORGANISM: Artificial Sequence
<220> FEATURE:
<223> OTHER INFORMATION: human C Kappa DNA

<400> SEQUENCE: 11
tcaaagcgta cggtggctgc accatctgtc ttcatcttcc cgccatctga tgagcagttg      60
aaatctggaa ctgcctctgt tgtgtgcctg ctgaataact tctatcccag agaggccaaa     120
gtacagtgga aggtggataa cgccctccaa tcgggtaact cccaggagag tgtcacagag     180
caggacagca aggacagcac ctacagcctc agcagcaccc tgaccctgag caaagcagac     240
tacgagaaac acaaagtcta cgcctgcgaa gtcacccatc agggcctgag ctcgcccgtc     300
acaaagagct tcaacagggg agagtgttag tctagagcag c                         341

<210> SEQ ID NO 12
<211> LENGTH: 109
<212> TYPE: PRT
<213> ORGANISM: Artificial Sequence
<220> FEATURE:
<223> OTHER INFORMATION: human C Kappa protein

<400> SEQUENCE: 12

Ser Lys Arg Thr Val Ala Ala Pro Ser Val Phe Ile Phe Pro Pro Ser
  1               5                  10                  15

Asp Glu Gln Leu Lys Ser Gly Thr Ala Ser Val Val Cys Leu Leu Asn
            20                  25                  30
```

```
Asn Phe Tyr Pro Arg Glu Ala Lys Val Gln Trp Lys Val Asp Asn Ala
         35                  40                  45

Leu Gln Ser Gly Asn Ser Gln Glu Ser Val Thr Glu Gln Asp Ser Lys
 50                  55                  60

Asp Ser Thr Tyr Ser Leu Ser Ser Thr Leu Thr Leu Ser Lys Ala Asp
 65                  70                  75                  80

Tyr Glu Lys His Lys Val Tyr Ala Cys Glu Val Thr His Gln Gly Leu
                 85                  90                  95

Ser Ser Pro Val Thr Lys Ser Phe Asn Arg Gly Glu Cys
            100                 105
```

<210> SEQ ID NO 13
<211> LENGTH: 360
<212> TYPE: DNA
<213> ORGANISM: Artificial Sequence
<220> FEATURE:
<223> OTHER INFORMATION: human C Lambda DNA

<400> SEQUENCE: 13

```
ataagaatgc ggccgcaagt taaccgtcct aggtcagccc aaggctgccc cctcggtcac    60
tctgttcccg ccctcctctg aggagcttca agccaacaag gccacactgg tgtgtctcat   120
aagtgacttc tacccgggag ccgtgacagt ggcctggaag gcagatagca gccccgtcaa   180
ggcgggagtg gagaccacca cccctccaa acaaagcaac aacaagtacg cggccagcag   240
ctatctgagc ctgacgcctg agcagtggaa gtcccacaga gctacagct gccaggtcac   300
gcatgaaggg agcaccgtgg agaagacagt ggcccctaca gaatgttcat agtctagagc   360
```

<210> SEQ ID NO 14
<211> LENGTH: 111
<212> TYPE: PRT
<213> ORGANISM: Artificial Sequence
<220> FEATURE:
<223> OTHER INFORMATION: human C Lambda protein

<400> SEQUENCE: 14

```
Lys Leu Thr Val Leu Gly Gln Pro Lys Ala Ala Pro Ser Val Thr Leu
 1               5                  10                  15

Phe Pro Pro Ser Ser Glu Glu Leu Gln Ala Asn Lys Ala Thr Leu Val
                 20                  25                  30

Cys Leu Ile Ser Asp Phe Tyr Pro Gly Ala Val Thr Val Ala Trp Lys
             35                  40                  45

Ala Asp Ser Ser Pro Val Lys Ala Gly Val Glu Thr Thr Thr Pro Ser
 50                  55                  60

Lys Gln Ser Asn Asn Lys Tyr Ala Ala Ser Ser Tyr Leu Ser Leu Thr
 65                  70                  75                  80

Pro Glu Gln Trp Lys Ser His Arg Ser Tyr Ser Cys Gln Val Thr His
                 85                  90                  95

Glu Gly Ser Thr Val Glu Lys Thr Val Ala Pro Thr Glu Cys Ser
            100                 105                 110
```

<210> SEQ ID NO 15
<211> LENGTH: 1029
<212> TYPE: DNA
<213> ORGANISM: Artificial Sequence
<220> FEATURE:
<223> OTHER INFORMATION: macaque IgG1-WT DNA

<400> SEQUENCE: 15

```
actagtcaca gtcagctcag cctccaccaa gggcccatcg gtcttccccc tggcgccctc    60
```

-continued

```
ctccaggagc acctccgaga gcacagcggc cctgggctgc ctggtcaagg actacttccc    120
tgaacccgtg accgtgtcgt ggaactcagg ctccctgacc agcggcgtgc acaccttccc    180
ggctgtccta cagtcctcag ggctctactc cctcagcagc gtggtgaccg tgccctccag    240
cagcttgggc acccagacct acgtctgcaa cgtaaaccac aagcccagca acaccaaggt    300
ggacaagaga gttgagataa aacatgtgg tggtggcagc aaacctccca cgtgcccacc    360
gtgcccagca cctgaactcc tgggggggacc gtcagtcttc ctcttccccc caaaacccaa    420
ggacaccctc atgatctccc ggaccccctga ggtcacatgc gtggtggtag acgtgagcca    480
ggaagacccc gatgtcaagt tcaactggta cgtaaacggc gcggaggtgc atcatgccca    540
gacgaagcca cgggagacgc agtacaacag cacatatcgt gtggtcagcg tcctcaccgt    600
cacgcaccag gactggctga acggcaagga gtacacgtgc aaggtctcca acaaagccct    660
cccggccccc atccagaaaa ccatctccaa agacaaaggg cagccccgag agcctcaggt    720
gtacaccctg ccccgtccc gggaggagct gaccaagaac caggtcagcc tgacctgcct    780
ggtcaaaggc ttctacccca gcgacatcgt cgtggagtgg gagagcagcg gcagccggga    840
gaacacctac aagaccacgc cgcccgtgct ggactccgac ggctcctact cctctacag    900
caagctcacc gtggacaaga gcaggtggca gcagggaac gtcttctcat gctccgtgat    960
gcatgaggct ctgcacaacc actacaccca gaagagcctc tccctgtctc cgggtaaata   1020
atctagagc                                                          1029
```

<210> SEQ ID NO 16
<211> LENGTH: 339
<212> TYPE: PRT
<213> ORGANISM: Artificial Sequence
<220> FEATURE:
<223> OTHER INFORMATION: macaque IgG1-WT protein

<400> SEQUENCE: 16

```
Leu Val Thr Val Ser Ser Ala Ser Thr Lys Gly Pro Ser Val Phe Pro
  1               5                  10                  15

Leu Ala Pro Ser Ser Arg Ser Thr Ser Glu Ser Thr Ala Ala Leu Gly
                 20                  25                  30

Cys Leu Val Lys Asp Tyr Phe Pro Glu Pro Val Thr Val Ser Trp Asn
             35                  40                  45

Ser Gly Ser Leu Thr Ser Gly Val His Thr Phe Pro Ala Val Leu Gln
         50                  55                  60

Ser Ser Gly Leu Tyr Ser Leu Ser Ser Val Val Thr Val Pro Ser Ser
 65                  70                  75                  80

Ser Leu Gly Thr Gln Thr Tyr Val Cys Asn Val Asn His Lys Pro Ser
                 85                  90                  95

Asn Thr Lys Val Asp Lys Arg Val Glu Ile Lys Thr Cys Gly Gly Gly
            100                 105                 110

Ser Lys Pro Pro Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
    130                 135                 140

Ile Ser Arg Thr Pro Glu Val Thr Cys Val Val Val Asp Val Ser Gln
145                 150                 155                 160

Glu Asp Pro Asp Val Lys Phe Asn Trp Tyr Val Asn Gly Ala Glu Val
                165                 170                 175

His His Ala Gln Thr Lys Pro Arg Glu Thr Gln Tyr Asn Ser Thr Tyr
```

```
            180              185              190
Arg Val Val Ser Val Leu Thr Val Thr His Gln Asp Trp Leu Asn Gly
        195              200              205

Lys Glu Tyr Thr Cys Lys Val Ser Asn Lys Ala Leu Pro Ala Pro Ile
    210              215              220

Gln Lys Thr Ile Ser Lys Asp Lys Gly Gln Pro Arg Glu Pro Gln Val
225              230              235              240

Tyr Thr Leu Pro Pro Ser Arg Glu Glu Leu Thr Lys Asn Gln Val Ser
                245              250              255

Leu Thr Cys Leu Val Lys Gly Phe Tyr Pro Ser Asp Ile Val Val Glu
            260              265              270

Trp Glu Ser Ser Gly Gln Pro Glu Asn Thr Tyr Lys Thr Thr Pro Pro
        275              280              285

Val Leu Asp Ser Asp Gly Ser Tyr Phe Leu Tyr Ser Lys Leu Thr Val
    290              295              300

Asp Lys Ser Arg Trp Gln Gln Gly Asn Val Phe Ser Cys Ser Val Met
305              310              315              320

His Glu Ala Leu His Asn His Tyr Thr Gln Lys Ser Leu Ser Leu Ser
                325              330              335

Pro Gly Lys
```

<210> SEQ ID NO 17
<211> LENGTH: 1029
<212> TYPE: DNA
<213> ORGANISM: Artificial Sequence
<220> FEATURE:
<223> OTHER INFORMATION: macaque IgG1-FcRmut DNA

<400> SEQUENCE: 17

```
actagtcaca gtcagctcag cctccaccaa gggcccatcg gtcttccccc tggcgccctc      60
ctccaggagc acctccgaga gcacagcggc cctgggctgc ctggtcaagg actacttccc     120
tgaacccgtg accgtgtcgt ggaactcagg ctccctgacc agcggcgtgc acaccttccc     180
ggctgtccta cagtcctcag gctctactcc ctcagcagc gtggtgaccg tgccctccag     240
cagcttgggc acccagacct acgtctgcaa cgtaaaccac aagcccagca caccaaggt     300
ggacaagaga gttgagataa aacatgtgg tggtggcagc aaacctccca cgtgcccacc     360
gtgcccagca cctgaactcg cgggggcacc gtcagtcttc ctcttccccc caaaacccaa     420
ggacaccctc atgatctccc ggaccccga ggtcacatgc gtggtggtag acgtgagcca     480
ggaagacccc gatgtcaagt tcaactggta cgtaaacggc gcggaggtgc atcatgccca     540
gacgaagcca cggagacgc agtacaacag cacatatcgt gtggtcagcg tcctcaccgt     600
cacgcaccag gactggctga acggcaagga gtacacgtgc aaggtctcca acaaagccct     660
cccggccccc atccagaaaa ccatctccaa agacaaaggg cagccccgag agcctcaggt     720
gtacaccctg cccccgtccc gggaggagct gaccaagaac caggtcagcc tgacctgcct     780
ggtcaaaggc ttctaccca gcgacatcgt cgtggagtgg gagagcagcg ggcagccgga     840
gaacacctac aagaccacgc cgcccgtgct ggactccgac ggctcctact cctctacag     900
caagctcacc gtggacaaga gcaggtggca gcagggaac gtcttctcat gctccgtgat     960
gcatgaggct ctgcacaacc actacaccca gaagagcctc tccctgtctc cgggtaaata    1020
atctagagc                                                            1029
```

<210> SEQ ID NO 18

<211> LENGTH: 339
<212> TYPE: PRT
<213> ORGANISM: Artificial Sequence
<220> FEATURE:
<223> OTHER INFORMATION: macaque IgG1-FcRmut protein

<400> SEQUENCE: 18

```
Leu Val Thr Val Ser Ser Ala Ser Thr Lys Gly Pro Ser Val Phe Pro
 1               5                  10                  15

Leu Ala Pro Ser Ser Arg Ser Thr Ser Glu Ser Thr Ala Ala Leu Gly
                20                  25                  30

Cys Leu Val Lys Asp Tyr Phe Pro Glu Pro Val Thr Val Ser Trp Asn
            35                  40                  45

Ser Gly Ser Leu Thr Ser Gly Val His Thr Phe Pro Ala Val Leu Gln
    50                  55                  60

Ser Ser Gly Leu Tyr Ser Leu Ser Ser Val Val Thr Val Pro Ser Ser
65                  70                  75                  80

Ser Leu Gly Thr Gln Thr Tyr Val Cys Asn Val Asn His Lys Pro Ser
                85                  90                  95

Asn Thr Lys Val Asp Lys Arg Val Glu Ile Lys Thr Cys Gly Gly Gly
            100                 105                 110

Ser Lys Pro Pro Thr Cys Pro Pro Cys Pro Ala Pro Glu Leu Ala Gly
        115                 120                 125

Ala Pro Ser Val Phe Leu Phe Pro Pro Lys Pro Lys Asp Thr Leu Met
    130                 135                 140

Ile Ser Arg Thr Pro Glu Val Thr Cys Val Val Val Asp Val Ser Gln
145                 150                 155                 160

Glu Asp Pro Asp Val Lys Phe Asn Trp Tyr Val Asn Gly Ala Glu Val
                165                 170                 175

His His Ala Gln Thr Lys Pro Arg Glu Thr Gln Tyr Asn Ser Thr Tyr
            180                 185                 190

Arg Val Val Ser Val Leu Thr Val Thr His Gln Asp Trp Leu Asn Gly
        195                 200                 205

Lys Glu Tyr Thr Cys Lys Val Ser Asn Lys Ala Leu Pro Ala Pro Ile
    210                 215                 220

Gln Lys Thr Ile Ser Lys Asp Lys Gly Gln Pro Arg Glu Pro Gln Val
225                 230                 235                 240

Tyr Thr Leu Pro Pro Ser Arg Glu Glu Leu Thr Lys Asn Gln Val Ser
                245                 250                 255

Leu Thr Cys Leu Val Lys Gly Phe Tyr Pro Ser Asp Ile Val Val Glu
            260                 265                 270

Trp Glu Ser Ser Gly Gln Pro Glu Asn Thr Tyr Lys Thr Thr Pro Pro
        275                 280                 285

Val Leu Asp Ser Asp Gly Ser Tyr Phe Leu Tyr Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys
```

<210> SEQ ID NO 19
<211> LENGTH: 341
<212> TYPE: DNA
<213> ORGANISM: Artificial Sequence
<220> FEATURE:

<223> OTHER INFORMATION: macaque C Kappa DNA

<400> SEQUENCE: 19

```
gcggccgccg tacggtggct gcaccatctg tcttcatctt cccgccatct gaggatcagg    60
tgaaatctgg aactgtctct gttgtgtgcc tgctgaataa cttctatccc agagaggcca   120
gcgtaaagtg gaaggtggat ggtgccctca aaacggataa ctcccaggag agtgtcacag   180
agcaggacag caaggacaac acctacagcc tgagcagcac cctgacgttg agcagcacag   240
actaccagag tcacaatgtc tatgcctgcg aagtcaccca tcagggcctg agctcgcccg   300
tcaccaagag cttcaacagg ggagagtgtt agtctagagc a                       341
```

<210> SEQ ID NO 20
<211> LENGTH: 109
<212> TYPE: PRT
<213> ORGANISM: Artificial Sequence
<220> FEATURE:
<223> OTHER INFORMATION: macaque C Kappa protein

<400> SEQUENCE: 20

```
Gly Arg Arg Thr Val Ala Ala Pro Ser Val Phe Ile Phe Pro Pro Ser
 1               5                  10                  15

Glu Asp Gln Val Lys Ser Gly Thr Val Ser Val Val Cys Leu Leu Asn
             20                  25                  30

Asn Phe Tyr Pro Arg Glu Ala Ser Val Lys Trp Lys Val Asp Gly Ala
         35                  40                  45

Leu Lys Thr Asp Asn Ser Gln Glu Ser Val Thr Glu Gln Asp Ser Lys
     50                  55                  60

Asp Asn Thr Tyr Ser Leu Ser Ser Thr Leu Thr Leu Ser Ser Thr Asp
 65                  70                  75                  80

Tyr Gln Ser His Asn Val Tyr Ala Cys Glu Val Thr His Gln Gly Leu
                 85                  90                  95

Ser Ser Pro Val Thr Lys Ser Phe Asn Arg Gly Glu Cys
            100                 105
```

<210> SEQ ID NO 21
<211> LENGTH: 1027
<212> TYPE: DNA
<213> ORGANISM: Artificial Sequence
<220> FEATURE:
<223> OTHER INFORMATION: mouse IgG2a-WT DNA

<400> SEQUENCE: 21

```
agtcagctca gccaaaacaa cagccccatc ggtctatcca ctggcccctg tgtgtggagg    60
tacaactggc tcctcggtga ctctaggatg cctggtcaag ggttatttcc ctgagccagt   120
gaccttgacc tggaactctg gctccctgtc cagtggtgtg cacaccttcc cagctctcct   180
gcagtctggc ctctacaccc tcagcagctc agtgactgta acctcgaaca cctggcccag   240
ccagaccatc acctgcaatg tggcccaccc ggcaagcagc accaaagtgg acaagaaaat   300
tgagcccaga gtgcccataa cacagaaccc ctgtcctcca ctcaaagagt gtccccatg    360
cgcagctcca gacctcttgg gtggaccatc cgtcttcatc ttccctccaa agatcaagga   420
tgtactcatg atctccctga gccccatggt cacatgtgtg gtggtggatg tgagcgagga   480
tgacccagac gtccagatca gctggtttgt gaacaacgtg gaagtacaca cagctcagac   540
acaaacccat agagaggatt acaacagtac tctccgggtg gtcagtgccc tccccatcca   600
gcaccaggac tggatgagtg gcaaggagtt caaatgcaag gtcaacaaca gagccctccc   660
```

```
atcccccatc gagaaaacca tctcaaaacc cagagggcca gtaagagctc cacaggtata    720
tgtcttgcct ccaccagcag aagagatgac taagaaagag ttcagtctga cctgcatgat    780
cacaggcttc ttacctgccg aaattgctgt ggactggacc agcaatgggc gtacagagca    840
aaactacaag aacaccgcaa cagtcctgga ctctgatggt tcttacttca tgtacagcaa    900
gctcagagta caaagagca cttgggaaag aggaagtctt ttcgcctgct cagtggtcca    960
cgagggtctg cacaatcacc ttacgactaa gaccatctcc cggtctctgg gtaaataatc    1020
tagagca                                                              1027
```

<210> SEQ ID NO 22
<211> LENGTH: 338
<212> TYPE: PRT
<213> ORGANISM: Artificial Sequence
<220> FEATURE:
<223> OTHER INFORMATION: mouse IgG2a-WT protein

<400> SEQUENCE: 22

```
Val Ser Ser Ala Lys Thr Thr Ala Pro Ser Val Tyr Pro Leu Ala Pro
 1               5                  10                  15

Val Cys Gly Gly Thr Thr Gly Ser Ser Val Thr Leu Gly Cys Leu Val
            20                  25                  30

Lys Gly Tyr Phe Pro Glu Pro Val Thr Leu Thr Trp Asn Ser Gly Ser
        35                  40                  45

Leu Ser Ser Gly Val His Thr Phe Pro Ala Leu Leu Gln Ser Gly Leu
    50                  55                  60

Tyr Thr Leu Ser Ser Ser Val Thr Val Thr Ser Asn Thr Trp Pro Ser
65                  70                  75                  80

Gln Thr Ile Thr Cys Asn Val Ala His Pro Ala Ser Ser Thr Lys Val
                85                  90                  95

Asp Lys Lys Ile Glu Pro Arg Val Pro Ile Thr Gln Asn Pro Cys Pro
            100                 105                 110

Pro Leu Lys Glu Cys Pro Pro Cys Ala Ala Pro Asp Leu Leu Gly Gly
        115                 120                 125

Pro Ser Val Phe Ile Phe Pro Pro Lys Ile Lys Asp Val Leu Met Ile
    130                 135                 140

Ser Leu Ser Pro Met Val Thr Cys Val Val Asp Val Ser Glu Asp
145                 150                 155                 160

Asp Pro Asp Val Gln Ile Ser Trp Phe Val Asn Asn Val Glu Val His
                165                 170                 175

Thr Ala Gln Thr Gln Thr His Arg Glu Asp Tyr Asn Ser Thr Leu Arg
            180                 185                 190

Val Val Ser Ala Leu Pro Ile Gln His Gln Asp Trp Met Ser Gly Lys
        195                 200                 205

Glu Phe Lys Cys Lys Val Asn Asn Arg Ala Leu Pro Ser Pro Ile Glu
    210                 215                 220

Lys Thr Ile Ser Lys Pro Arg Gly Pro Val Arg Ala Pro Gln Val Tyr
225                 230                 235                 240

Val Leu Pro Pro Pro Ala Glu Glu Met Thr Lys Lys Glu Phe Ser Leu
                245                 250                 255

Thr Cys Met Ile Thr Gly Phe Leu Pro Ala Glu Ile Ala Val Asp Trp
            260                 265                 270

Thr Ser Asn Gly Arg Thr Glu Gln Asn Tyr Lys Asn Thr Ala Thr Val
        275                 280                 285

Leu Asp Ser Asp Gly Ser Tyr Phe Met Tyr Ser Lys Leu Arg Val Gln
```

```
                    290                 295                 300
Lys Ser Thr Trp Glu Arg Gly Ser Leu Phe Ala Cys Ser Val Val His
305                 310                 315                 320

Glu Gly Leu His Asn His Leu Thr Thr Lys Thr Ile Ser Arg Ser Leu
                325                 330                 335

Gly Lys

<210> SEQ ID NO 23
<211> LENGTH: 1027
<212> TYPE: DNA
<213> ORGANISM: Artificial Sequence
<220> FEATURE:
<223> OTHER INFORMATION: mouse IgG2a-FcRmut DNA

<400> SEQUENCE: 23
agtcagctca gccaaaacaa cagccccatc ggtctatcca ctggcccctg tgtgtggagg      60
tacaactggc tcctcggtga ctctaggatg cctggtcaag ggttatttcc ctgagccagt     120
gaccttgacc tggaactctg gctccctgtc cagtggtgtg cacaccttcc cagctctcct     180
gcagtctggc ctctacaccc tcagcagctc agtgactgta acctcgaaca cctggcccag     240
ccagaccatc acctgcaatg tggcccaccc ggcaagcagc accaaagtgg acaagaaaat     300
tgagcccaga gtgcccataa cacagaaccc ctgtcctcca ctcaaagagt gtccccatg     360 cgcagctcca gacctcgcag gtgcaccatc cgtcttcatc ttccctccaa agatcaagga     420
tgtactcatg atctccctga gcccatggt cacatgtgtg gtggtggatg tgagcgagga     480
tgacccagac gtccagatca gctggttgt gaacaacgtg gaagtacaca gctcagac      540 acaaacccat agagaggatt acaacagtac tctccgggtg gtcagtgccc tccccatcca     600
gcaccaggac tggatgagtg gcaaggcatt caatgcaag gtcaacaaca gagccctccc     660 atccccatc gagaaaacca tctcaaaacc cagagggcca gtaagagctc acaggtata      720 tgtcttgcct ccaccagcag aagagatgac taagaaagag ttcagtctga cctgcatgat     780
cacaggcttc ttacctgccg aaattgctgt ggactggacc agcaatgggc gtacagagca     840
aaactacaag aacaccgcaa cagtcctgga ctctgatggt tcttacttca gtacagcaa     900 gctcagagta caaagagca cttgggaaag aggaagtctt ttcgcctgct cagtggtcca     960
cgagggtctg cacaatcacc ttacgactaa gaccatctcc cggtctctgg gtaaataatc    1020
tagagca                                                               1027

<210> SEQ ID NO 24
<211> LENGTH: 338
<212> TYPE: PRT
<213> ORGANISM: Artificial Sequence
<220> FEATURE:
<223> OTHER INFORMATION: mouse IgG2a-FcRmut protein

<400> SEQUENCE: 24

Val Ser Ser Ala Lys Thr Thr Ala Pro Ser Val Tyr Pro Leu Ala Pro
1               5                   10                  15

Val Cys Gly Gly Thr Thr Gly Ser Ser Val Thr Leu Gly Cys Leu Val
                20                  25                  30

Lys Gly Tyr Phe Pro Glu Pro Val Thr Leu Thr Trp Asn Ser Gly Ser
            35                  40                  45

Leu Ser Ser Gly Val His Thr Phe Pro Ala Leu Leu Gln Ser Gly Leu
        50                  55                  60

Tyr Thr Leu Ser Ser Ser Val Thr Val Thr Ser Asn Thr Trp Pro Ser
```

-continued

```
            65                  70                  75                  80
        Gln Thr Ile Thr Cys Asn Val Ala His Pro Ala Ser Ser Thr Lys Val
                         85                  90                  95

Asp Lys Lys Ile Glu Pro Arg Val Pro Ile Thr Gln Asn Pro Cys Pro
                        100                 105                 110

Pro Leu Lys Glu Cys Pro Pro Cys Ala Ala Pro Asp Leu Ala Gly Ala
                        115                 120                 125

Pro Ser Val Phe Ile Phe Pro Pro Lys Ile Lys Asp Val Leu Met Ile
                        130                 135                 140

Ser Leu Ser Pro Met Val Thr Cys Val Val Asp Val Ser Glu Asp
        145                 150                 155                 160

Asp Pro Asp Val Gln Ile Ser Trp Phe Val Asn Asn Val Glu Val His
                        165                 170                 175

Thr Ala Gln Thr Gln Thr His Arg Glu Asp Tyr Asn Ser Thr Leu Arg
                        180                 185                 190

Val Val Ser Ala Leu Pro Ile Gln His Gln Asp Trp Met Ser Gly Lys
                        195                 200                 205

Ala Phe Lys Cys Lys Val Asn Asn Arg Ala Leu Pro Ser Pro Ile Glu
                        210                 215                 220

Lys Thr Ile Ser Lys Pro Arg Gly Pro Val Arg Ala Pro Gln Val Tyr
        225                 230                 235                 240

Val Leu Pro Pro Pro Ala Glu Glu Met Thr Lys Lys Glu Phe Ser Leu
                        245                 250                 255

Thr Cys Met Ile Thr Gly Phe Leu Pro Ala Glu Ile Ala Val Asp Trp
                        260                 265                 270

Thr Ser Asn Gly Arg Thr Glu Gln Asn Tyr Lys Asn Thr Ala Thr Val
                        275                 280                 285

Leu Asp Ser Asp Gly Ser Tyr Phe Met Tyr Ser Lys Leu Arg Val Gln
                        290                 295                 300

Lys Ser Thr Trp Glu Arg Gly Ser Leu Phe Ala Cys Ser Val Val His
        305                 310                 315                 320

Glu Gly Leu His Asn His Leu Thr Thr Lys Thr Ile Ser Arg Ser Leu
                        325                 330                 335

Gly Lys

<210> SEQ ID NO 25
<211> LENGTH: 347
<212> TYPE: DNA
<213> ORGANISM: Artificial Sequence
<220> FEATURE:
<223> OTHER INFORMATION: mouse C Kappa DNA

<400> SEQUENCE: 25
tcccagggtc cgttccgct gatgctgcac caactgtatc gatattccca ccatccagtg    60
agcagttaac atctggaggt gcctcagtcg tgtgcttctt gaacaacttc taccccaaag   120
acatcaatgt caagtggaag attgatggca gtgaacgaca aaatggcgtc ctgaacagtt   180
ggactgatca ggacagcaaa gacagcacct acagcatgag cagcaccctc acgttgacca   240
aggacgagta tgaacgacat aacagctata cctgtgaggc cactcacaag acatcaactt   300
cacccattgt caagagcttc aacaggaatg agtgttaatc tagagca               347

<210> SEQ ID NO 26
<211> LENGTH: 111
<212> TYPE: PRT
<213> ORGANISM: Artificial Sequence
```

-continued

```
<220> FEATURE:
<223> OTHER INFORMATION: mouse C Kappa protein

<400> SEQUENCE: 26

Pro Gly Ser Arg Ser Ala Asp Ala Ala Pro Thr Val Ser Ile Phe Pro
  1               5                  10                  15

Pro Ser Ser Glu Gln Leu Thr Ser Gly Gly Ala Ser Val Val Cys Phe
             20                  25                  30

Leu Asn Asn Phe Tyr Pro Lys Asp Ile Asn Val Lys Trp Lys Ile Asp
         35                  40                  45

Gly Ser Glu Arg Gln Asn Gly Val Leu Asn Ser Trp Thr Asp Gln Asp
     50                  55                  60

Ser Lys Asp Ser Thr Tyr Ser Met Ser Ser Thr Leu Thr Leu Thr Lys
 65                  70                  75                  80

Asp Glu Tyr Glu Arg His Asn Ser Tyr Thr Cys Glu Ala Thr His Lys
                 85                  90                  95

Thr Ser Thr Ser Pro Ile Val Lys Ser Phe Asn Arg Asn Glu Cys
            100                 105                 110

<210> SEQ ID NO 27
<211> LENGTH: 61
<212> TYPE: DNA
<213> ORGANISM: Artificial Sequence
<220> FEATURE:
<223> OTHER INFORMATION: primer pVHLa

<400> SEQUENCE: 27
ccgaattcct caccatggct gtcttggggc tgctcttctg cctggtgact ttacccaatt      60
g                                                                      61

<210> SEQ ID NO 28
<211> LENGTH: 62
<212> TYPE: DNA
<213> ORGANISM: Artificial Sequence
<220> FEATURE:
<223> OTHER INFORMATION: primer pVHLb

<400> SEQUENCE: 28
tggaggctga gctgactgtg actagtctgg acaggacaca attgggtaaa gtcaccaggc      60
ag                                                                     62

<210> SEQ ID NO 29
<211> LENGTH: 70
<212> TYPE: DNA
<213> ORGANISM: Artificial Sequence
<220> FEATURE:
<223> OTHER INFORMATION: primer pVKLa

<400> SEQUENCE: 29
atatgcggcc gcctcaccat ggacatgagg gtgcccgcgc agctcctggg gctgctgctg      60
ctctggttcc                                                             70

<210> SEQ ID NO 30
<211> LENGTH: 65
<212> TYPE: DNA
<213> ORGANISM: Artificial Sequence
<220> FEATURE:
<223> OTHER INFORMATION: primer pVKLb

<400> SEQUENCE: 30
gccaccgtac gctttgatct ccagctggaa cgggaccctg gaaccagag cagcagcagc       60
``` cccag                                                           65

<210> SEQ ID NO 31
<211> LENGTH: 21
<212> TYPE: DNA
<213> ORGANISM: Artificial Sequence
<220> FEATURE:
<223> OTHER INFORMATION: primer pVLLa5

<400> SEQUENCE: 31
atatgcggcc gcctcaccat g                                         21

<210> SEQ ID NO 32
<211> LENGTH: 35
<212> TYPE: DNA
<213> ORGANISM: Artificial Sequence
<220> FEATURE:
<223> OTHER INFORMATION: primer pVLLa3

<400> SEQUENCE: 32
acctaggacg gttaactttg atctccagct ggaac                          35

<210> SEQ ID NO 33
<211> LENGTH: 30
<212> TYPE: DNA
<213> ORGANISM: Artificial Sequence
<220> FEATURE:
<223> OTHER INFORMATION: primer pCHhum1
      human IgG1

<400> SEQUENCE: 33
agtcagctca gcctccacca agggcccatc                                30

<210> SEQ ID NO 34
<211> LENGTH: 37
<212> TYPE: DNA
<213> ORGANISM: Artificial Sequence
<220> FEATURE:
<223> OTHER INFORMATION: primer pCHhum2
      human IgG1

<400> SEQUENCE: 34
tgctctagat tatttacccg gagacaggga gaggctc                        37

<210> SEQ ID NO 35
<211> LENGTH: 40
<212> TYPE: DNA
<213> ORGANISM: Artificial Sequence
<220> FEATURE:
<223> OTHER INFORMATION: primer pCHhum3
      mutation of FcR region in human IgG1

<400> SEQUENCE: 35
ggaagactga cggtgccccc gcgagttcag gtgctgggca                     40

<210> SEQ ID NO 36
<211> LENGTH: 37
<212> TYPE: DNA
<213> ORGANISM: Artificial Sequence
<220> FEATURE:
<223> OTHER INFORMATION: primer pCHhum4
      mutation of FcR region in human IgG1

<400> SEQUENCE: 36
cctgaactcg cgggggcacc gtcagtcttc ctcttcc                        37

```
<210> SEQ ID NO 37
<211> LENGTH: 52
<212> TYPE: DNA
<213> ORGANISM: Artificial Sequence
<220> FEATURE:
<223> OTHER INFORMATION: primer pIgGrh1 macaque IgG1

<400> SEQUENCE: 37
actagtcaca gtcagctcag cctccaccaa gggcccatcg gtcttccccc tg          52

<210> SEQ ID NO 38
<211> LENGTH: 34
<212> TYPE: DNA
<213> ORGANISM: Artificial Sequence
<220> FEATURE:
<223> OTHER INFORMATION: primer pIgGrh4 macaque IgG1

<400> SEQUENCE: 38
gctctagatt atttacccgg agacagggag aggc                              34

<210> SEQ ID NO 39
<211> LENGTH: 47
<212> TYPE: DNA
<213> ORGANISM: Artificial Sequence
<220> FEATURE:
<223> OTHER INFORMATION: primer pIgGcy2 mutation of FcR region in
      macaque IgG1

<400> SEQUENCE: 39
ctgacggtgc ccccgcgagt tcaggtgctg ggcacggtgg gcacgtg                47

<210> SEQ ID NO 40
<211> LENGTH: 48
<212> TYPE: DNA
<213> ORGANISM: Artificial Sequence
<220> FEATURE:
<223> OTHER INFORMATION: primer pIgGcy3 mutation of FcR region in
      macaque IgG1

<400> SEQUENCE: 40
ccgtgcccag cacctgaact cgcgggggca ccgtcagtct tcctcttc               48

<210> SEQ ID NO 41
<211> LENGTH: 38
<212> TYPE: DNA
<213> ORGANISM: Artificial Sequence
<220> FEATURE:
<223> OTHER INFORMATION: primer pCHmur1 mouse IgG2a

<400> SEQUENCE: 41
agtcagctca gccaaaacaa cagccccatc ggtctatc                          38

<210> SEQ ID NO 42
<211> LENGTH: 37
<212> TYPE: DNA
<213> ORGANISM: Artificial Sequence
<220> FEATURE:
<223> OTHER INFORMATION: primer pCHmur4 mouse IgG2

<400> SEQUENCE: 42
tgctctagat tatttaccca gagaccggga gatggtc                           37

<210> SEQ ID NO 43
<211> LENGTH: 40
<212> TYPE: DNA
<213> ORGANISM: Artificial Sequence
```

<220> FEATURE:
<223> OTHER INFORMATION: primer pCHmur2 silent removal of mouse IgG
    2a BamHI site

<400> SEQUENCE: 43
ggtgtgcaca ccactggaca gggagccaga gttccaggtc         40

<210> SEQ ID NO 44
<211> LENGTH: 46
<212> TYPE: DNA
<213> ORGANISM: Artificial Sequence
<220> FEATURE:
<223> OTHER INFORMATION: primer pCHmur3 silent removal of mouse IgG
    2a BamHI site

<400> SEQUENCE: 44
ctctggctcc ctgtccagtg gtgtgcacac cttcccagct ctcctg         46

<210> SEQ ID NO 45
<211> LENGTH: 40
<212> TYPE: DNA
<213> ORGANISM: Artificial Sequence
<220> FEATURE:
<223> OTHER INFORMATION: primer pCHmur5 mutation first FcR region
    in mouse IgG2a

<400> SEQUENCE: 45
tgaagacgga tggtgcacct gcgaggtctg gagctgcgca         40

<210> SEQ ID NO 46
<211> LENGTH: 39
<212> TYPE: DNA
<213> ORGANISM: Artificial Sequence
<220> FEATURE:
<223> OTHER INFORMATION: primer pCHmur6 mutation first FcR region
    in mouse IgG2a

<400> SEQUENCE: 46
gacctcgcag gtgcaccatc cgtcttcatc ttccctcca         39

<210> SEQ ID NO 47
<211> LENGTH: 43
<212> TYPE: DNA
<213> ORGANISM: Artificial Sequence
<220> FEATURE:
<223> OTHER INFORMATION: primer pCHmur7 mutation second FcR region
    in mouse IgG2a

<400> SEQUENCE: 47
ccttgcattt gaatgccttg ccactcatcc agtcctggtg ctg         43

<210> SEQ ID NO 48
<211> LENGTH: 34
<212> TYPE: DNA
<213> ORGANISM: Artificial Sequence
<220> FEATURE:
<223> OTHER INFORMATION: primer pCHmur8 mutation second FcR region
    in mouse IgG2a

<400> SEQUENCE: 48
gtggcaaggc attcaaatgc aaggtcaaca acag         34

<210> SEQ ID NO 49
<211> LENGTH: 30
<212> TYPE: DNA
<213> ORGANISM: Artificial Sequence
<220> FEATURE:

<223> OTHER INFORMATION: primer pCK1 human C Kappa

<400> SEQUENCE: 49
tcaaagcgta cggtggctgc accatctgtc                              30

<210> SEQ ID NO 50
<211> LENGTH: 32
<212> TYPE: DNA
<213> ORGANISM: Artificial Sequence
<220> FEATURE:
<223> OTHER INFORMATION: primer pCK2 human C Kappa

<400> SEQUENCE: 50
gctgctctag actaacactc tccctgttg aa                            32

<210> SEQ ID NO 51
<211> LENGTH: 21
<212> TYPE: DNA
<213> ORGANISM: Artificial Sequence
<220> FEATURE:
<223> OTHER INFORMATION: primer pCK4 silent removal of human C Kappa
      BlpI site

<400> SEQUENCE: 51
gcaccctgac cctgagcaaa g                                       21

<210> SEQ ID NO 52
<211> LENGTH: 47
<212> TYPE: DNA
<213> ORGANISM: Artificial Sequence
<220> FEATURE:
<223> OTHER INFORMATION: primer pCL1 human C Lambda

<400> SEQUENCE: 52
ataagaatgc ggccgcaagt taaccgtcct aggtcagccc aaggctg           47

<210> SEQ ID NO 53
<211> LENGTH: 29
<212> TYPE: DNA
<213> ORGANISM: Artificial Sequence
<220> FEATURE:
<223> OTHER INFORMATION: primer pCL2 human C Lambda

<400> SEQUENCE: 53
gctctagact atgaacattc tgtaggggc                               29

<210> SEQ ID NO 54
<211> LENGTH: 32
<212> TYPE: DNA
<213> ORGANISM: Artificial Sequence
<220> FEATURE:
<223> OTHER INFORMATION: primer pIgKcy1 macaque C Kappa

<400> SEQUENCE: 54
gcggccgccg tacggtggct gcaccatctg tc                           32

<210> SEQ ID NO 55
<211> LENGTH: 34
<212> TYPE: DNA
<213> ORGANISM: Artificial Sequence
<220> FEATURE:
<223> OTHER INFORMATION: primer pIgKcy4 macaque C Kappa

<400> SEQUENCE: 55
tgctctagac taacactctc ccctgttgaa gctc                         34

-continued

<210> SEQ ID NO 56
<211> LENGTH: 37
<212> TYPE: DNA
<213> ORGANISM: Artificial Sequence
<220> FEATURE:
<223> OTHER INFORMATION: primer pIgKcy2 silent removal of macaque C
      Kappa BlpI restriction site

<400> SEQUENCE: 56
gtctgtgctg ctcaacgtca gggtgctgct caggctg                              37

<210> SEQ ID NO 57
<211> LENGTH: 34
<212> TYPE: DNA
<213> ORGANISM: Artificial Sequence
<220> FEATURE:
<223> OTHER INFORMATION: primer pIgKcy3 silent removal of macaque C
      Kappa BlpI restriction site

<400> SEQUENCE: 57
gcaccctgac gttgagcagc acagactacc agag                                 34

<210> SEQ ID NO 58
<211> LENGTH: 65
<212> TYPE: DNA
<213> ORGANISM: Artificial Sequence
<220> FEATURE:
<223> OTHER INFORMATION: primer pCKmur1mouse C Kappa

<400> SEQUENCE: 58
tcccagggtc ccgttccgct gatgctgcac caactgtatc gatattccca ccatccagtg     60
agcag                                                                 65

<210> SEQ ID NO 59
<211> LENGTH: 37
<212> TYPE: DNA
<213> ORGANISM: Artificial Sequence
<220> FEATURE:
<223> OTHER INFORMATION: primer pCKmur2 mouse C Kappa

<400> SEQUENCE: 59
tgctctagat taacactcat tcctgttgaa gctcttg                              37

<210> SEQ ID NO 60
<211> LENGTH: 43
<212> TYPE: DNA
<213> ORGANISM: Artificial Sequence
<220> FEATURE:
<223> OTHER INFORMATION: primer n1D9VH5

<400> SEQUENCE: 60
ttacccaatt gtgtcctgtc cgaggtgcag cttgttgagt ctg                       43

<210> SEQ ID NO 61
<211> LENGTH: 37
<212> TYPE: DNA
<213> ORGANISM: Artificial Sequence
<220> FEATURE:
<223> OTHER INFORMATION: primer n1D9VH3

<400> SEQUENCE: 61
gttttaggct gagctgacgg tgaccgtggt ccctgtg                              37

<210> SEQ ID NO 62
<211> LENGTH: 39

```
<212> TYPE: DNA
<213> ORGANISM: Artificial Sequence
<220> FEATURE:
<223> OTHER INFORMATION: primer n1D9VK5

<400> SEQUENCE: 62
ttcccagggt cccgttccga tgttgtgatg acccagact                           39

<210> SEQ ID NO 63
<211> LENGTH: 32
<212> TYPE: DNA
<213> ORGANISM: Artificial Sequence
<220> FEATURE:
<223> OTHER INFORMATION: primer n1D9VKhum3

<400> SEQUENCE: 63
agccaccgta cgctttattt ccagcttggt cc                                  32

<210> SEQ ID NO 64
<211> LENGTH: 56
<212> TYPE: DNA
<213> ORGANISM: Artificial Sequence
<220> FEATURE:
<223> OTHER INFORMATION: primer n1D9VKmur3

<400> SEQUENCE: 64
tgggaatatc gatacagttg gtgcagcatc agcacgcttt atttccagct tggtcc        56

<210> SEQ ID NO 65
<211> LENGTH: 434
<212> TYPE: DNA
<213> ORGANISM: Artificial Sequence
<220> FEATURE:
<223> OTHER INFORMATION: immunoglobulin cassette sequence Leader-HuCK_57

<400> SEQUENCE: 65
atatgcggcc gcctcaccat ggacatgagg gtgcccgcgc agctcctggg gctgctgctg     60
ctctggttcc cagggtcccg ttccagctgg agatcaaagc gtacggtggc tgcaccatct    120
gtcttcatct tcccgccatc tgatgagcag ttgaaatctg gaactgcctc tgttgtgtgc    180
ctgctgaata acttctatcc cagagaggcc aaagtacagt ggaaggtgga taacgccctc    240
caatcgggta actcccagga gagtgtcaca gagcaggaca gcaaggacag cacctacagc    300
ctcagcagca ccctgaccct gagcaaagca gactacgaga aacacaaagt ctacgcctgc    360
gaagtcaccc atcagggcct gagctcgccc gtcacaaaga gcttcaacag gggagagtgt    420
tagtctagag cagc                                                      434

<210> SEQ ID NO 66
<211> LENGTH: 134
<212> TYPE: PRT
<213> ORGANISM: Artificial Sequence
<220> FEATURE:
<223> OTHER INFORMATION: immunoglobulin cassette protein sequence
      Leader-HuCK_57

<400> SEQUENCE: 66

Met Asp Met Arg Val Pro Ala Gln Leu Leu Gly Leu Leu Leu Leu Trp
  1               5                  10                  15

Phe Pro Gly Ser Arg Ser Ser Trp Arg Ser Lys Arg Thr Val Ala Ala
                 20                  25                  30

Pro Ser Val Phe Ile Phe Pro Pro Ser Asp Glu Gln Leu Lys Ser Gly
             35                  40                  45
```

```
Thr Ala Ser Val Val Cys Leu Leu Asn Asn Phe Tyr Pro Arg Glu Ala
     50                  55                  60

Lys Val Gln Trp Lys Val Asp Asn Ala Leu Gln Ser Gly Asn Ser Gln
 65                  70                  75                  80

Glu Ser Val Thr Glu Gln Asp Ser Lys Asp Ser Thr Tyr Ser Leu Ser
                 85                  90                  95

Ser Thr Leu Thr Leu Ser Lys Ala Asp Tyr Glu Lys His Lys Val Tyr
             100                 105                 110

Ala Cys Glu Val Thr His Gln Gly Leu Ser Ser Pro Val Thr Lys Ser
         115                 120                 125

Phe Asn Arg Gly Glu Cys
    130
```

<210> SEQ ID NO 67
<211> LENGTH: 440
<212> TYPE: DNA
<213> ORGANISM: Artificial Sequence
<220> FEATURE:
<223> OTHER INFORMATION: immunoglobulin cassette sequence Leader-HuCL_72

<400> SEQUENCE: 67

```
atatgcggcc gcctcaccat ggacatgagg gtgcccgcgc agctcctggg gctgctgctg      60
ctctggttcc cagggtcccg ttccagctgg agatcaaagt taaccgtcct aggtcagccc     120
aaggctgccc cctcggtcac tctgttcccg ccctcctctg aggagcttca agccaacaag     180
gccacactgg tgtgtctcat aagtgacttc tacccgggag ccgtgacagt ggcctggaag     240
gcagatagca gccccgtcaa ggcgggagtg agaccacca cccctccaa acaaagcaac      300
aacaagtacg cggccagcag ctatctgagc ctgacgcctg agcagtggaa gtcccacaga     360
agctacagct gccaggtcac gcatgaaggg agcaccgtgg agaagacagt ggcccctaca     420
gaatgttcat agtctagagc                                                 440
```

<210> SEQ ID NO 68
<211> LENGTH: 137
<212> TYPE: PRT
<213> ORGANISM: Artificial Sequence
<220> FEATURE:
<223> OTHER INFORMATION: immunoglobulin cassette protein sequence
     Leader-HuCL_72

<400> SEQUENCE: 68

```
Met Asp Met Arg Val Pro Ala Gln Leu Leu Gly Leu Leu Leu Leu Trp
  1               5                  10                  15

Phe Pro Gly Ser Arg Ser Ser Trp Arg Ser Lys Leu Thr Val Leu Gly
             20                  25                  30

Gln Pro Lys Ala Ala Pro Ser Val Thr Leu Phe Pro Pro Ser Ser Glu
         35                  40                  45

Glu Leu Gln Ala Asn Lys Ala Thr Leu Val Cys Leu Ile Ser Asp Phe
     50                  55                  60

Tyr Pro Gly Ala Val Thr Val Ala Trp Lys Ala Asp Ser Ser Pro Val
 65                  70                  75                  80

Lys Ala Gly Val Glu Thr Thr Pro Ser Lys Gln Ser Asn Asn Lys
                 85                  90                  95

Tyr Ala Ala Ser Ser Tyr Leu Ser Leu Thr Pro Glu Gln Trp Lys Ser
             100                 105                 110

His Arg Ser Tyr Ser Cys Gln Val Thr His Glu Gly Ser Thr Val Glu
         115                 120                 125
```

-continued

Lys Thr Val Ala Pro Thr Glu Cys Ser
    130                 135

<210> SEQ ID NO 69
<211> LENGTH: 1094
<212> TYPE: DNA
<213> ORGANISM: Artificial Sequence
<220> FEATURE:
<223> OTHER INFORMATION: immunoglobulin cassette sequence Leader-
      HuFCRm_56

<400> SEQUENCE: 69

| | | |
|---|---|---|
| ccgaattcct caccatggct gtcttggggc tgctcttctg cctggtgact ttacccaatt | 60 |
| gtgtcctgtc cagactagtc acagtcagct cagcctccac caagggccca tcggtcttcc | 120 |
| ccctggcacc ctcctccaag agcacctctg ggggcacagc ggccctgggc tgcctggtca | 180 |
| aggactactt ccccgaaccg gtgacggtgt cgtggaactc aggcgccctg accagcggcg | 240 |
| tgcacacctt cccggctgtc ctacagtcct caggactcta ctccctcagc agcgtggtga | 300 |
| ccgtgccctc cagcagcttg ggcacccaga cctacatctg caacgtgaat cacaagccca | 360 |
| gcaacaccaa ggtggacaag aaagttgagc ccaaatcttg tgacaaaact cacacatgcc | 420 |
| caccgtgccc agcacctgaa ctcgcggggg caccgtcagt cttcctcttc cccccaaaac | 480 |
| ccaaggacac cctcatgatc tcccggaccc ctgaggtcac atgcgtggtg gtggacgtga | 540 |
| gccacgaaga ccctgaggtc aagttcaact ggtacgtgga cggcgtggag gtgcataatg | 600 |
| ccaagacaaa gccgcgggag gagcagtaca acagcacgta ccgtgtggtc agcgtcctca | 660 |
| ccgtcctgca ccaggactgg ctgaatggca aggagtacaa gtgcaaggtc tccaacaaag | 720 |
| ccctcccagc ccccatcgag aaaaccatct ccaaagccaa agggcagccc cgagaaccac | 780 |
| aggtgtacac cctgccccca tcccgggatg agctgaccaa gaaccaggtc agcctgacct | 840 |
| gcctggtcaa aggcttctat cccagcgaca tcgccgtgga gtgggagagc aatgggcagc | 900 |
| cggagaacaa ctacaagacc acgcctcccg tgctggactc cgacggctcc ttcttcctct | 960 |
| acagcaagct caccgtggac aagagcaggt ggcagcaggg gaacgtcttc tcatgctccg | 1020 |
| tgatgcatga ggctctgcac aaccactaca cgcagaagag cctctccctg tctccgggta | 1080 |
| aataatctag agca | 1094 |

<210> SEQ ID NO 70
<211> LENGTH: 356
<212> TYPE: PRT
<213> ORGANISM: Artificial Sequence
<220> FEATURE:
<223> OTHER INFORMATION: immunoglobulin cassette protein sequence
      Leader-HuFCRm_56

<400> SEQUENCE: 70

Met Ala Val Leu Gly Leu Leu Phe Cys Leu Val Thr Leu Pro Asn Cys
1               5                   10                  15

Val Leu Ser Arg Leu Val Thr Val Ser Ser Ala Ser Thr Lys Gly Pro
            20                  25                  30

Ser Val Phe Pro Leu Ala Pro Ser Ser Lys Ser Thr Ser Gly Gly Thr
        35                  40                  45

Ala Ala Leu Gly Cys Leu Val Lys Asp Tyr Phe Pro Glu Pro Val Thr
    50                  55                  60

Val Ser Trp Asn Ser Gly Ala Leu Thr Ser Gly Val His Thr Phe Pro
65                  70                  75                  80

Ala Val Leu Gln Ser Ser Gly Leu Tyr Ser Leu Ser Ser Val Val Thr

```
                  85                  90                  95
Val Pro Ser Ser Ser Leu Gly Thr Gln Thr Tyr Ile Cys Asn Val Asn
                100                 105                 110

His Lys Pro Ser Asn Thr Lys Val Asp Lys Lys Val Glu Pro Lys Ser
            115                 120                 125

Cys Asp Lys Thr His Thr Cys Pro Pro Cys Pro Ala Pro Glu Leu Ala
        130                 135                 140

Gly Ala Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 71
<211> LENGTH: 1094
<212> TYPE: DNA
<213> ORGANISM: Artificial Sequence
<220> FEATURE:
<223> OTHER INFORMATION: immunoglobulin cassette sequence Leader-HuWT_55

<400> SEQUENCE: 71
ccgaattcct caccatggct gtcttggggc tgctcttctg cctggtgact ttacccaatt      60
gtgtcctgtc cagactagtc acagtcagct cagcctccac caagggccca tcggtcttcc    120
ccctggcacc ctcctccaag agcacctctg gggcacagc ggcccctgggc tgcctggtca    180 aggactactt ccccgaaccg gtgacggtgt cgtggaactc aggcgccctg accagcggcg    240
tgcacacctt cccggctgtc ctacagtcct caggactcta ctccctcagc agcgtggtga    300
ccgtgccctc cagcagcttg ggcacccaga cctacatctg caacgtgaat cacaagccca    360
gcaacaccaa ggtggacaag aaagttgagc ccaaatcttg tgacaaaact cacacatgcc    420
caccgtgccc agcacctgaa ctcctggggg gaccgtcagt cttcctcttc cccccaaaac    480
```

```
ccaaggacac cctcatgatc tcccggaccc ctgaggtcac atgcgtggtg gtggacgtga      540
gccacgaaga ccctgaggtc aagttcaact ggtacgtgga cggcgtggag gtgcataatg      600
ccaagacaaa gccgcgggag gagcagtaca acagcacgta ccgtgtggtc agcgtcctca      660
ccgtcctgca ccaggactgg ctgaatggca aggagtacaa gtgcaaggtc tccaacaaag      720
ccctcccagc ccccatcgag aaaaccatct ccaaagccaa aggcagcccc gagaaccac       780 aggtgtacac cctgccccca tcccgggatg agctgaccaa gaaccaggtc agcctgacct      840
gcctggtcaa aggcttctat cccagcgaca tcgccgtgga gtgggagagc aatgggcagc      900
cggagaacaa ctacaagacc acgcctcccg tgctggactc cgacggctcc ttcttcctct      960
acagcaagct caccgtggac aagagcaggt ggcagcaggg gaacgtcttc tcatgctccg     1020
tgatgcatga ggctctgcac aaccactaca cgcagaagag cctctccctg tctccgggta     1080
aataatctag agca                                                       1094

<210> SEQ ID NO 72
<211> LENGTH: 356
<212> TYPE: PRT
<213> ORGANISM: Artificial Sequence
<220> FEATURE:
<223> OTHER INFORMATION: immunoglobulin cassette protein sequence
      Leader-HuWT_55

<400> SEQUENCE: 72

Met Ala Val Leu Gly Leu Leu Phe Cys Leu Val Thr Leu Pro Asn Cys
  1               5                  10                  15

Val Leu Ser Arg Leu Val Thr Val Ser Ser Ala Ser Thr Lys Gly Pro
             20                  25                  30

Ser Val Phe Pro Leu Ala Pro Ser Ser Lys Ser Thr Ser Gly Gly Thr
         35                  40                  45

Ala Ala Leu Gly Cys Leu Val Lys Asp Tyr Phe Pro Glu Pro Val Thr
     50                  55                  60

Val Ser Trp Asn Ser Gly Ala Leu Thr Ser Gly Val His Thr Phe Pro
 65                  70                  75                  80

Ala Val Leu Gln Ser Ser Gly Leu Tyr Ser Leu Ser Ser Val Val Thr
                 85                  90                  95

Val Pro Ser Ser Leu Gly Thr Gln Thr Tyr Ile Cys Asn Val Asn
            100                 105                 110

His Lys Pro Ser Asn Thr Lys Val Asp Lys Lys Val Glu Pro Lys Ser
        115                 120                 125

Cys Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
```

-continued

```
                245                 250                 255
Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
        290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355
```

<210> SEQ ID NO 73
<211> LENGTH: 432
<212> TYPE: DNA
<213> ORGANISM: Artificial Sequence
<220> FEATURE:
<223> OTHER INFORMATION: immunoglobulin cassette sequence Leader-MacCK_67

<400> SEQUENCE: 73

```
atatgcggcc gcctcaccat ggacatgagg gtgcccgcgc agctcctggg gctgctgctg      60
ctctggttcc cagggtcccg ttccagctgg agatcaaagc gtacggtggc tgcaccatct    120
gtcttcatct tcccgccatc tgaggatcag gtgaaatctg gaactgtctc tgttgtgtgc    180
ctgctgaata acttctatcc cagagaggcc agcgtaaagt ggaaggtgga tggtgccctc    240
aaaacggata ctcccagga gagtgtcaca gagcaggaca gcaaggacaa cacctacagc     300
ctgagcagca ccctgacgtt gagcagcaca gactaccaga gtcacaatgt ctatgcctgc    360
gaagtcaccc atcagggcct gagctcgccc gtcaccaaga gcttcaacag gggagagtgt    420
tagtctagag ca                                                        432
```

<210> SEQ ID NO 74
<211> LENGTH: 134
<212> TYPE: PRT
<213> ORGANISM: Artificial Sequence
<220> FEATURE:
<223> OTHER INFORMATION: immunoglobulin cassette protein sequence Leader-MacCK_67

<400> SEQUENCE: 74

```
Met Asp Met Arg Val Pro Ala Gln Leu Leu Gly Leu Leu Leu Leu Trp
1               5                   10                  15

Phe Pro Gly Ser Arg Ser Ser Trp Arg Ser Lys Arg Thr Val Ala Ala
            20                  25                  30

Pro Ser Val Phe Ile Phe Pro Pro Ser Glu Asp Gln Val Lys Ser Gly
        35                  40                  45

Thr Val Ser Val Val Cys Leu Leu Asn Asn Phe Tyr Pro Arg Glu Ala
    50                  55                  60

Ser Val Lys Trp Lys Val Asp Gly Ala Leu Lys Thr Asp Asn Ser Gln
65                  70                  75                  80

Glu Ser Val Thr Glu Gln Asp Ser Lys Asp Asn Thr Tyr Ser Leu Ser
                85                  90                  95
```

```
Ser Thr Leu Thr Leu Ser Ser Thr Asp Tyr Gln Ser His Asn Val Tyr
            100                 105                 110

Ala Cys Glu Val Thr His Gln Gly Leu Ser Ser Pro Val Thr Lys Ser
            115                 120                 125

Phe Asn Arg Gly Glu Cys
    130

<210> SEQ ID NO 75
<211> LENGTH: 1102
<212> TYPE: DNA
<213> ORGANISM: Artificial Sequence
<220> FEATURE:
<223> OTHER INFORMATION: immunoglobulin cassette sequence Leader-
      MacFCR_66

<400> SEQUENCE: 75
ccgaattcct caccatggct gtcttggggc tgctcttctg cctggtgact ttacccaatt     60
gtgtcctgtc cagactagtc acagtcagct cagcctccac caagggccca tcggtcttcc    120
ccctggcgcc ctcctccagg agcacctccg agagcacagc ggccctgggc tgcctggtca    180
aggactactt ccctgaaccc gtgaccgtgt cgtggaactc aggctccctg accagcggcg    240
tgcacacctt cccggctgtc ctacagtcct cagggctcta ctccctcagc agcgtggtga    300
ccgtgccctc cagcagcttg ggcacccaga cctacgtctg caacgtaaac cacaagccca    360
gcaacaccaa ggtggacaag agagttgaga taaaaacatg tggtggtggc agcaaacctc    420
ccacgtgccc accgtgccca gcacctgaac tcgcggggc accgtcagtc ttcctcttcc     480
ccccaaaacc caaggacacc ctcatgatct cccggacccc tgaggtcaca tgcgtggtgg    540
tagacgtgag ccaggaagac cccgatgtca agttcaactg gtacgtaaac ggcgcggagg    600
tgcatcatgc ccagacgaag ccacgggaga cgcagtacaa cagcacatat cgtgtggtca    660
gcgtcctcac cgtcacgcac caggactggc tgaacggcaa ggagtacacg tgcaaggtct    720
ccaacaaagc cctcccggcc cccatccaga aaccatctc caaagacaaa gggcagcccc     780
gagagcctca ggtgtacacc ctgccccccgt cccgggagga gctgaccaag aaccaggtca    840
gcctgacctg cctggtcaaa ggcttctacc ccagcgacat cgtcgtggag tgggagagca    900
gcgggcagcc ggagaacacc tacaagacca cgccgcccgt gctggactcc gacggctcct    960
acttcctcta cagcaagctc accgtggaca agagcaggtg gcagcagggg aacgtcttct   1020
catgctccgt gatgcatgag gctctgcaca accactacac ccagaagagc ctctccctgt   1080
ctccgggtaa ataatctaga gc                                            1102

<210> SEQ ID NO 76
<211> LENGTH: 359
<212> TYPE: PRT
<213> ORGANISM: Artificial Sequence
<220> FEATURE:
<223> OTHER INFORMATION: immunoglobulin cassette protein sequence
      Leader-MacFCR_66

<400> SEQUENCE: 76

Met Ala Val Leu Gly Leu Leu Phe Cys Leu Val Thr Leu Pro Asn Cys
  1               5                  10                  15

Val Leu Ser Arg Leu Val Thr Val Ser Ser Ala Ser Thr Lys Gly Pro
             20                  25                  30

Ser Val Phe Pro Leu Ala Pro Ser Ser Arg Ser Thr Ser Glu Ser Thr
         35                  40                  45

Ala Ala Leu Gly Cys Leu Val Lys Asp Tyr Phe Pro Glu Pro Val Thr
```

|     |     |     |     |     | 50  |     |     |     |     | 55  |     |     |     |     | 60  |     |
| --- | --- | --- | --- | --- | --- | --- | --- | --- | --- | --- | --- | --- | --- | --- | --- | --- |

Val Ser Trp Asn Ser Gly Ser Leu Thr Ser Gly Val His Thr Phe Pro
65                  70                  75                  80

Ala Val Leu Gln Ser Ser Gly Leu Tyr Ser Leu Ser Ser Val Val Thr
                  85                  90                  95

Val Pro Ser Ser Ser Leu Gly Thr Gln Thr Tyr Val Cys Asn Val Asn
        100                  105                110

His Lys Pro Ser Asn Thr Lys Val Asp Lys Arg Val Glu Ile Lys Thr
        115                  120                125

Cys Gly Gly Ser Lys Pro Pro Thr Cys Pro Pro Cys Pro Ala Pro
130                  135                  140

Glu Leu Ala Gly Ala Pro Ser Val Phe Leu Phe Pro Pro Lys Pro Lys
145                  150                  155                160

Asp Thr Leu Met Ile Ser Arg Thr Pro Glu Val Thr Cys Val Val Val
        165                  170                175

Asp Val Ser Gln Glu Asp Pro Asp Val Lys Phe Asn Trp Tyr Val Asn
        180                  185                190

Gly Ala Glu Val His His Ala Gln Thr Lys Pro Arg Glu Thr Gln Tyr
        195                  200                205

Asn Ser Thr Tyr Arg Val Val Ser Val Leu Thr Val Thr His Gln Asp
    210                  215                220

Trp Leu Asn Gly Lys Glu Tyr Thr Cys Lys Val Ser Asn Lys Ala Leu
225                  230                  235                240

Pro Ala Pro Ile Gln Lys Thr Ile Ser Lys Asp Lys Gly Gln Pro Arg
        245                  250                255

Glu Pro Gln Val Tyr Thr Leu Pro Pro Ser Arg Glu Glu Leu Thr Lys
        260                  265                270

Asn Gln Val Ser Leu Thr Cys Leu Val Lys Gly Phe Tyr Pro Ser Asp
    275                  280                285

Ile Val Val Glu Trp Glu Ser Ser Gly Gln Pro Glu Asn Thr Tyr Lys
    290                  295                300

Thr Thr Pro Pro Val Leu Asp Ser Asp Gly Ser Tyr Phe Leu Tyr Ser
305                  310                  315                320

Lys Leu Thr Val Asp Lys Ser Arg Trp Gln Gln Gly Asn Val Phe Ser
        325                  330                335

Cys Ser Val Met His Glu Ala Leu His Asn His Tyr Thr Gln Lys Ser
        340                  345                350

Leu Ser Leu Ser Pro Gly Lys
        355

<210> SEQ ID NO 77
<211> LENGTH: 414
<212> TYPE: DNA
<213> ORGANISM: Artificial Sequence
<220> FEATURE:
<223> OTHER INFORMATION: immunoglobulin cassette sequence Leader-MuCK_62

<400> SEQUENCE: 77

| | | |
|---|---|---|
| atatgcggcc gcctcaccat ggacatgagg gtgcccgcgc agctcctggg gctgctgctg | 60 |
| ctctggttcc cagggtcccg ttccgctgat gctgcaccaa ctgtatcgat attcccacca | 120 |
| tccagtgagc agttaacatc tggaggtgcc tcagtcgtgt gcttcttgaa caacttctac | 180 |
| cccaaagaca tcaatgtcaa gtggaagatt gatggcagtg aacgacaaaa tggcgtcctg | 240 |
| aacagttgga ctgatcagga cagcaaagac agcacctaca gcatgagcag caccctcacg | 300 |

| | |
|---|---|
| ttgaccaagg acgagtatga acgacataac agctatacct gtgaggccac tcacaagaca | 360 |
| tcaacttcac ccattgtcaa gagcttcaac aggaatgagt gttaatctag agca | 414 |

<210> SEQ ID NO 78
<211> LENGTH: 128
<212> TYPE: PRT
<213> ORGANISM: Artificial Sequence
<220> FEATURE:
<223> OTHER INFORMATION: immunoglobulin cassette protein sequence
      Leader-MuCK_62

<400> SEQUENCE: 78

```
Met Asp Met Arg Val Pro Ala Gln Leu Leu Gly Leu Leu Leu Leu Trp
  1               5                  10                  15

Phe Pro Gly Ser Arg Ser Ala Asp Ala Ala Pro Thr Val Ser Ile Phe
             20                  25                  30

Pro Pro Ser Ser Glu Gln Leu Thr Ser Gly Gly Ala Ser Val Val Cys
         35                  40                  45

Phe Leu Asn Asn Phe Tyr Pro Lys Asp Ile Asn Val Lys Trp Lys Ile
     50                  55                  60

Asp Gly Ser Glu Arg Gln Asn Gly Val Leu Asn Ser Trp Thr Asp Gln
 65                  70                  75                  80

Asp Ser Lys Asp Ser Thr Tyr Ser Met Ser Ser Thr Leu Thr Leu Thr
                 85                  90                  95

Lys Asp Glu Tyr Glu Arg His Asn Ser Tyr Thr Cys Glu Ala Thr His
                100                 105                 110

Lys Thr Ser Thr Ser Pro Ile Val Lys Ser Phe Asn Arg Asn Glu Cys
            115                 120                 125
```

<210> SEQ ID NO 79
<211> LENGTH: 1109
<212> TYPE: DNA
<213> ORGANISM: Artificial Sequence
<220> FEATURE:
<223> OTHER INFORMATION: immunoglobulin cassette sequence
      Leader-Mu_FCRII_61

<400> SEQUENCE: 79

| | |
|---|---|
| ccgaattcct caccatggct gtcttggggc tgctcttctg cctggtgact ttacccaatt | 60 |
| gtgtcctgtc cagactagtc acagtcagct cagccaaaac aacagcccca tcggtctatc | 120 |
| cactggcccc tgtgtgtgga ggtacaactg gctcctcggt gactctagga tgcctggtca | 180 |
| agggttattt ccctgagcca gtgaccttga cctggaactc tggctccctg tccagtggtg | 240 |
| tgcacacctt cccagctctc ctgcagtctg gcctctacac cctcagcagc tcagtgactg | 300 |
| taacctcgaa cacctggccc agccagacca tcacctgcaa tgtggcccac ccggcaagca | 360 |
| gcaccaaagt ggacaagaaa attgagccca gagtgcccat aacacagaac ccctgtcctc | 420 |
| cactcaaaga gtgtccccca tgcgcagctc agacctcgc aggtgcacca tccgtcttca | 480 |
| tcttccctcc aaagatcaag gatgtactca tgatctccct gagccccatg gtcacatgtg | 540 |
| tggtggtgga tgtgagcgag gatgacccag acgtccagat cagctggttt gtgaacaacg | 600 |
| tggaagtaca cacagctcag acacaaaccc atagagagga ttacaacagt actctccggg | 660 |
| tggtcagtgc cctccccatc agcaccagg actggatgag tggcaaggca ttcaaatgca | 720 |
| aggtcaacaa cagagccctc ccatccccca tcgagaaaac catctcaaaa cccagagggc | 780 |
| cagtaagagc tccacaggta tatgtcttgc ctccaccagc agaagagatg actaagaaag | 840 |
| agttcagtct gacctgcatg atcacaggct cttacctgc cgaaattgct gtggactgga | 900 |

```
ccagcaatgg gcgtacagag caaaactaca agaacaccgc aacagtcctg gactctgatg      960
gttcttactt catgtacagc aagctcagag tacaaaagag cacttgggaa agaggaagtc     1020
ttttcgcctg ctcagtggtc cacgagggtc tgcacaatca ccttacgact aagaccatct     1080
cccggtctct gggtaaataa tctagagca                                       1109
```

<210> SEQ ID NO 80
<211> LENGTH: 361
<212> TYPE: PRT
<213> ORGANISM: Artificial Sequence
<220> FEATURE:
<223> OTHER INFORMATION: immunoglobulin cassette protein sequence
      Leader-Mu_FCRII_61

<400> SEQUENCE: 80

```
Met Ala Val Leu Gly Leu Leu Phe Cys Leu Val Thr Leu Pro Asn Cys
  1               5                  10                  15

Val Leu Ser Arg Leu Val Thr Val Ser Ser Ala Lys Thr Thr Ala Pro
             20                  25                  30

Ser Val Tyr Pro Leu Ala Pro Val Cys Gly Gly Thr Thr Gly Ser Ser
         35                  40                  45

Val Thr Leu Gly Cys Leu Val Lys Gly Tyr Phe Pro Glu Pro Val Thr
     50                  55                  60

Leu Thr Trp Asn Ser Gly Ser Leu Ser Ser Gly Val His Thr Phe Pro
 65                  70                  75                  80

Ala Leu Leu Gln Ser Gly Leu Tyr Thr Leu Ser Ser Ser Val Thr Val
                 85                  90                  95

Thr Ser Asn Thr Trp Pro Ser Gln Thr Ile Thr Cys Asn Val Ala His
            100                 105                 110

Pro Ala Ser Ser Thr Lys Val Asp Lys Lys Ile Glu Pro Arg Val Pro
        115                 120                 125

Ile Thr Gln Asn Pro Cys Pro Pro Leu Lys Glu Cys Pro Pro Cys Ala
    130                 135                 140

Ala Pro Asp Leu Ala Gly Ala Pro Ser Val Phe Ile Phe Pro Pro Lys
145                 150                 155                 160

Ile Lys Asp Val Leu Met Ile Ser Leu Ser Pro Met Val Thr Cys Val
                165                 170                 175

Val Val Asp Val Ser Glu Asp Asp Pro Asp Val Gln Ile Ser Trp Phe
            180                 185                 190

Val Asn Asn Val Glu Val His Thr Ala Gln Thr Gln Thr His Arg Glu
        195                 200                 205

Asp Tyr Asn Ser Thr Leu Arg Val Val Ser Ala Leu Pro Ile Gln His
    210                 215                 220

Gln Asp Trp Met Ser Gly Lys Ala Phe Lys Cys Lys Val Asn Asn Arg
225                 230                 235                 240

Ala Leu Pro Ser Pro Ile Glu Lys Thr Ile Ser Lys Pro Arg Gly Pro
                245                 250                 255

Val Arg Ala Pro Gln Val Tyr Val Leu Pro Pro Ala Glu Glu Met
            260                 265                 270

Thr Lys Lys Glu Phe Ser Leu Thr Cys Met Ile Thr Gly Phe Leu Pro
        275                 280                 285

Ala Glu Ile Ala Val Asp Trp Thr Ser Asn Gly Arg Thr Glu Gln Asn
    290                 295                 300

Tyr Lys Asn Thr Ala Thr Val Leu Asp Ser Asp Gly Ser Tyr Phe Met
305                 310                 315                 320
```

Tyr Ser Lys Leu Arg Val Gln Lys Ser Thr Trp Glu Arg Gly Ser Leu
            325                 330                 335

Phe Ala Cys Ser Val Val His Glu Gly Leu His Asn His Leu Thr Thr
            340                 345                 350

Lys Thr Ile Ser Arg Ser Leu Gly Lys
            355                 360

<210> SEQ ID NO 81
<211> LENGTH: 1109
<212> TYPE: DNA
<213> ORGANISM: Artificial Sequence
<220> FEATURE:
<223> OTHER INFORMATION: immunoglobulin cassette sequence Leader-Mu_
      WT_60

<400> SEQUENCE: 81

| | | | | | |
|---|---|---|---|---|---|
| ccgaattcct | caccatggct | gtcttggggc | tgctcttctg | cctggtgact | ttacccaatt | 60 |
| gtgtcctgtc | agactagtc | acagtcagct | cagccaaaac | aacagcccca | tcggtctatc | 120 |
| cactggcccc | tgtgtgtgga | ggtacaactg | gctcctcggt | gactctagga | tgcctggtca | 180 |
| agggttattt | ccctgagcca | gtgaccttga | cctggaactc | tggctccctg | tccagtggtg | 240 |
| tgcacacctt | cccagctctc | ctgcagtctg | gcctctacac | cctcagcagc | tcagtgactg | 300 |
| taacctcgaa | cacctggccc | agccagacca | tcacctgcaa | tgtggcccac | ccggcaagca | 360 |
| gcaccaaagt | ggacaagaaa | attgagccca | gagtgcccat | aacacagaac | ccctgtcctc | 420 |
| cactcaaaga | gtgtccccca | tgcgcagctc | cagacctctt | gggtggacca | tccgtcttca | 480 |
| tcttccctcc | aaagatcaag | gatgtactca | tgatctccct | gagccccatg | gtcacatgtg | 540 |
| tggtggtgga | tgtgagcgag | gatgacccag | acgtccagat | cagctggttt | gtgaacaacg | 600 |
| tggaagtaca | cacagctcag | acacaaaccc | atagagagga | ttacaacagt | actctccggg | 660 |
| tggtcagtgc | cctccccatc | cagcaccagg | actggatgag | tggcaaggag | ttcaaatgca | 720 |
| aggtcaacaa | cagagccctc | ccatccccca | tcgagaaaac | catctcaaaa | cccagagggc | 780 |
| cagtaagagc | tccacaggta | tatgtcttgc | ctccaccagc | agaagagatg | actaagaaag | 840 |
| agttcagtct | gacctgcatg | atcacaggct | tcttacctgc | cgaaattgct | gtggactgga | 900 |
| ccagcaatgg | gcgtacagag | caaaactaca | agaacaccgc | aacagtcctg | gactctgatg | 960 |
| gttcttactt | catgtacagc | aagctcagag | tacaaaagag | cacttgggaa | agaggaagtc | 1020 |
| ttttcgcctg | ctcagtggtc | cacgagggtc | tgcacaatca | ccttacgact | aagaccatct | 1080 |
| cccggtctct | gggtaaataa | tctagagca | | | | 1109 |

<210> SEQ ID NO 82
<211> LENGTH: 361
<212> TYPE: PRT
<213> ORGANISM: Artificial Sequence
<220> FEATURE:
<223> OTHER INFORMATION: immunoglobulin cassette protein sequence
      Leader-Mu_WT_60

<400> SEQUENCE: 82

Met Ala Val Leu Gly Leu Leu Phe Cys Leu Val Thr Leu Pro Asn Cys
 1               5                  10                  15

Val Leu Ser Arg Leu Val Thr Val Ser Ser Ala Lys Thr Thr Ala Pro
            20                  25                  30

Ser Val Tyr Pro Leu Ala Pro Val Cys Gly Gly Thr Thr Gly Ser Ser
            35                  40                  45

```
Val Thr Leu Gly Cys Leu Val Lys Gly Tyr Phe Pro Glu Pro Val Thr
     50                  55                  60
Leu Thr Trp Asn Ser Gly Ser Leu Ser Ser Gly Val His Thr Phe Pro
 65                  70                  75                  80
Ala Leu Leu Gln Ser Gly Leu Tyr Thr Leu Ser Ser Val Thr Val
                 85                  90                  95
Thr Ser Asn Thr Trp Pro Ser Gln Thr Ile Thr Cys Asn Val Ala His
             100                 105                 110
Pro Ala Ser Ser Thr Lys Val Asp Lys Lys Ile Glu Pro Arg Val Pro
             115                 120                 125
Ile Thr Gln Asn Pro Cys Pro Pro Leu Lys Glu Cys Pro Pro Cys Ala
 130                 135                 140
Ala Pro Asp Leu Leu Gly Gly Pro Ser Val Phe Ile Phe Pro Pro Lys
145                 150                 155                 160
Ile Lys Asp Val Leu Met Ile Ser Leu Ser Pro Met Val Thr Cys Val
                165                 170                 175
Val Val Asp Val Ser Glu Asp Asp Pro Asp Val Gln Ile Ser Trp Phe
            180                 185                 190
Val Asn Asn Val Glu Val His Thr Ala Gln Thr Gln Thr His Arg Glu
        195                 200                 205
Asp Tyr Asn Ser Thr Leu Arg Val Val Ser Ala Leu Pro Ile Gln His
210                 215                 220
Gln Asp Trp Met Ser Gly Lys Glu Phe Lys Cys Lys Val Asn Asn Arg
225                 230                 235                 240
Ala Leu Pro Ser Pro Ile Glu Lys Thr Ile Ser Lys Pro Arg Gly Pro
                245                 250                 255
Val Arg Ala Pro Gln Val Tyr Val Leu Pro Pro Pro Ala Glu Glu Met
            260                 265                 270
Thr Lys Lys Glu Phe Ser Leu Thr Cys Met Ile Thr Gly Phe Leu Pro
        275                 280                 285
Ala Glu Ile Ala Val Asp Trp Thr Ser Asn Gly Arg Thr Glu Gln Asn
290                 295                 300
Tyr Lys Asn Thr Ala Thr Val Leu Asp Ser Asp Gly Ser Tyr Phe Met
305                 310                 315                 320
Tyr Ser Lys Leu Arg Val Gln Lys Ser Thr Trp Glu Arg Gly Ser Leu
                325                 330                 335
Phe Ala Cys Ser Val Val His Glu Gly Leu His Asn His Leu Thr Thr
            340                 345                 350
Lys Thr Ile Ser Arg Ser Leu Gly Lys
        355                 360
```

<210> SEQ ID NO 83
<211> LENGTH: 381
<212> TYPE: DNA
<213> ORGANISM: Artificial Sequence
<220> FEATURE:
<223> OTHER INFORMATION: variable insert sequence n1D9VH

<400> SEQUENCE: 83

| | | | | | | |
|---|---|---|---|---|---|---|
| ttacccaatt | gtgtcctgtc | cgaggtgcag | cttgttgagt | ctggaggagg | attggtgcag | 60 |
| cctaaagggt | cattgaaact | ctcatgtgca | gcctctggat | tcagcttcaa | tgcctacgcc | 120 |
| atgaactggg | tccgccaggc | tccaggaaag | ggtttggaat | gggttgctcg | cataagaact | 180 |
| aaaaataata | attatgcaac | atattatgcc | gattcagtga | agacagata | caccatctcc | 240 |
| agagatgatt | cagaaagtat | gctctttctg | caaatgaaca | acttgaaaac | tgaggacaca | 300 |

```
gccatgtatt actgtgtgac cttttacggt aacggtgtct ggggcacagg gaccacggtc    360
accgtcagct cagcctaaaa c                                              381
```

<210> SEQ ID NO 84
<211> LENGTH: 125
<212> TYPE: PRT
<213> ORGANISM: Artificial Sequence
<220> FEATURE:
<223> OTHER INFORMATION: variable insert protein sequence n1D9VH

<400> SEQUENCE: 84

```
Leu Pro Asn Cys Val Leu Ser Glu Val Gln Leu Val Glu Ser Gly Gly
 1               5                  10                  15

Gly Leu Val Gln Pro Lys Gly Ser Leu Lys Leu Ser Cys Ala Ala Ser
            20                  25                  30

Gly Phe Ser Phe Asn Ala Tyr Ala Met Asn Trp Val Arg Gln Ala Pro
        35                  40                  45

Gly Lys Gly Leu Glu Trp Val Ala Arg Ile Arg Thr Lys Asn Asn Asn
    50                  55                  60

Tyr Ala Thr Tyr Tyr Ala Asp Ser Val Lys Asp Arg Tyr Thr Ile Ser
65                  70                  75                  80

Arg Asp Asp Ser Glu Ser Met Leu Phe Leu Gln Met Asn Asn Leu Lys
                85                  90                  95

Thr Glu Asp Thr Ala Met Tyr Tyr Cys Val Thr Phe Tyr Gly Asn Gly
            100                 105                 110

Val Trp Gly Thr Gly Thr Thr Val Thr Val Ser Ser Ala
        115                 120                 125
```

<210> SEQ ID NO 85
<211> LENGTH: 366
<212> TYPE: DNA
<213> ORGANISM: Artificial Sequence
<220> FEATURE:
<223> OTHER INFORMATION: variable insert sequence n1D9VK human

<400> SEQUENCE: 85

```
ttcccagggt cccgttccga tgttgtgatg acccagactc cactcacttt gtcggttacc    60
gttggacacc cagcctccat ctcttgcaag tcaagtcaga gcctcttaga tagtgatgga   120
aagacatttt tgaattggtt gttacagagg ccaggccagt ctccaaagcg cctaatctat   180
ctggtgtcta aactggactc tggagtccct gacaggttca ctggcagtgg atcagggaca   240
gatttcacac tgaaaatcag cagagtggag gctgaggatt tgggagttta ttattgctgg   300
caaggtacac attttccgta cacgttcgga ggggggacca agctggaaat aaagcgtacg   360
gtggct                                                               366
```

<210> SEQ ID NO 86
<211> LENGTH: 122
<212> TYPE: PRT
<213> ORGANISM: Artificial Sequence
<220> FEATURE:
<223> OTHER INFORMATION: variable insert protein sequence n1D9VK hum

<400> SEQUENCE: 86

```
Phe Pro Gly Ser Arg Ser Asp Val Val Met Thr Gln Thr Pro Leu Thr
 1               5                  10                  15

Leu Ser Val Thr Val Gly His Pro Ala Ser Ile Ser Cys Lys Ser Ser
            20                  25                  30
```

```
Gln Ser Leu Leu Asp Ser Asp Gly Lys Thr Phe Leu Asn Trp Leu Leu
        35                  40                  45

Gln Arg Pro Gly Gln Ser Pro Lys Arg Leu Ile Tyr Leu Val Ser Lys
 50                  55                  60

Leu Asp Ser Gly Val Pro Asp Arg Phe Thr Gly Ser Gly Ser Gly Thr
 65                  70                  75                  80

Asp Phe Thr Leu Lys Ile Ser Arg Val Glu Ala Glu Asp Leu Gly Val
                 85                  90                  95

Tyr Tyr Cys Trp Gln Gly Thr His Phe Pro Tyr Thr Phe Gly Gly Gly
            100                 105                 110

Thr Lys Leu Glu Ile Lys Arg Thr Val Ala
        115                 120
```

```
<210> SEQ ID NO 87
<211> LENGTH: 390
<212> TYPE: DNA
<213> ORGANISM: Artificial Sequence
<220> FEATURE:
<223> OTHER INFORMATION: variable insert sequence n1D9VK-Mu

<400> SEQUENCE: 87
ttcccagggt cccgttccga tgttgtgatg acccagactc cactcacttt gtcggttacc      60
gttggacacc cagcctccat ctcttgcaag tcaagtcaga gcctcttaga tagtgatgga     120
aagacatttt tgaattggtt gttacagagg ccaggccagt ctccaaagcg cctaatctat     180
ctggtgtcta aactggactc tggagtccct gacaggttca ctggcagtgg atcagggaca     240
gatttcacac tgaaaatcag cagagtggag gctgaggatt tgggagttta ttattgctgg     300
caaggtacac attttccgta cacgttcgga gggggggacca agctggaaat aaagcgtgct     360
gatgctgcac caactgtatc gatattccca                                      390
```

```
<210> SEQ ID NO 88
<211> LENGTH: 130
<212> TYPE: PRT
<213> ORGANISM: Artificial Sequence
<220> FEATURE:
<223> OTHER INFORMATION: variable insert protein sequence n1D9VK-Mu

<400> SEQUENCE: 88

Phe Pro Gly Ser Arg Ser Asp Val Val Met Thr Gln Thr Pro Leu Thr
 1               5                  10                  15

Leu Ser Val Thr Val Gly His Pro Ala Ser Ile Ser Cys Lys Ser Ser
             20                  25                  30

Gln Ser Leu Leu Asp Ser Asp Gly Lys Thr Phe Leu Asn Trp Leu Leu
        35                  40                  45

Gln Arg Pro Gly Gln Ser Pro Lys Arg Leu Ile Tyr Leu Val Ser Lys
 50                  55                  60

Leu Asp Ser Gly Val Pro Asp Arg Phe Thr Gly Ser Gly Ser Gly Thr
 65                  70                  75                  80

Asp Phe Thr Leu Lys Ile Ser Arg Val Glu Ala Glu Asp Leu Gly Val
                 85                  90                  95

Tyr Tyr Cys Trp Gln Gly Thr His Phe Pro Tyr Thr Phe Gly Gly Gly
            100                 105                 110

Thr Lys Leu Glu Ile Lys Arg Ala Asp Ala Ala Pro Thr Val Ser Ile
        115                 120                 125

Phe Pro
130
```

<210> SEQ ID NO 89
<211> LENGTH: 50
<212> TYPE: DNA
<213> ORGANISM: Artificial Sequence
<220> FEATURE:
<223> OTHER INFORMATION: primer pMVa

<400> SEQUENCE: 89
gtcagctcag cttccaccaa gggcccatcg tcttccccc tggcgccctg            50

<210> SEQ ID NO 90
<211> LENGTH: 69
<212> TYPE: DNA
<213> ORGANISM: Artificial Sequence
<220> FEATURE:
<223> OTHER INFORMATION: primer pMVe

<400> SEQUENCE: 90
cgatccaccg ccccgctgc cacctccccc tgaaccccg cctccactac actctcccct    60
gttgaagct                                                          69

<210> SEQ ID NO 91
<211> LENGTH: 44
<212> TYPE: DNA
<213> ORGANISM: Artificial Sequence
<220> FEATURE:
<223> OTHER INFORMATION: primer pMVf

<400> SEQUENCE: 91
ggtggcagcg ggggcggtgg atcgtgccca ccgtgcccag cacc                   44

<210> SEQ ID NO 92
<211> LENGTH: 34
<212> TYPE: DNA
<213> ORGANISM: Artificial Sequence
<220> FEATURE:
<223> OTHER INFORMATION: primer pMVh

<400> SEQUENCE: 92
tttgggctcc ggacaccgcg ggcacgatcc accg                              34

<210> SEQ ID NO 93
<211> LENGTH: 35
<212> TYPE: DNA
<213> ORGANISM: Artificial Sequence
<220> FEATURE:
<223> OTHER INFORMATION: primer pMVm

<400> SEQUENCE: 93
cggtgccccg gccagttcag gagcggggca ccttg                             35

<210> SEQ ID NO 94
<211> LENGTH: 39
<212> TYPE: DNA
<213> ORGANISM: Artificial Sequence
<220> FEATURE:
<223> OTHER INFORMATION: primer pMVp

<400> SEQUENCE: 94
ggtgccccgc tcctgaactg gccggggcac cgtcagtct                         39

<210> SEQ ID NO 95
<211> LENGTH: 75
<212> TYPE: DNA
<213> ORGANISM: Artificial Sequence

```
<220> FEATURE:
<223> OTHER INFORMATION: primer pPr9a

<400> SEQUENCE: 95
tcgtgcccgc ggtgtccgga gcccaaatct tgtgacacac ctcccccgtg ccctagatgt      60
ccagagccga aatcg                                                       75

<210> SEQ ID NO 96
<211> LENGTH: 42
<212> TYPE: DNA
<213> ORGANISM: Artificial Sequence
<220> FEATURE:
<223> OTHER INFORMATION: primer pPr9b

<400> SEQUENCE: 96
cagggcggtg gagtgtcaca cgatttcggc tctggacatc ta                         42

<210> SEQ ID NO 97
<211> LENGTH: 41
<212> TYPE: DNA
<213> ORGANISM: Artificial Sequence
<220> FEATURE:
<223> OTHER INFORMATION: primer pPr9c

<400> SEQUENCE: 97
cactccaccg ccctgtccac gctgccctga accaaagagc t                          41

<210> SEQ ID NO 98
<211> LENGTH: 79
<212> TYPE: DNA
<213> ORGANISM: Artificial Sequence
<220> FEATURE:
<223> OTHER INFORMATION: primer pPr9d

<400> SEQUENCE: 98
cggtgccccg gccagttcag gagcggggca ccttggacat ggaggcggcg tatcgcagct      60
ctttggttca gggcagcgt                                                   79

<210> SEQ ID NO 99
<211> LENGTH: 30
<212> TYPE: DNA
<213> ORGANISM: Artificial Sequence
<220> FEATURE:
<223> OTHER INFORMATION: primer pPr9e

<400> SEQUENCE: 99
tcgtgcccgc ggtgtccgga gcccaaatct                                       30

<210> SEQ ID NO 100
<211> LENGTH: 24
<212> TYPE: DNA
<213> ORGANISM: Artificial Sequence
<220> FEATURE:
<223> OTHER INFORMATION: primer pPr9f

<400> SEQUENCE: 100
cggtgccccg gccagttcag gagc                                             24

<210> SEQ ID NO 101
<211> LENGTH: 19
<212> TYPE: PRT
<213> ORGANISM: murine

<400> SEQUENCE: 101
```

```
Met Ala Val Leu Gly Leu Leu Phe Cys Leu Val Thr Leu Pro Asn Cys
  1               5                  10                  15

Val Leu Ser
```

<210> SEQ ID NO 102
<211> LENGTH: 22
<212> TYPE: PRT
<213> ORGANISM: homo sapiens

<400> SEQUENCE: 102

```
Met Asp Met Arg Val Pro Ala Gln Leu Leu Gly Leu Leu Leu Leu Trp
  1               5                  10                  15

Phe Pro Gly Ser Arg Ser
            20
```

<210> SEQ ID NO 103
<211> LENGTH: 177
<212> TYPE: DNA
<213> ORGANISM: Artificial Sequence
<220> FEATURE:
<223> OTHER INFORMATION: new Pr9 sequence

<400> SEQUENCE: 103

```
tcgtgcccgc ggtgtccgga gcccaaatct tgtgacacac ctccccgtg ccctagatgt    60 ccagagccga atcgtgtga cactccaccg ccctgtccac gctgccctga accaaagagc   120
tgcgatacgc cgcctccatg tccaaggtgc cccgctcctg aactggccgg ggcaccg     177
```

<210> SEQ ID NO 104
<211> LENGTH: 59
<212> TYPE: PRT
<213> ORGANISM: Artificial Sequence
<220> FEATURE:
<223> OTHER INFORMATION: new Pr9 IgG3 hinge protein sequence

<400> SEQUENCE: 104

```
Ser Cys Pro Arg Cys Pro Glu Pro Lys Ser Cys Asp Thr Pro Pro Pro
  1               5                  10                  15

Cys Pro Arg Cys Pro Glu Pro Lys Ser Cys Asp Thr Pro Pro Pro Cys
                20                  25                  30

Pro Arg Cys Pro Glu Pro Lys Ser Cys Asp Thr Pro Pro Pro Cys Pro
            35                  40                  45

Arg Cys Pro Ala Pro Glu Leu Ala Gly Ala Pro
        50                  55
```

<210> SEQ ID NO 105
<211> LENGTH: 1152
<212> TYPE: DNA
<213> ORGANISM: Artificial Sequence
<220> FEATURE:
<223> OTHER INFORMATION: human IgG3 CH1-hinge-IgG1CH2CH3 DNA

<400> SEQUENCE: 105

```
gtcagctcag cttccaccaa gggcccatcg gtcttccccc tggcgccctg ctccaggagc    60
acctctgggg gcacagcggc cctgggctgc ctggtcaagg actacttccc cgaaccggtg   120
acggtgtcgt ggaactcagg cgccctgacc agcggcgtgc acaccttccc ggctgtccta   180
cagtcctcag gactctactc cctcagcagc gtggtgaccg tgccctccag cagcttgggc   240
acccagacct acacctgcaa cgtgaatcac aagcccagca acaccaaggt ggacaagaga   300
gttgagctca aaccccact tgtgtgacaca actcacacat gcccgcggtg cccagagccc   360
```

```
aaatcttgtg acacacctcc cccgtgccca cggtgcccag agcccaaatc ttgtgacaca      420
cctcccccat gcccacggtg cccagagccc aaatcttgtg acacacctcc cccgtgccca      480 aggtgcccg ctcctgaact ggccggggca ccgtcagtct tcctcttccc cccaaaaccc       540
aaggacaccc tcatgatctc ccggaccct gaggtcacat gcgtggtggt ggacgtgagc       600
cacgaagacc ctgaggtcaa gttcaactgg tacgtggacg gcgtggaggt gcataatgcc      660
aagacaaagc cgcggggagga gcagtacaac agcacgtacc gtgtggtcag cgtcctcacc     720
gtcctgcacc aggactggct gaatggcaag gagtacaagt gcaaggtctc caacaaagcc     780
ctcccagccc ccatcgagaa aaccatctcc aaagccaaag gcagccccg agaaccacag       840 gtgtacaccc tgcccccatc ccgggatgag ctgaccaaga accaggtcag cctgacctgc      900
ctggtcaaag gcttctatcc cagcgacatc gccgtggagt gggagagcaa tgggcagccg      960
gagaacaact acaagaccac gcctcccgtg ctggactccg acggctcctt cttcctctac     1020
agcaagctca ccgtggacaa gagcaggtgg cagcagggga acgtcttctc atgctccgtg     1080
atgcatgagg ctctgcacaa ccactacacg cagaagagcc tctccctgtc tccgggtaaa    1140
taatctagag ca                                                          1152

<210> SEQ ID NO 106
<211> LENGTH: 380
<212> TYPE: PRT
<213> ORGANISM: Artificial Sequence
<220> FEATURE:
<223> OTHER INFORMATION: human IgG3 CH1-hinge-IgG1CH2CH3 protein

<400> SEQUENCE: 106

Val Ser Ser Ala Ser Thr Lys Gly Pro Ser Val Phe Pro Leu Ala Pro
  1               5                  10                  15

Cys Ser Arg Ser Thr Ser Gly Gly Thr Ala Ala Leu Gly Cys Leu Val
                 20                  25                  30

Lys Asp Tyr Phe Pro Glu Pro Val Thr Val Ser Trp Asn Ser Gly Ala
             35                  40                  45

Leu Thr Ser Gly Val His Thr Phe Pro Ala Val Leu Gln Ser Ser Gly
         50                  55                  60

Leu Tyr Ser Leu Ser Ser Val Val Thr Val Pro Ser Ser Ser Leu Gly
 65                  70                  75                  80

Thr Gln Thr Tyr Thr Cys Asn Val Asn His Lys Pro Ser Asn Thr Lys
                 85                  90                  95

Val Asp Lys Arg Val Glu Leu Lys Thr Pro Leu Gly Asp Thr Thr His
            100                 105                 110

Thr Cys Pro Arg Cys Pro Glu Pro Lys Ser Cys Asp Thr Pro Pro Pro
        115                 120                 125

Cys Pro Arg Cys Pro Glu Pro Lys Ser Cys Asp Thr Pro Pro Pro Cys
    130                 135                 140

Pro Arg Cys Pro Glu Pro Lys Ser Cys Asp Thr Pro Pro Pro Cys Pro
145                 150                 155                 160

Arg Cys Pro Ala Pro Glu Leu Ala Gly Ala Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220
```

```
Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
            245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
370                 375                 380

<210> SEQ ID NO 107
<211> LENGTH: 1053
<212> TYPE: DNA
<213> ORGANISM: Artificial Sequence
<220> FEATURE:
<223> OTHER INFORMATION: humanCkappa-linker-IgG1 hinge-IgG1CH2CH3 DNA

<400> SEQUENCE: 107
tcaaagcgta cggtggctgc accatctgtc ttcatcttcc cgccatctga tgagcagttg      60
aaatctggaa ctgcctctgt tgtgtgcctg ctgaataact tctatcccag agaggccaaa     120
gtacagtgga aggtggataa cgccctccaa tcgggtaact cccaggagag tgtcacagag     180
caggacagca aggacagcac ctacagcctc agcagcaccc tgaccctgag caaagcagac     240
tacgagaaac acaaagtcta cgcctgcgaa gtcacccatc agggcctgag ctcgcccgtc     300
acaaagagct tcaacagggg agagtgtagt ggaggcgggg ttcaggggg agtggcagc      360
gggggcggtg gatcgtgccc accgtgccca gcacctgaac tcgcggggc accgtcagtc      420
ttcctcttcc cccaaaaacc caaggacacc ctcatgatct cccggacccc tgaggtcaca     480
tgcgtggtgg tggacgtgag ccacgaagac cctgaggtca agttcaactg gtacgtggac     540
ggcgtggagg tgcataatgc caagacaaag ccgcgggagg agcagtacaa cagcacgtac     600
cgtgtggtca gcgtcctcac cgtcctgcac caggactggc tgaatggcaa ggagtacaag     660
tgcaaggtct ccaacaaagc cctcccagcc ccatcgaga aaccatctc aaagccaaa      720
gggcagcccc gagaaccaca ggtgtacacc ctgcccccat cccgggatga gctgaccaag     780
aaccaggtca gcctgacctg cctggtcaaa ggcttctatc ccagcgacat cgccgtggag     840
tgggagagca atgggcagcc ggagaacaac tacaagacca cgcctcccgt gctggactcc     900
gacggctcct tcttcctcta cagcaagctc accgtggaca agagcaggtg gcagcagggg     960
aacgtcttct catgctccgt gatgcatgag gctctgcaca accactacac gcagaagagc    1020
ctctccctgt ctccgggtaa ataatctaga gca                                 1053

<210> SEQ ID NO 108
```

<211> LENGTH: 347
<212> TYPE: PRT
<213> ORGANISM: Artificial Sequence
<220> FEATURE:
<223> OTHER INFORMATION: humanCkappa-linker-IgG1 hinge-IgG1CH2CH3 protein

<400> SEQUENCE: 108

```
Ser Lys Arg Thr Val Ala Ala Pro Ser Val Phe Ile Phe Pro Pro Ser
 1               5                  10                  15

Asp Glu Gln Leu Lys Ser Gly Thr Ala Ser Val Val Cys Leu Leu Asn
            20                  25                  30

Asn Phe Tyr Pro Arg Glu Ala Lys Val Gln Trp Lys Val Asp Asn Ala
        35                  40                  45

Leu Gln Ser Gly Asn Ser Gln Glu Ser Val Thr Glu Gln Asp Ser Lys
    50                  55                  60

Asp Ser Thr Tyr Ser Leu Ser Ser Thr Leu Thr Leu Ser Lys Ala Asp
65                  70                  75                  80

Tyr Glu Lys His Lys Val Tyr Ala Cys Glu Val Thr His Gln Gly Leu
                85                  90                  95

Ser Ser Pro Val Thr Lys Ser Phe Asn Arg Gly Glu Cys Ser Gly Gly
            100                 105                 110

Gly Gly Ser Gly Gly Gly Gly Ser Gly Gly Gly Gly Ser Cys Pro Pro
        115                 120                 125

Cys Pro Ala Pro Glu Leu Ala Gly Ala Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Lys Phe Asn
                165                 170                 175

Trp Tyr Val Asp Gly Val Glu Val His Asn Ala Lys Thr Lys Pro Arg
            180                 185                 190

Glu Glu Gln Tyr Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Ala Leu Pro Ala Pro Ile Glu Lys Thr Ile Ser Lys Ala Lys
225                 230                 235                 240

Gly Gln Pro Arg Glu Pro Gln Val Tyr Thr Leu Pro Pro Ser Arg Asp
                245                 250                 255

Glu Leu Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345
```

<210> SEQ ID NO 109
<211> LENGTH: 1188
<212> TYPE: DNA

<213> ORGANISM: Artificial Sequence
<220> FEATURE:
<223> OTHER INFORMATION: humanCkappa-linker-IgG3 hinge-IgG1CH2CH3 DNA

<400> SEQUENCE: 109

```
tcaaagcgta cggtggctgc accatctgtc ttcatcttcc cgccatctga tgagcagttg      60
aaatctggaa ctgcctctgt tgtgtgcctg ctgaataact tctatcccag agaggccaaa     120
gtacagtgga aggtggataa cgccctccaa tcgggtaact cccaggagag tgtcacagag     180
caggacagca aggacagcac ctacagcctc agcagcaccc tgaccctgag caaagcagac     240
tacgagaaac acaaagtcta cgcctgcgaa gtcacccatc agggcctgag ctcgcccgtc     300
acaaagagct caacaggggg agagtgtagt ggaggcgggg gttcaggggg aggtggcagc     360
gggggcggtg gatcgtgccc gcggtgtccg gagcccaaat cttgtgacac acctcccccg     420
tgccctagat gtccagagcc gaaatcgtgt gacactccac cgccctgtcc acgctgccct     480
gaaccaaaga gctgcgatac gccgcctcca tgtccaaggt gccccgctcc tgaactggcc     540
ggggcaccgt cagtcttcct cttcccccca aaacccaagg acaccctcat gatctcccgg     600
accccctgagg tcacatgcgt ggtggtggac gtgagccacg aagaccctga ggtcaagttc     660
aactggtacg tggacggcgt ggaggtgcat aatgccaaga caaagccgcg ggaggagcag     720
tacaacagca cgtaccgtgt ggtcagcgtc ctcaccgtcc tgcaccagga ctggctgaat     780
ggcaaggagt acaagtgcaa ggtctccaac aaagccctcc cagcccccat cgagaaaacc     840
atctccaaag ccaagggca gccccgagaa ccacaggtgt acaccctgcc cccatcccgg     900
gatgagctga ccaagaacca ggtcagcctg acctgcctgg tcaaaggctt ctatcccagc     960
gacatcgccg tggagtggga gagcaatggg cagccggaga acaactacaa gaccacgcct    1020
cccgtgctgg actccgacgg ctccttcttc ctctacagca agctcaccgt ggacaagagc    1080
aggtggcagc aggggaacgt cttctcatgc tccgtgatgc atgaggctct gcacaaccac    1140
tacacgcaga agagcctctc cctgtctccg ggtaaataat ctagagca                 1188
```

<210> SEQ ID NO 110
<211> LENGTH: 392
<212> TYPE: PRT
<213> ORGANISM: Artificial Sequence
<220> FEATURE:
<223> OTHER INFORMATION: humanCkappa-linker-IgG3 hinge-IgG1CH2CH3
 protein

<400> SEQUENCE: 110

```
Ser Lys Arg Thr Val Ala Ala Pro Ser Val Phe Ile Phe Pro Pro Ser
  1               5                  10                  15

Asp Glu Gln Leu Lys Ser Gly Thr Ala Ser Val Val Cys Leu Leu Asn
             20                  25                  30

Asn Phe Tyr Pro Arg Glu Ala Lys Val Gln Trp Lys Val Asp Asn Ala
         35                  40                  45

Leu Gln Ser Gly Asn Ser Gln Glu Ser Val Thr Glu Gln Asp Ser Lys
     50                  55                  60

Asp Ser Thr Tyr Ser Leu Ser Ser Thr Leu Thr Leu Ser Lys Ala Asp
 65                  70                  75                  80

Tyr Glu Lys His Lys Val Tyr Ala Cys Glu Val Thr His Gln Gly Leu
                 85                  90                  95

Ser Ser Pro Val Thr Lys Ser Phe Asn Arg Gly Glu Cys Ser Gly Gly
            100                 105                 110

Gly Gly Ser Gly Gly Gly Gly Ser Gly Gly Gly Gly Ser Cys Pro Arg
```

```
                   115                 120                 125
Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Glu Pro Lys Ser Cys Asp Thr Pro Pro Cys Pro Arg Cys Pro Ala
                165                 170                 175

Pro Glu Leu Ala Gly Ala Pro Ser Val Phe Leu Phe Pro Pro Lys Pro
            180                 185                 190

Lys Asp Thr Leu Met Ile Ser Arg Thr Pro Glu Val Thr Cys Val Val
        195                 200                 205

Val Asp Val Ser His Glu Asp Pro Glu Val Lys Phe Asn Trp Tyr Val
    210                 215                 220

Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
                245                 250                 255

Asp Trp Leu Asn Gly Lys Glu Tyr Lys Cys Lys Val Ser Asn Lys Ala
            260                 265                 270

Leu Pro Ala Pro Ile Glu Lys Thr Ile Ser Lys Ala Lys Gly Gln Pro
        275                 280                 285

Arg Glu Pro Gln Val Tyr Thr Leu Pro Pro Ser Arg Asp Glu Leu Thr
    290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly Lys
385                 390
```